(12) United States Patent
Braig et al.

(10) Patent No.: US 7,332,105 B2
(45) Date of Patent: Feb. 19, 2008

(54) SYNERGISTIC UV ABSORBER COMBINATION

(75) Inventors: Adalbert Braig, Binzen (DE); David George Leppard, Marly (CH); Frédérique Wendeborn, Ranspach-le-Haut (FR)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 399 days.

(21) Appl. No.: 10/528,136

(22) PCT Filed: Sep. 23, 2003

(86) PCT No.: PCT/EP03/10567

§ 371 (c)(1),
(2), (4) Date: Mar. 16, 2005

(87) PCT Pub. No.: WO2004/031294

PCT Pub. Date: Apr. 15, 2004

(65) Prior Publication Data

US 2006/0052491 A1    Mar. 9, 2006

(30) Foreign Application Priority Data

Oct. 2, 2002    (EP) .................................. 02405852

(51) Int. Cl.
C08K 5/3492 (2006.01)
C08K 5/34 (2006.01)
C09D 7/12 (2006.01)
C07D 251/24 (2006.01)
C07D 265/34 (2006.01)

(52) U.S. Cl. .................... 252/301.23; 252/182.13; 524/100; 544/218; 544/92

(58) Field of Classification Search ................ 544/216, 544/92; 524/100; 252/301.23, 182.13
See application file for complete search history.

(56) References Cited

U.S. PATENT DOCUMENTS

| 3,535,318 | A |  | 10/1970 | Oppelt et al. ............ 260/249.6 |
|---|---|---|---|---|
| 5,274,015 | A |  | 12/1993 | Deslauriers et al. ......... 524/91 |
| 5,597,854 | A |  | 1/1997 | Birbaum et al. ............ 524/100 |
| 6,218,450 | B1 |  | 4/2001 | Fagerburg .................... 524/91 |
| 6,255,483 | B1 | * | 7/2001 | Fletcher et al. ............. 544/216 |
| 6,297,300 | B1 |  | 10/2001 | Van Nuffel ................. 524/91 |
| 6,352,783 | B1 |  | 3/2002 | Fagerburg ................... 428/480 |
| 6,841,670 | B2 |  | 1/2005 | Fletcher et al. ............. 544/216 |
| 2001/0039304 | A1 |  | 11/2001 | Gugumus .................... 524/100 |
| 2002/0083641 | A1 |  | 7/2002 | Leppard et al. ............. 47/29.4 |
| 2003/0065066 | A1 |  | 4/2003 | Jakiela et al. ............... 524/100 |
| 2003/0096993 | A1 |  | 5/2003 | Hayoz ........................ 544/215 |
| 2003/0225192 | A1 |  | 12/2003 | Birbaum et al. ............ 524/100 |
| 2004/0241111 | A1 |  | 12/2004 | Lazzari et al. ............... 424/59 |
| 2005/0019281 | A1 |  | 1/2005 | Fletcher et al. .............. 424/59 |
| 2005/0038245 | A1 |  | 2/2005 | Van Toan et al. ........... 544/208 |

FOREIGN PATENT DOCUMENTS

| EP | 0816346 | 1/1998 |
|---|---|---|
| WO | 01/90244 | 11/2001 |
| WO | 02/17873 | 3/2002 |
| WO | 02/062890 | 8/2002 |
| WO | 03/057772 | 7/2003 |

OTHER PUBLICATIONS

Patent Abstracts of Japan Publication No. 04257582 (1992).

* cited by examiner

*Primary Examiner*—Venkataraman Balasubram
(74) *Attorney, Agent, or Firm*—Shiela A. Loggins

(57) ABSTRACT

A stabilizer composition comprising (A) a compound of the formula (I) wherein R is $(CH_2—CH_2—O—)_n$, $—R_2$; $—CH_2—CH(OH)—CH_2—O—R_2$; or $—CH(R_3)—CO—O—R_4$; n is 0 or 1; $R_2$ is $C_1-C_{13}$alkyl or $C_2C_{20}$alkenyl or $C_6-C_{12}$aryl or $CO—C_1-C_{18}$alkyl; $R_3$ is H or $C_1-C_8$ alkyl; $R_4$ is $C_1-C_{12}$alkyl or $C_2-C_{12}$alkenyl or $C_5C_6$cycloalkyl; and (B) one or more compounds selected from benzotriazoles of the formula (IIa), 2-hydroxybenzophenones of the formula (IIb), oxalanilides of the formula (IIc), 2-hydroxyphenyltriazines of formula (IId), cinnamates of formula (IIe), and benzoates of formula (IIf) as defined in claim 1, is especially effective towards stabilizing organic materials against degradation induced by light, heat or oxidation.

16 Claims, No Drawings

SYNERGISTIC UV ABSORBER COMBINATION

The invention relates to a novel stabilizer mixture comprising specific compounds of the 2,4-bis-(4-phenylphenyl)-6-(2-hydroxyphenyl)-1,3,5-triazine class and selected other UV absorbers, to organic material stabilized with the aid of this mixture against damage by light, heat and oxygen, and to the corresponding use of the mixtures as stabilizers for organic material.

Some mixtures of UV absorbers for stabilizing organic polymers against harmful radiation in combination with heat and oxygen have been described in U.S. Pat. Nos. 5,106,891, 5,668,200 and 6,060,543.

Certain combinations of ultraviolet absorbers (UVA) have now been found to be especially efficacious towards stabilizing organic material against degradation induced by UV light, heat and/or oxidation. The present stabilizer combination may be incorporated into the material in order to protect it, or be used as or within a UV filter layer for preventing UV radiation to reach the material.

Thus, subject of the invention is a composition comprising (A) a compound of the formula I

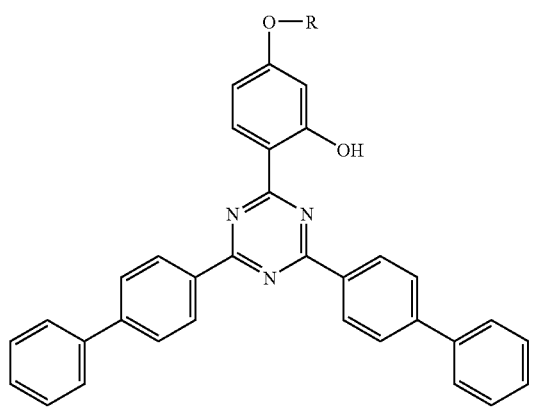

wherein R is $(CH_2-CH_2-O-)_n-R_2$; $-CH_2-CH(OH)-CH_2-O-R_2$; or $-CH(R_3)-CO-O-R_4$; n is 0 or 1; $R_2$ is $C_1-C_{13}$alkyl or $C_2-C_{20}$alkenyl or $C_6-C_{12}$aryl or $CO-C_1-C_{18}$alkyl; $R_3$ is H or $C_1-C_8$alkyl; $R_4$ is $C_1-C_{12}$alkyl or $C_2-C_{12}$alkenyl or $C_5-C_6$cycloalkyl; and (B) a compound selected from benzotriazoles the formula (IIa), 2-hydroxybenzophenones of the formula (IIb), oxalanilides of the formula (IIc), 2-hydroxyphenyltriazines of formula (IId), cinnamates of formula (IIe), and benzoates of formula (IIf)

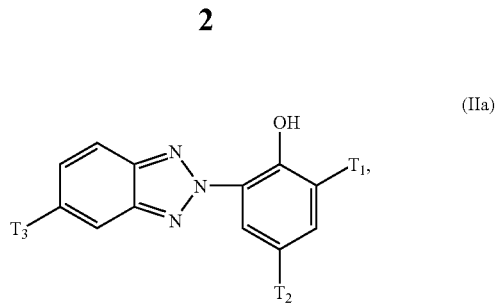

wherein $T_1$ is hydrogen, $C_1-C_{18}$alkyl, or $C_1-C_{18}$alkyl which is substituted by phenyl, or $T_1$ is a group of the formula

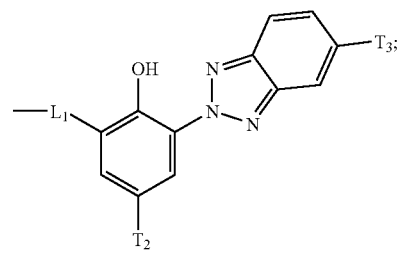

$L_1$ is a divalent group, for example $-(CH_2)_n-$, where n is from the range 1-8;

$T_2$ is hydrogen, $C_1-C_{18}$alkyl, or is $C_1-C_{18}$alkyl which is substituted by $COOT_5$, $C_1-C_{18}$alkoxy, hydroxyl, phenyl or $C_2-C_{18}$acyloxy;

$T_3$ is hydrogen, halogen, $C_1-C_{18}$alkyl, $C_1-C_{18}$alkoxy, $C_2-C_{18}$acyloxy, perfluoroalkyl of 1 to 12 carbon atoms such as $-CF_3$, or $T_3$ is phenyl;

$T_5$ is $C_1-C_{18}$alkyl or $C_4-C_{50}$alkyl interrupted by one or more O and/or substituted by OH or by a group

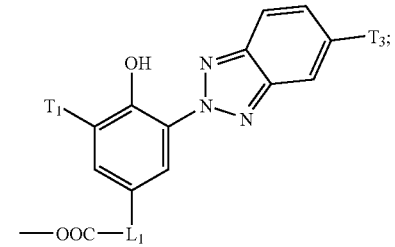

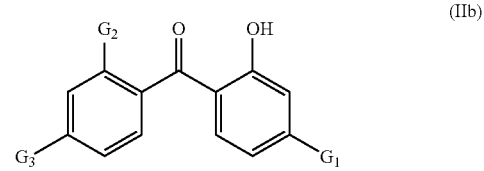

wherein

G₁, G₂ and G₃ independently are hydrogen, hydroxy or C₁-C₁₈alkoxy;

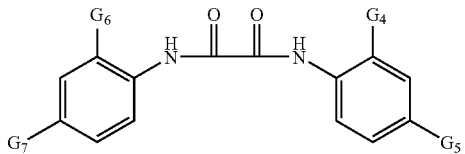
(IIc)

wherein

G₄, G₅, G₆ and G₇ independently are hydrogen, C₁-C₁₂alkyl or C₁-C₁₂alkoxy;

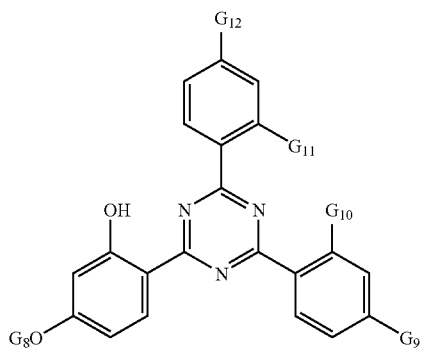
(IId)

wherein

G₈ is C₁-C₁₈alkyl, or is C₄-C₁₈alkyl which is interrupted by COO or OCO or O, or is interrupted by O and substituted by OH;

G₉, G₁₀, G₁₁ and G₁₂ independently are hydrogen, methyl, hydroxy or OG₈;

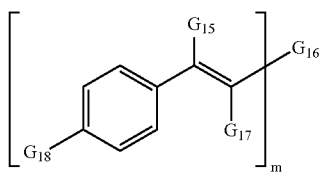
(IIe)

wherein m is an integer from 1 to 4;

G₁₅ is hydrogen or phenyl;

if n is 1, G₁₆ is COO-G₁₉;

if n is 2, G₁₆ is C₂-C₁₂alkane-dioxycarbonyl;

if n is 3, G₁₆ is C₃-C₁₂alkane-trioxycarbonyl;

if n is 4, G₁₆ is C₄-C₁₂alkane-tetraoxycarbonyl;

G₁₇ is hydrogen, CN, or is COO-G₁₉;

G₁₈ is hydrogen or methoxy;

G₁₉ is C₁-C₁₈alkyl;

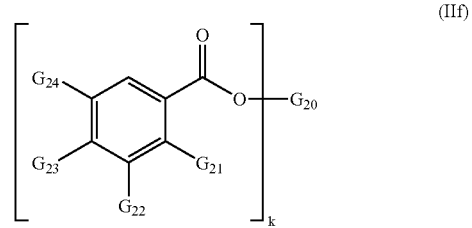
(IIf)

wherein k is 1 or 2;

when k is 1, G₂₀ is C₁-C₁₈alkyl, phenyl or phenyl substituted by C₁-C₁₂alkyl, and G₂₁ is hydrogen;

when k is 2, G₂₀ and G₂₁ together are the tetravalent group

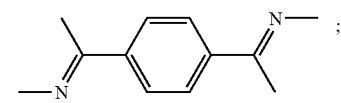

G₂₂ and G₂₄ independently are hydrogen or C₁-C₈alkyl;

G₂₃ is hydrogen or hydroxy, provided that R in formula (I) is $(CH_2-CH_2-O-)_n-R_2$ if component (B) contains a 2-hydroxyphenyltriazine of formula (IId) wherein G₉, G₁₀, G₁₁ or G₁₂ are methyl.

Preferably, component (B) comprises one or more compounds selected from (i) to (xlv):

i. 2-(3',5'-di-tert-butyl-2'-hydroxyphenyl)-5-chlorobenzotriazole, ii. 2-(3',5'-di-tert-amyl-2'-hydroxyphenyl)benzotriazole, iii. 2-(3',5'-bis(α,α-dimethylbenzyl)-2'-hydroxyphenyl)benzotriazole, iv. 2-(3'-tert-butyl-2'-hydroxy-5'-(2-octyloxycarbonylethyl)phenyl)benzotriazole, v. 2,2'-methylene-bis[4-(1,1,3,3-tetramethylbutyl)-6-benzotriazole-2-ylphenol], vi. the transesterification product of 2-[3'-tert-butyl-5'-(2-methoxycarbonylethyl)-2'-hydroxyphenyl]-2H-benzotriazole with polyethylene glycol 300, vii. 2-[2'-hydroxy-3'-(α,α-dimethylbenzyl)-5'-(1,1,3,3-tetramethylbutyl)phenyl]benzotriazole, viii. 5-trifluoromethyl-2-(2-hydroxy-3-α-cumyl-5-tert-octylphenyl)-2H-benzotriazole, ix. 2-(2'-hydroxy-5'-(2-hydroxyethyl)phenyl)benzotriazole, x. 2-(2'-hydroxy-5'-(2-methacryloyloxyethyl)phenyl)benzotriazole, xi. 2,4-bis(2,4-dimethylphenyl)-6-(2-hydroxy-4-alkyloxyphenyl)-1,3,5-triazine, where alkyl is a mixture of C₈-alkyl groups (CAS Nos. 137759-38-7; 85099-51-0; 85099-50-9);

xii. 2,4-bis(2,4-dimethylphenyl)-6-(2-hydroxy-4-octyloxyphenyl)-1,3,5-triazine (CAS No. 2725-22-6), xiii. 2,4-diphenyl-6-(2-hydroxy-4-[α-ethylhexanoyloxyethyl]phenyl)-1,3,5-triazine, xiv. 2,4-bis(2-hydroxy-4-butyloxyphenyl)-6-(2,4-bis-butyloxyphenyl)-1,3,5-triazine, xv. 2,4,6-tris(2-hydroxy-4-[1-ethoxycarbonylethoxy]phenyl)-1,3,5-triazine, xvi. the reaction product of tris(2,4-dihydroxyphenyl)-1,3,5-triazine with the mixture of α-chloropropionic esters (made from isomer mixture of C₇-C₉alcohols), xvii. 2-[4-(dodecyloxy/tridecyloxy-2-hydroxypropoxy)-2-hydroxyphenyl]-4,6-bis(2,4-dimethylphenyl)1,3,5-triazine,
xviii. 2-{2-hydroxy-4-[3-(2-ethylhexyl-1-oxy)-2-hydroxypropyloxy]phenyl}-4,6-bis(2,4-dimethylphenyl)-1,3,5-triazine,
xix. 2-(2-hydroxy-4-hexyloxyphenyl)-4,6-diphenyl-1,3,5-triazine,
xx. 2-(3'-tert.butyl-5'-methyl-2'-hydroxyphenyl)-5-chloro-benzotriazole,
xxi. 2-(3'-sec. butyl-5'-tert.butyl-2'-hydroxyphenyl)-benzotriazole,
xxii. 2-(3',5'-di-tert-butyl-2'-hydroxyphenyl)-benzotriazole,
xxiii. 2-(5'-tert.octyl-2'-hydroxyphenyl)-benzotriazole,
xxiv. 2-(3'-dodecyl-5'-methyl-2'-hydroxyphenyl)-benzotriazole,
xxv. 2-(3'-tert.butyl-5'-(2-octyloxycarbonylethyl)-2'-hydroxyphenyl)-5-chloro-benzotriazole,
xxvi. 2-(5'-methyl-2'-hydroxyphenyl)-benzotriazole,
xxvii. 2-(5'-tert.butyl-2'-hydroxyphenyl)-benzotriazole, the compound of formula

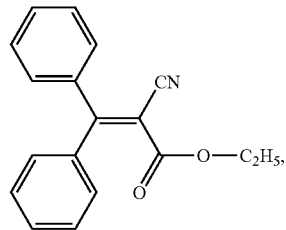

xxxi. the compound of formula

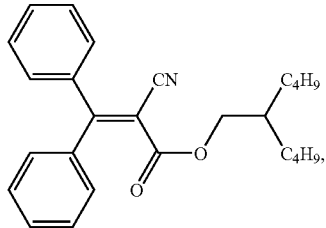

xxxii. 2-ethylhexyl-p-methoxycinnamate (CAS No. 5466-77-3),
xxxiii. 2,4-dihydroxybenzophenone,
xxxiv. 2-hydroxy-4-methoxybenzophenone,
xxxv. 2-hydroxy-4-dodecyloxybenzophenone,
xxxvi. 2-hydroxy-4-octyloxybenzophenone,
xxxvii. 2,2'-dihydroxy-4-methoxybenzophenone,
xxxviii. the compound of formula

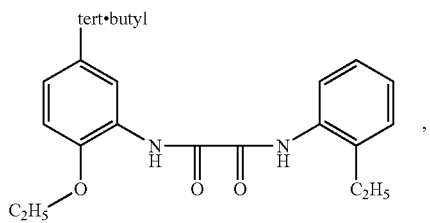

xxxix. the compound of formula

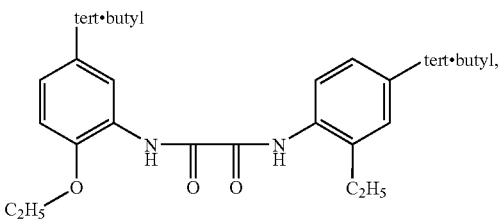

xl. the compound of formula

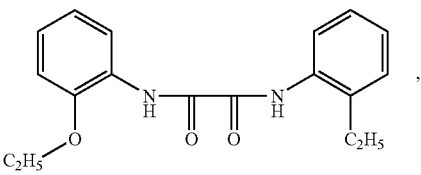

xli. the compound of formula

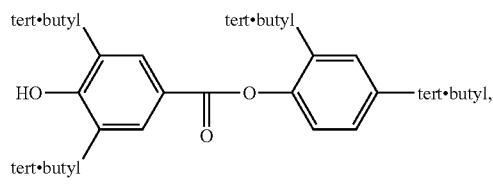

xlii. the compound of formula

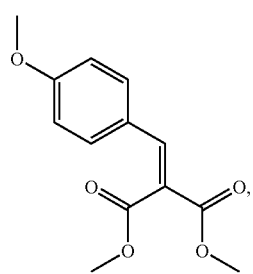

xliii. the compound of formula

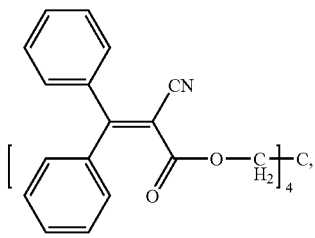

xliv. the compound of formula

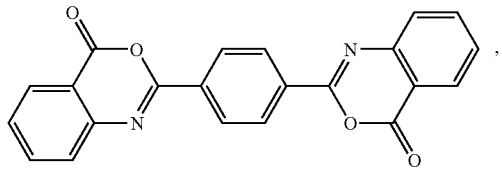

xlv. the compound of formula

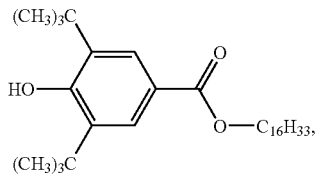

provided that R in formula (I) is (CH$_2$—CH$_2$—O—)$_n$—R$_2$ if component (B) contains compound xi, xii, xvii or xviii.

In the context of the definitions given, including R$_2$, R$_3$ or R$_4$, alkyl is, for example, branched or unbranched alkyl such as methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl.

Alkyl interrupted by more than one O is, for example, polyoxyalkylene such as a polyethylene glycol residue.

Aryl is in general an aromatic hydrocarbon radical, for example phenyl, biphenylyl or naphthyl.

Within the context of the definitions indicated alkenyl comprises, inter alia, vinyl, allyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl, n-octadec-4-enyl.

Halogen is mainly fluoro, chloro, bromo or iodo, especially chloro.

C$_5$-C$_6$cycloalkyl mainly is cyclopentyl, cyclohexyl.

C$_2$-C$_{18}$acyloxy is, for example, alkanoyloxy, benzoyloxy, or alkenoyloxy such as acryloyloxy or methacryloyloxy.

An example for the divalent C$_2$-C$_{12}$alkane-dioxycarbonyl is —COO—CH$_2$CH$_2$—OCO—; an example for the trivalent C$_3$-C$_{12}$alkane-trioxycarbonyl is —COO—CH$_2$—CH(OCO—)CH$_2$—OCO—; an example for the tetravalent C$_4$-C$_{12}$alkane-tetraoxycarbonyl is (—COO—CH$_2$)$_4$C.

Each of components (A) and (B) may be a single compound or a mixture of compounds.

In compound xvii of component (B), the dodecyl/tridecyl residue usually is a mixture of isomers. In compound xvi of component (B), the octyl residue is a mixture mainly of n-octyl and 2-ethylhexyl.

In a preferred embodiment, component (A) is selected from the compounds of formula (I), wherein R is C$_1$-C$_{13}$alkyl or —CH(R$_3$)—CO—O—R$_4$ with R$_3$ and R$_4$ independently are H or C$_1$-C$_8$alkyl;

(A1)  2-{2-hydroxy-4-[1-octyloxycarbonylethoxy]phenyl}-4,6-bis(4-phenylphenyl)-1,3,5-triazine and/or
(A2)  2-(2-hydroxy-4-(2-ethylhexyl)oxy)phenyl-4,6-bis(4-phenyl)phenyl-1,3,5-triazine of the formulae

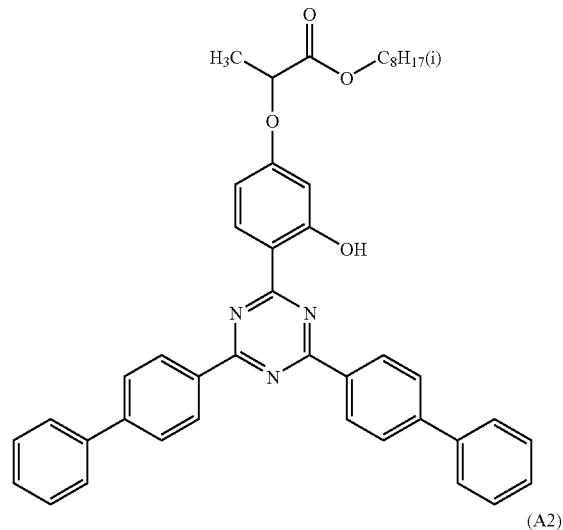

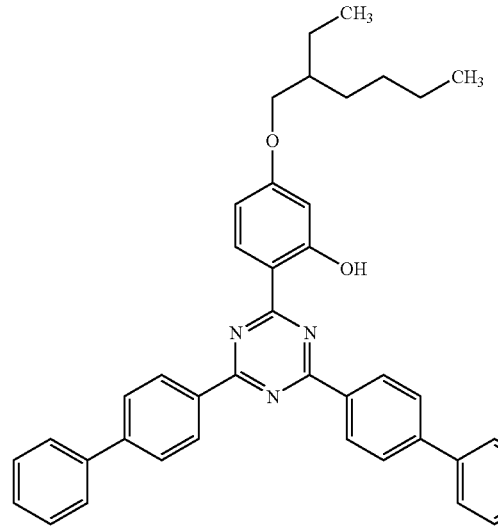

In formula (A1), the moiety C$_8$H$_{17}$(i) usually is an isomer mixture of branched and unbranched octyl groups (see example A14 of U.S. Pat. No. 6,060,543).

In another preferred embodiment, component (B) is selected from the compounds i-xx.

In a specific embodiment, component (A) is selected from compounds whose residue R contains an uninterrupted, branched or unbranched C$_7$-C$_{13}$alkyl chain.

Of specific technical interest is a composition wherein component (A) is the compound (A1) and component (B) is
  selected from the compounds i-iv, vi-xi, xiii-xviii, xx, xxiii-xxxix; especially ii, iii, iv, vi, vii, viii, xx, xxv, xxxvii; in particular those of the benzotriazole class or wherein component (A) is the compound (A2) and component (B) is
  selected from the compounds i-x, xii, xiii, xix-xxiii, xxv-xxvii, xxx-xxxvi, and xi-xlv; especially i, ii, iii, v, vi, viii, xii, xiii, xix, xx, xxii, xxiii, xxvi, xxx, xxxi, xxxiv, xxxvi, xl, xli, xlii, xliii, xliv, xlv.

Each of components (A) and (B) may be a single compound or a mixture of compounds; of particular interest is a combination wherein component (B) is a mixture of compounds.

Of particular interest as component (B) are compounds of the benzotriazole or benzophenone class.

Compounds of component (A) are known e.g. from U.S. Pat. No. 5,959,008 and U.S. Pat. No. 6,255,483.

Compounds of component (B) are known, e.g. compound xvi disclosed in WO 01/47900, example 4; these compounds (B) are commercially available, inter alia from
Ciba Specialty Chemicals, Switzerland;
Clariant, Switzerland;
BASF, Germany;
Cytec Corp., USA.

Further preferred compounds of component (A) are of the formulae

A3)

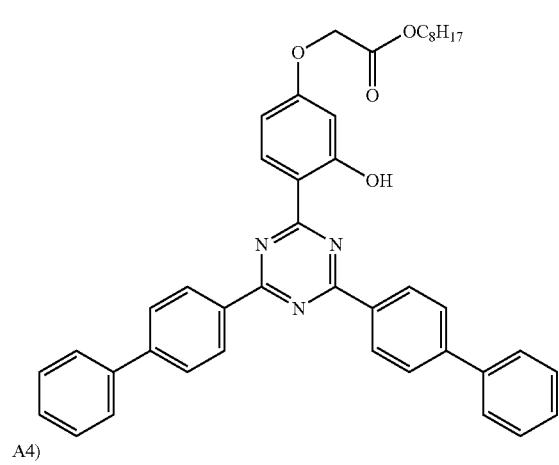

A4)

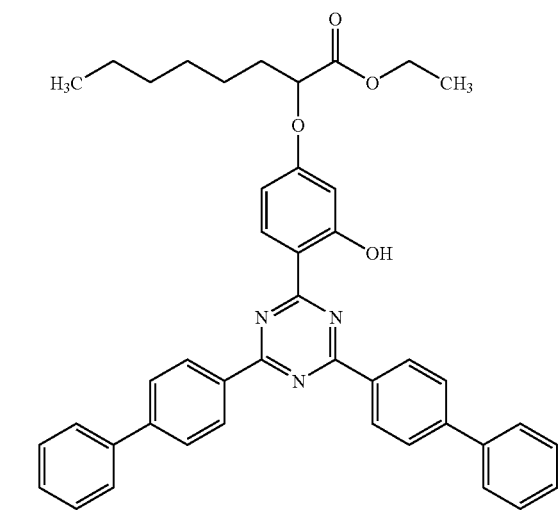

A5)

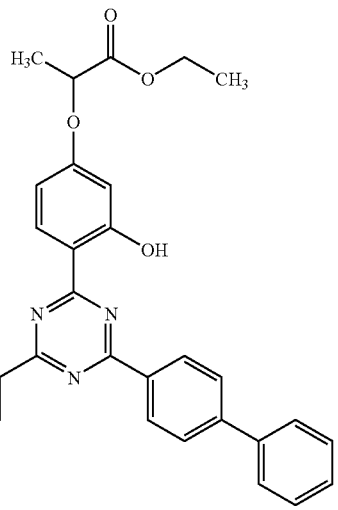

A6)

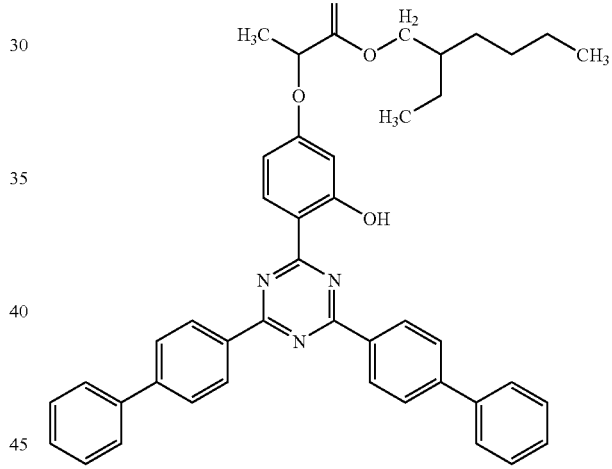

A7)

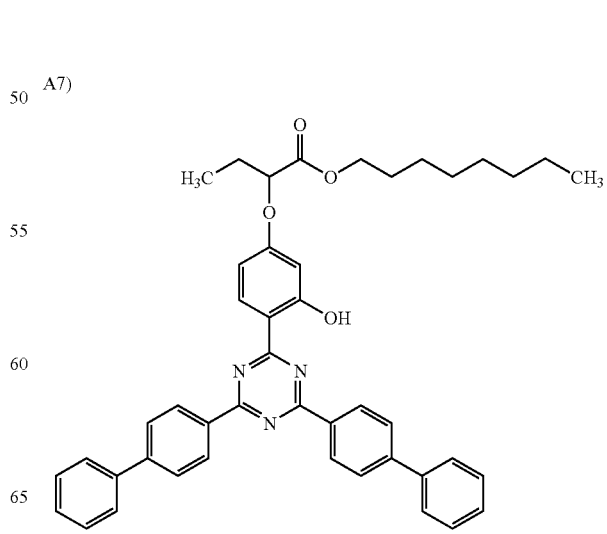

-continued
A8)
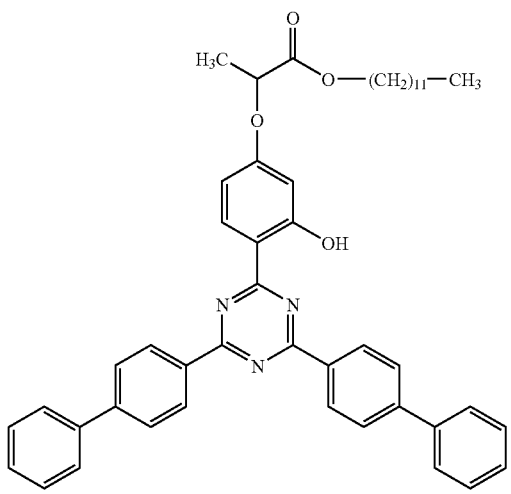
A9)
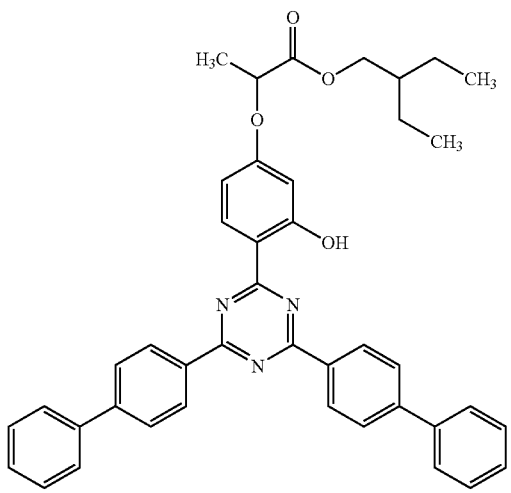
A10)
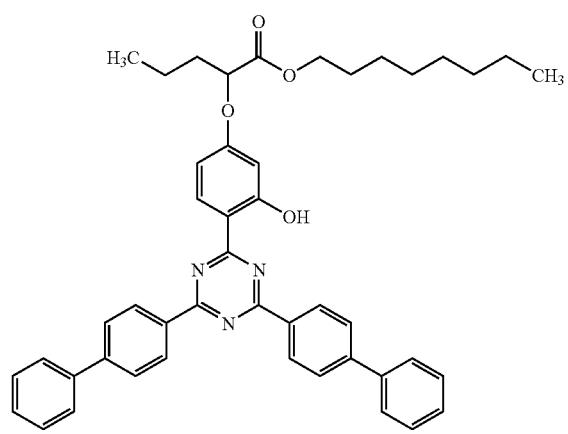
-continued
A11)
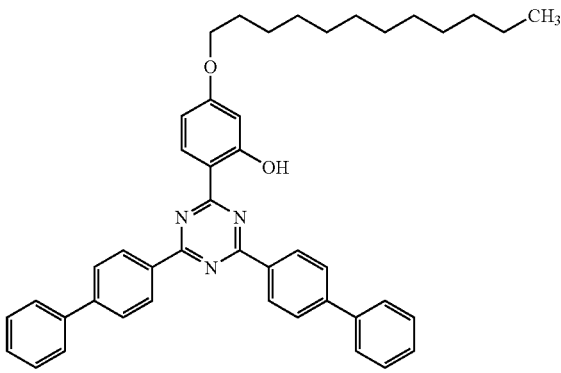
A12)
A13)
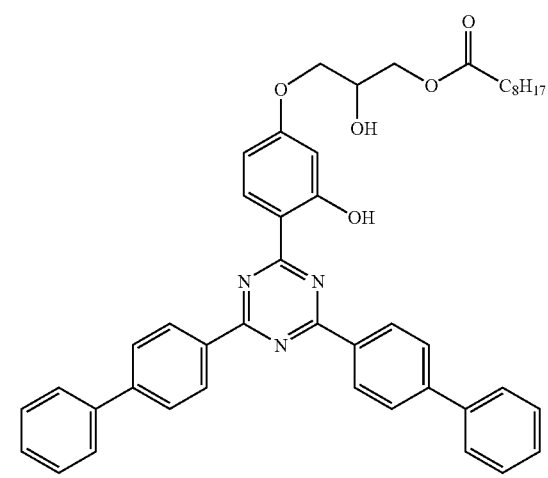

A14)

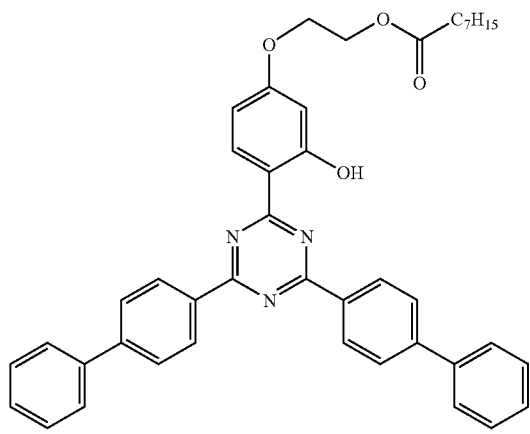

A15)

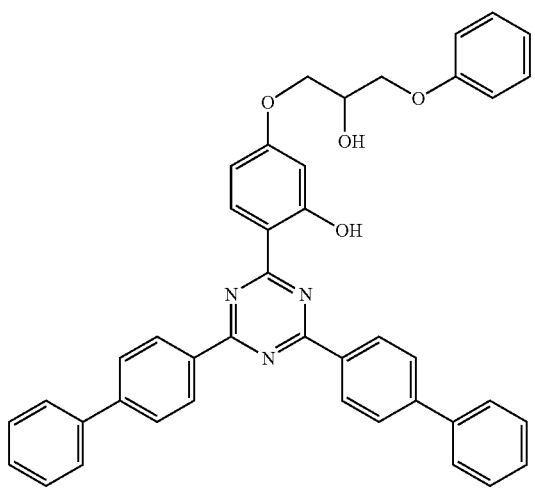

A16)

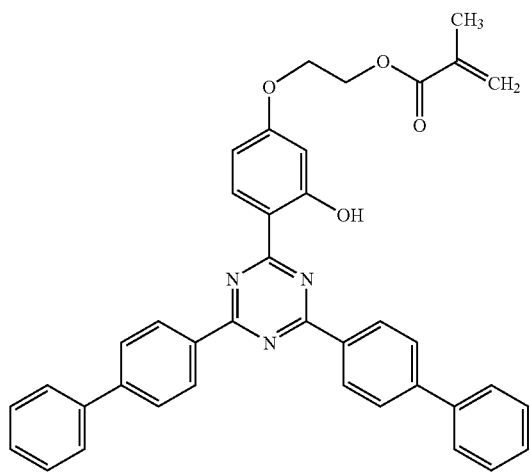

Further Additives Optionally to be Employed

Other additives optionally to be combined with the present UV absorbers include, for example, plasticizers, lubricants, emulsifiers, pigments, rheology additives, catalysts, flow-control agents, optical brighteners, further light stabilizers, antioxidants, clarifiers such as substituted and unsubstituted bisbenzylidene sorbitols, flameproofing agents, anti-static agents, benzoxazinone UV absorbers, blowing agents and thiosynergists such as dilauryl thiodipropionate or distearyl thiodipropionate. Examples are listed below:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)-disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-ditert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxy-anilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine, 1,3,5-tris(3,5-di-tert-butyl-4-hydroxy-phenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetra-methyl-4,4'-diaminodiphenylmethane, 1,2-bis[(2-methylphenyl)amino] ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilisers 2.1. Further 2-(2'-Hydroxyphenyl)benzotriazoles, for example 2-(2'-hydroxy-5'-(1,1,3,3-tetramethylbutyl)phenyl) benzotriazole, 2-(2'-hydroxy-4'-octyloxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl) benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

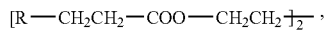

where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]-benzotriazole; 2-[2'-hydroxy-3'-(1,1,3,3-tetramethylbutyl)-5'-(α,α-dimethylbenzyl)phenyl] benzotriazole.

2.2. Further 2-Hydroxybenzophenones, for example the 4-decyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris (2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)-malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)-ethane, the condensate of 2-chloro-4,6-di-(4-n-butylamino-1,2,2,6,6-pentamethylpiperidyl)-1,3,5-triazine and 1,2-bis (3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl) pyrrolidine-2,5-dione, 5-(2-ethylhexanoyl)-oxymethyl-3,3,5-trimethyl-2-morpholinone, 1-(2-hydroxy-2-methylpropoxy)-4-octadecanoyloxy-2,2,6,6-tetramethylpiperidine, 1,3,5-tris(N-cyclohexyl-N-(2,2,6,6-tetramethylpiperazin-3-on-4-yl)amino)-s-triazine, 1,3,5-tris (N-cyclohexyl-N-(1,2,2,6,6-pentamethylpiperazin-3-on-4-yl)amino)-s-triazine, the reaction product of 2,4-bis[(1-cyclohexyloxy-2,2,6,6-piperidin-4-yl)butylamino]-6-chloro-s-triazine with N,N'-bis(3-aminopropyl) ethylenediamine), a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide; N-(1,2,2,6,6-pentamethyl-4-piperidyl)-n-dodecylsuccinimide; 2-undecyl-7,7,9,9-tetramethyl-1-oxa-3,8-diaza-4-oxo-spiro[4,5]decane; 5-(2-ethylhexanoyl)oxymethyl-3,3,5-trimethyl-2-morpholinone; a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl) ethene, N,N'-bisformyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. Further 2-(2-Hydroxyphenyl)-1,3,5-triazines, for example 2,4,6-tris(2-hydroxy-4-octyloxyphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,4-dicumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)-pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo-[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:

Tris(2,4-di-tert-butylphenyl)phosphite (Irgafose®168, Ciba-Geigy), tris(nonylphenyl)phosphite,

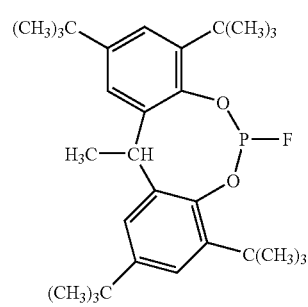
(A)

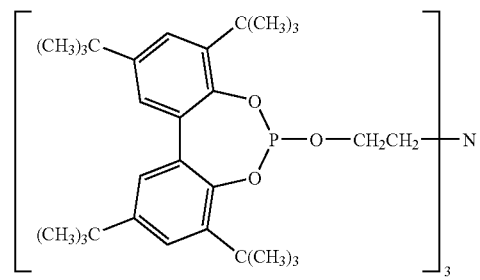
(B)

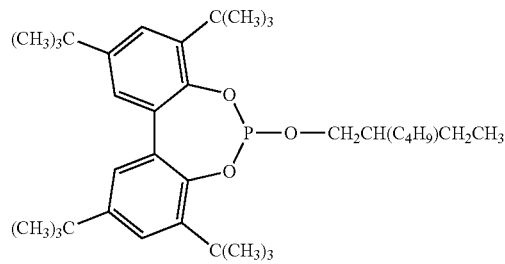
(C)

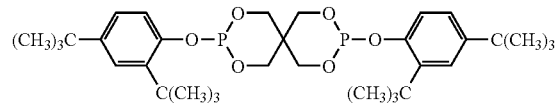
(D)

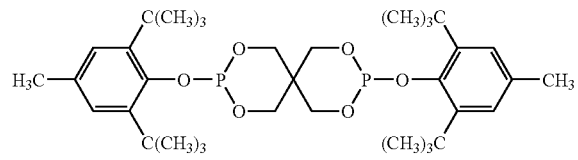
(E)

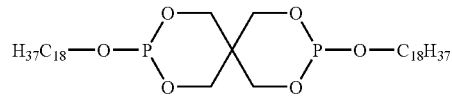
(F)

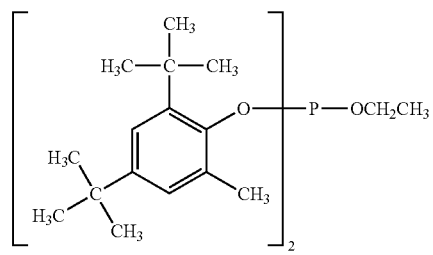
(G)

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-hepta-decylnitrone, N-octadecyl-alpha-hexadecylnitrone, nitrone derived from N,N-dialkylhydroxyl-amine derived from hydrogenated tallow amine.

7. Thiosynergists, for example dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example copper salts in combination with iodides and/or phosphorus compounds and salts of divalent manganese.

10. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene)sorbitol, and 1,3:2,4-di(benzylidene)sorbitol.

12. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butylbenzofuran-2-one, 5,7-di-tert-butyl-3-[4-(2-stearoyloxyethoxy)phenyl]-benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one.

Blends of hindered amine stabilizers are disclosed for example in EP-A-947546. The present UV absorbers may be blended with one or more appropriate additional hindered amines in analogy to the disclosure of EP-A-947546, EP-A-200190, EP-A 434608, EP-A-704560, WO 98/55526, WO 99/57189.

Preferred sterically hindered amine stabilizers (HALS) useful for combining with the above UVA are, for example, the following compounds:

1) 4-hydroxy-2,2,6,6-tetramethylpiperidine
2) 1-allyl-4-hydroxy-2,2,6,6-tetramethylpiperidine
3) 1-benzyl-4-hydroxy-2,2,6,6-tetramethylpiperidine
4) 1-(4-tert-butyl-2-butenyl)-4-hydroxy-2,2,6,6-tetramethylpiperidine
5) 4-stearoyloxy-2,2,6,6-tetramethylpiperidine
6) 1-ethyl-4-salicyloyloxy-2,2,6,6-tetramethylpiperidine
7) 4-methacryloyloxy-1,2,2,6,6-pentamethylpiperidine
8) 1,2,2,6,6-pentamethylpiperidin-4-yl β-(3,5-di-tert-butyl-4-hydroxyphenyl)propionate
9) di(1-benzyl-2,2,6,6-tetramethylpiperidin-4-yl)maleate
10) di(2,2,6,6-tetramethylpiperidin-4-yl)succinate
11) di(2,2,6,6-tetramethylpiperidin-4-yl)glutarate
12) di(2,2,6,6-tetramethylpiperidin-4-yl)adipate
13) di(2,2,6,6-tetramethylpiperidin-4-yl)sebacate
14) di(1,2,2,6,6-pentamethylpiperidin-4-yl)sebacate
14a) a mixture comprising 20% b.w. of (1,2,2,6,6-pentamethylpiperidin-4-yl) (methyl)sebacate and 80% by weight of di(1,2,2,6,6-pentamethylpiperidinyl)-sebacate
15) di(1,2,3,6-tetramethyl-2,6-diethyl-piperidin-4-yl)sebacate
16) di(1-allyl-2,2,6,6-tetramethylpiperidin-4-yl)phthalate
17) 1-hydroxy-4-β-cyanoethoxy-2,2,6,6-tetramethylpiperidine
18) 1-acetyl-2,2,6,6-tetramethylpiperidin-4-yl acetate
19) tri(2,2,6,6-tetramethylpiperidin-4-yl)trimellitate
20) 1-acryloyl-4-benzyloxy-2,2,6,6-tetramethylpiperidine
21) di(2,2,6,6-tetramethylpiperidin-4-yl)diethylmalonate
22) di(1,2,2,6,6-pentamethylpiperidin-4-yl)dibutylmalonate
23) di(1,2,2,6,6-pentamethylpiperidin-4-yl)butyl(3,5-di-tert-butyl-4-hydroxybenzyl)malonate
24) di(1-octyloxy-2,2,6,6-tetramethylpiperidin-4-yl)sebacate
25) di(1-cyclohexyloxy-2,2,6,6-tetramethylpiperidin-4-yl)sebacate
26) hexane-1',6'-bis(4-carbamoyloxy-1-n-butyl-2,2,6,6-tetramethylpiperidine)
27) toluene-2',4'-bis-(4-carbamoyloxy-1-n-propyl-2,2,6,6-tetramethylpiperidine)
28) dimethylbis(2,2,6,6-tetramethylpiperidin-4-oxy)silane
29) phenyltris(2,2,6,6-tetramethylpiperidin-4-oxy)silane
30) tris(1-propyl-2,2,6,6-tetramethylpiperidin-4-yl)phosphite
30-a) tris(1-methyl-2,2,6,6-tetramethylpiperidin-4-yl)phosphite
31) tris(1-propyl-2,2,6,6-tetramethylpiperidin-4-yl)phosphate
32) phenyl bis(1,2,2,6,6-pentamethylpiperidin-4-yl)phosphonate
33) 4-hydroxy-1,2,2,6,6-pentamethylpiperidine
34) 4-hydroxy-N-hydroxyethyl-2,2,6,6-tetramethylpiperidine
35) 4-hydroxy-N-(2-hydroxypropyl)-2,2,6,6-tetramethylpiperidine
36) 1-glycidyl-4-hydroxy-2,2,6,6-tetramethylpiperidine
36-a-1) 1,2,3,4-tetrakis[2,2,6,6-tetramethylpiperidin-4-yloxycarbonyl]butane
36-a-2) bis[2,2,6,6-tetramethylpiperidin-4-yloxycarbonyl]-bis[tridecyloxycarbonyl]butane
36-b-1) 1,2,3,4-tetrakis[1,2,2,6,6-pentamethylpiperidin-4-yloxycarbonyl]butane
36-b-2) bis[1,2,2,6,6-pentamethylpiperidin-4-yloxycarbonyl]-bis[tridecyloxycarbonyl]butane
36-c) 2,2,6,6-tetramethylpiperidin-4-yloxycarbonyl($C_{15}$-$C_{17}$alkane)

36-d)

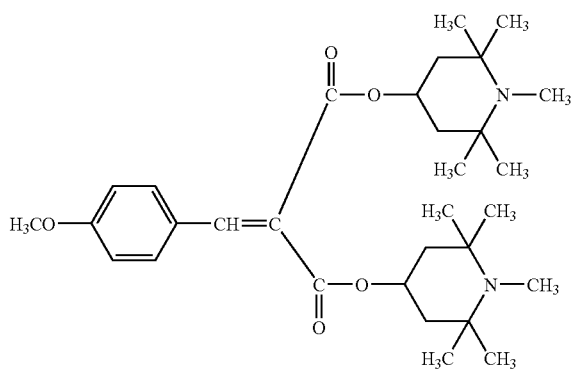

36-e)

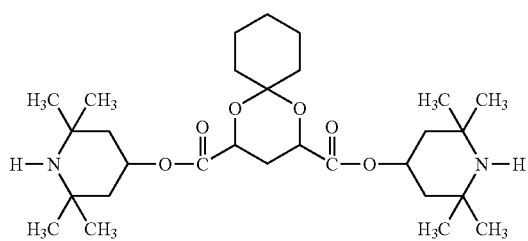

37) N,N'-bis(2,2,6,6-tetramethylpiperidin-4-yl)hexamethylene-1,6-diamine
38) N,N'-bis(2,2,6,6-tetramethylpiperidin-4-yl)hexamethylene-1,6-diacetamide
39) bis(2,2,6,6-tetramethylpiperidin-4-yl)amine
40) 4-benzoylamino-2,2,6,6-tetramethylpiperidine
41) N,N'-bis(2,2,6,6-tetramethylpiperidin-4-yl)-N,N'-dibutyladipamide
42) N,N'-bis(2,2,6,6-tetramethylpiperidin-4-yl)-N,N'-dicyclohexyl-2-hydroxypropylene-1,3-diamine
43) N,N'-bis(2,2,6,6-tetramethylpiperidin-4-yl)-p-xylylenediamine
44) N,N'-bis(2,2,6,6-tetramethylpiperidin-4-yl)succinamide
45) bis(2,2,6,6-tetramethylpiperidin-4-yl) N-(2,2,6,6-tetramethylpiperidin-4-yl)-β-aminodipropionate

46)

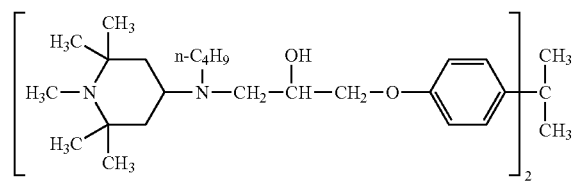

47) 4-(bis-2-hydroxyethylamino)-1,2,2,6,6-pentamethylpiperidine
48) 4-(3-methyl-4-hydroxy-5-tert-butyl-benzamido)-2,2,6,6-tetramethylpiperidine
49) 4-methacrylamido-1,2,2,6,6-pentamethylpiperidine 49-a-1)

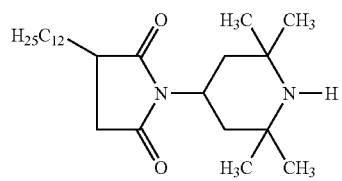

49-a-2)

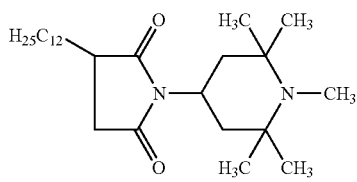

49-a-3)

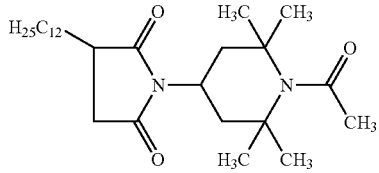

49-b) N,N',N"-tris[2,2,6,6-tetramethylpiperidin-4-ylamino (2-hydroxypropylene)]isocyanurate
49-c) 2-(2,2,6,6-tetramethylpiperidin-4-ylamino)-2-(2,2,6,6-tetramethylpiperidin-4-yl-aminocarbonyl)propane
49-d) 1,6-bis[N-(2,2,6,6-tetramethylpiperidin-4-yl)formylamino]hexane
49-e) 1-(2,2,6,6-tetramethylpiperidin-4-ylamino)-2-(2,2,6,6-tetramethylpiperidin-4-yl-aminocarbonyl)ethane
50) 9-aza-8,8,10,10-tetramethyl-1,5-dioxaspiro[5.5]undecane
51) 9-aza-8,8,10,10-tetramethyl-3-ethyl-1,5-dioxaspiro[5.5]undecane
52) 8-aza-2,7,7,8,9,9-hexamethyl-1,4-dioxaspiro[4.5]decane
53) 9-aza-3-hydroxymethyl-3-ethyl-8,8,9,10,10-pentamethyl-1,5-dioxaspiro[5.5]un-decane
54) 9-aza-3-ethyl-3-acetoxymethyl-9-acetyl-8,8,10,10-tetramethyl-1,5-dioxaspiro [5.5]-undecane
55) 2,2,6,6-tetramethylpiperidine-4-spiro-2'-(1',3'-dioxane)-5'-spiro-5"-(1",3"-dioxane)-2"-spiro-4'"-(2'",2'",6'",6'"-tetramethylpiperidine)
56) 3-benzyl-1,3,8-triaza-7,7,9,9-tetramethylspiro[4.5]decane-2,4-dione
57) 3-n-octyl-1,3,8-triaza-7,7,9,9-tetramethylspiro[4.5]decane-2,4-dione
58) 3-allyl-1,3,8-triaza-1,7,7,9,9-pentamethylspiro[4.5]decane-2,4-dione
59) 3-glycidyl-1,3,8-triaza-7,7,8,9,9-pentamethylspiro[4.5]decane-2,4-dione
60) 1,3,7,7,8,9,9-heptamethyl-1,3,8-triazaspiro[4.5]decane-2,4-dione
61) 2-isopropyl-7,7,9,9-tetramethyl-1-oxa-3,8-diaza-4-oxospiro[4.5]decane
62) 2,2-dibutyl-7,7,9,9-tetramethyl-1-oxa-3,8-diaza-4-oxospiro[4.5]decane
63) 2,2,4,4-tetramethyl-7-oxa-3,20-diaza-21-oxodispiro[5.1.11.2]heneicosane
64) 2-butyl-7,7,9,9-tetramethyl-1-oxa-4,8-diaza-3-oxospiro[4.5]decane 65) 8-acetyl-3-dodecyl-1,3,8-triaza-7,7,9,9-tetramethylspiro[4.5]decane-2,4-dione
66)
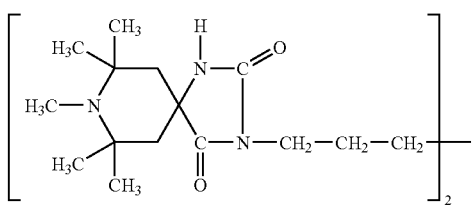
67)
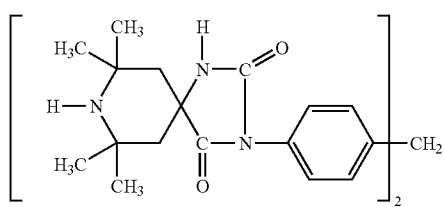
68)
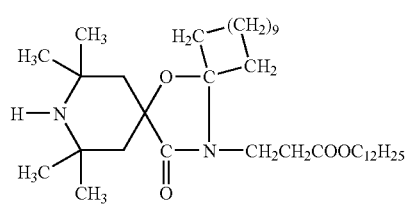
69-a)
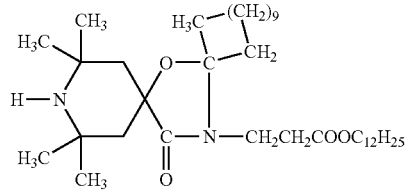
69-b) mixture of 60% by weight of
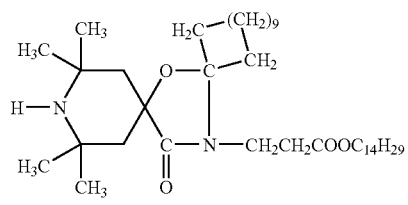
and 40% by weight of
-continued
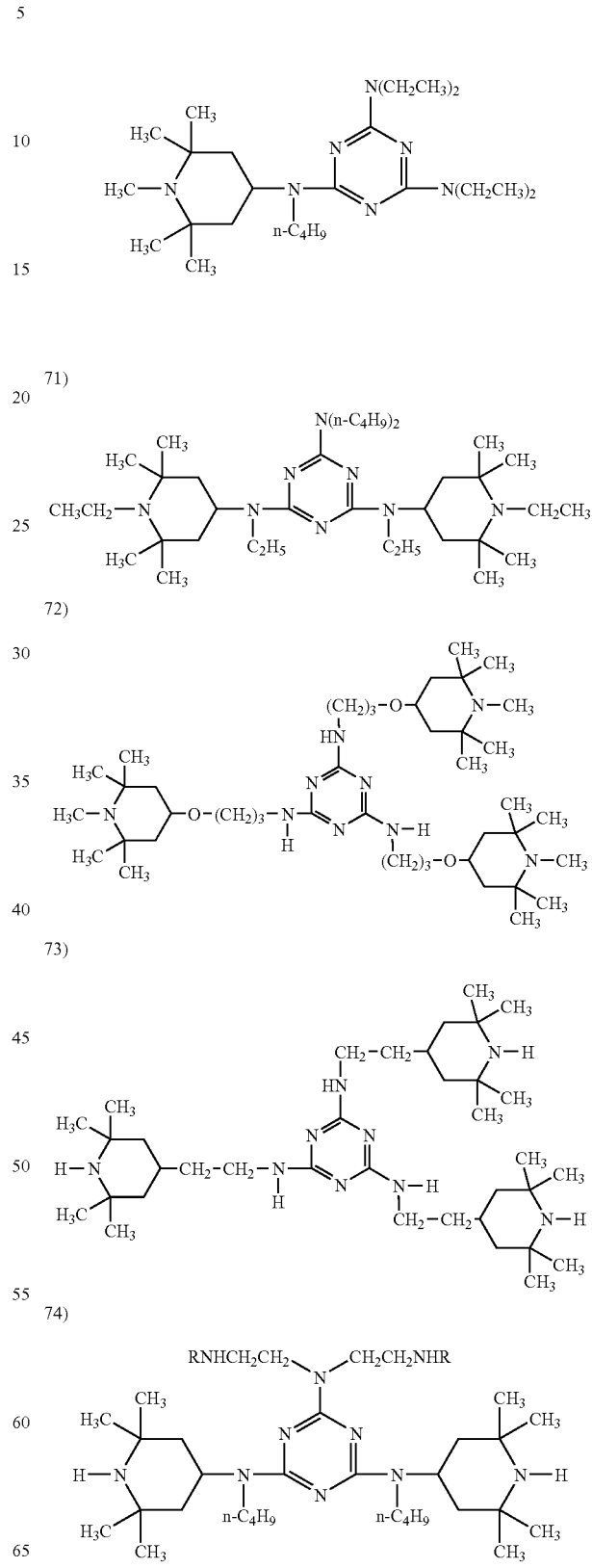

where R is
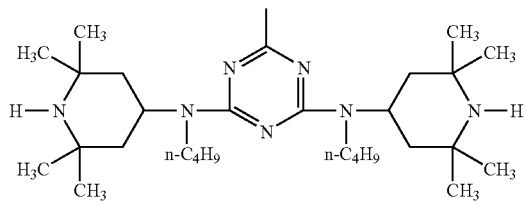
75)
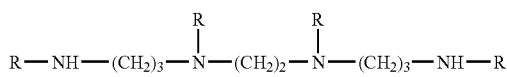
where R has the same meaning as in compound 74
76)
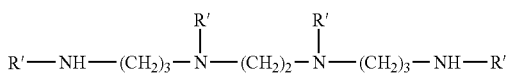
where R' is
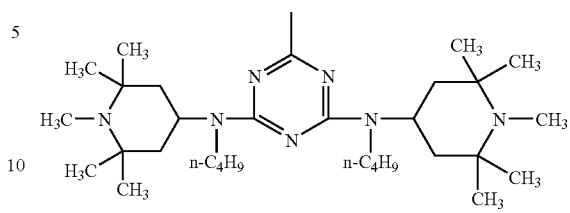
77)
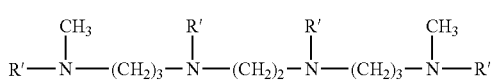
where R' has the same meaning as in compound (76)
78)
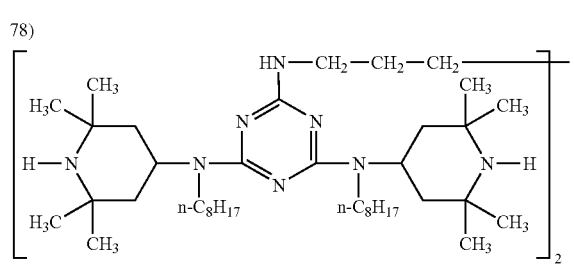
79)
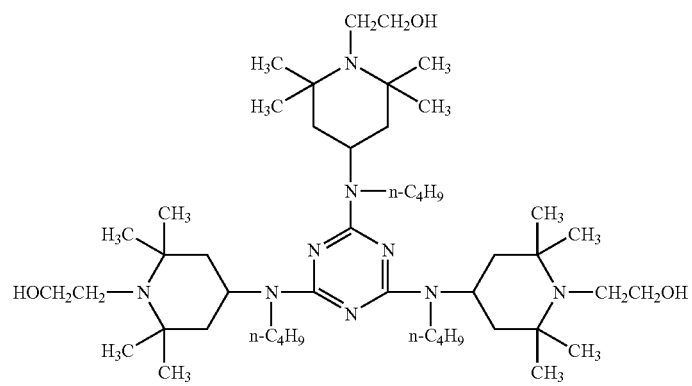

80)
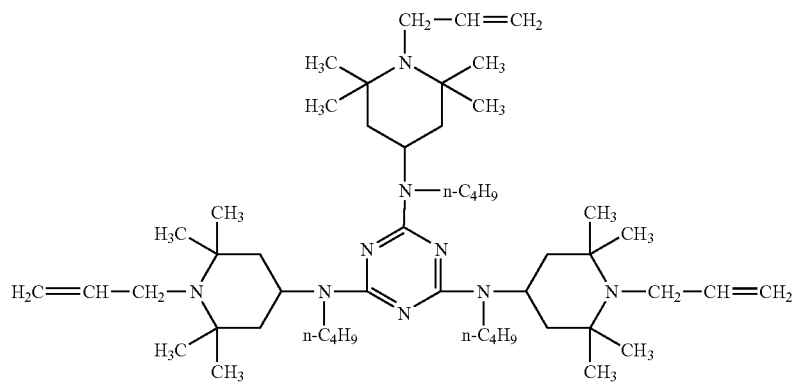
80-1)
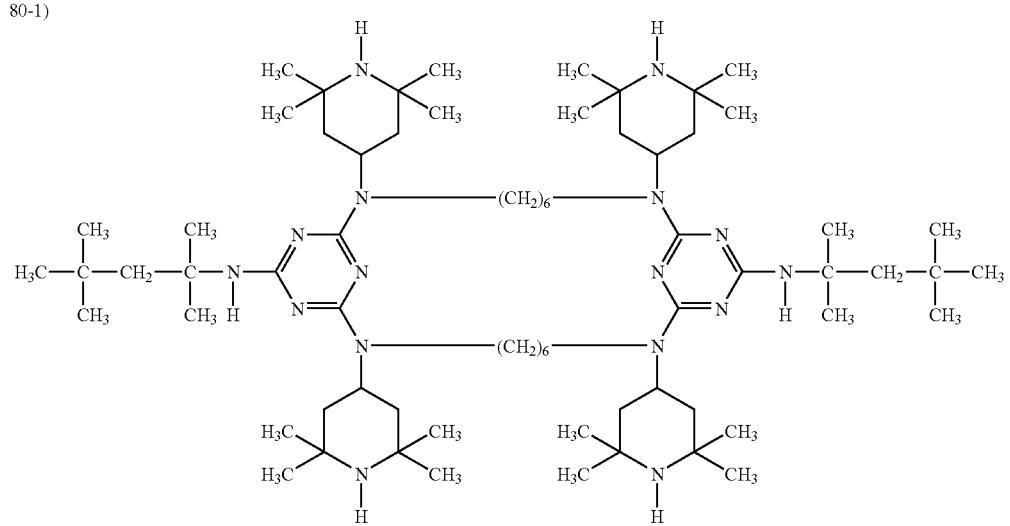
80-a)
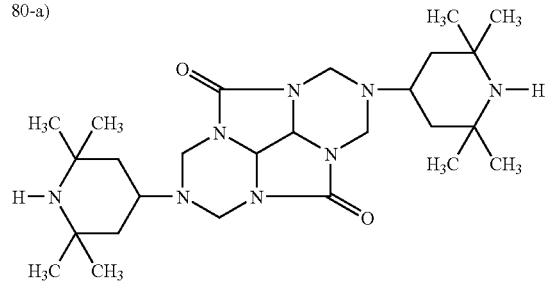

In the following compounds (81) to (83), (84-1), (84-2) and (85) to (91), (91-1), (92-1), (92-2), (93) and (94), $m_1$ to $m_{14}$ is a number from 2 to about 200, preferably 2 to 100, for example 2 to 50, 2 to 40 or 3 to 40 or 4 to 10.

81)

82)

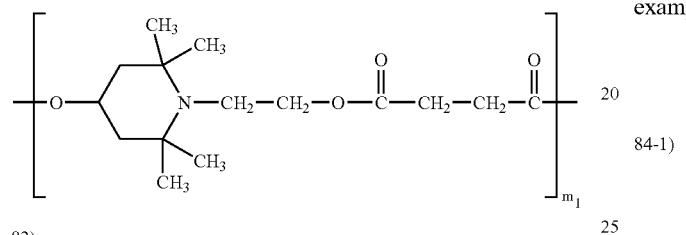

In the compounds (81) and (82), the end group bonded to the —O— can be, for example, hydrogen or a group —CO—(CH$_2$)$_2$—COO—Y or —CO(CH$_2$)$_4$—COO—Y, respectively, with Y being hydrogen or C$_1$-C$_4$alkyl and the end group bonded to the diacyl can be, for example, —O—Y or a group —O—[piperidine]—N—CH$_2$—CH$_2$—OH.

83)

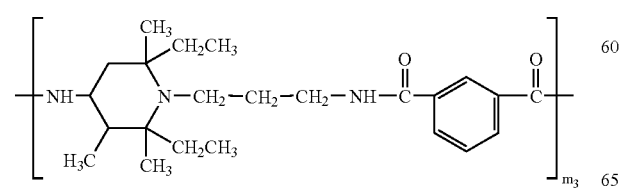

In the compound (83), the end group bonded to the amino residue can be, for example, a group

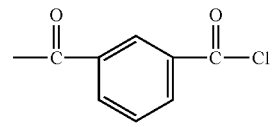

and the end group bonded to the diacyl residue can be, for example, Cl.

84-1)

84-2)

In the compounds (84-1) and (84-2), the end group bonded to the triazine residue can be, for example, chlorine or a group

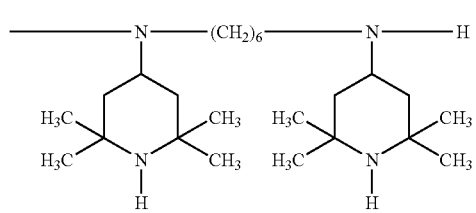

and the end group bonded to the diamino group can be, for example, hydrogen or a group

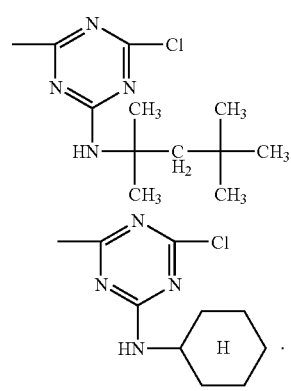

It may be convenient to replace the chlorine attached to the triazine by e.g. —OH or an amino group. Suitable amino groups are typically: pyrrolidin-1-yl, morpholino, —NH$_2$, —N(C$_1$-C$_8$alkyl)$_2$ and —NY'(C$_1$-C$_8$alkyl) wherein Y' is hydrogen or a group of the formula

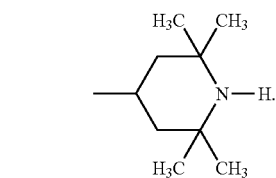

85)

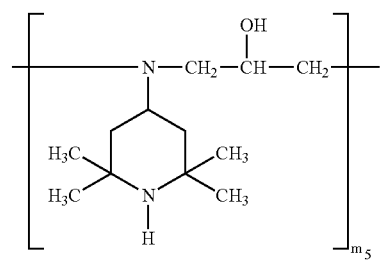

In the compound (85), the end group bonded to the 2,2,6,6-tetramethylpiperidin-4-ylamino residue can be, for example, hydrogen and the end group bonded to the 2-hydroxypropylene residue can be, for example,

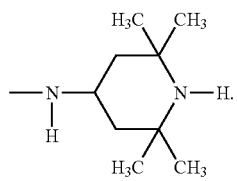

86)

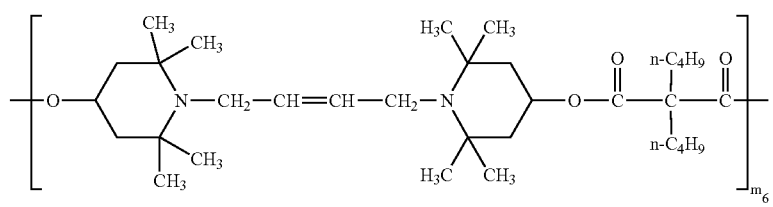

In the compound (86), the end group bonded to the —O— can be, for example, hydrogen or

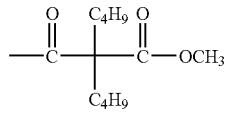

and the end group bonded to the diacyl residue can be, for example, —OCH₃ or Cl.

87)

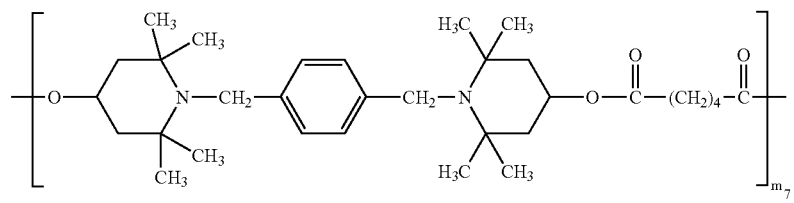

In the compound (87), the end group bonded to the —O— can be, for example, hydrogen or

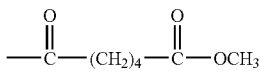

and the end group bonded to the diacyl radical can be, for example, —OCH₃ or Cl.

88)

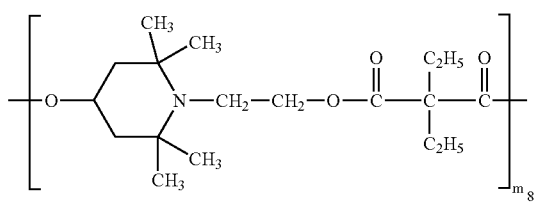

In the compound (88), the end group bonded to the —O— can be, for example, hydrogen or

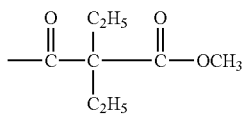

and the end group bonded to the diacyl radical can be, for example, —OCH₃ or Cl.

89)

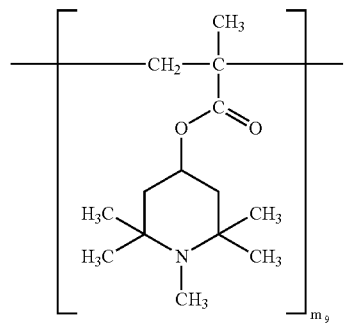

In the compound (89), the end group bonded to the —CH₂— can be, for example, hydrogen and the end group bonded to the ester residue can be, for example,

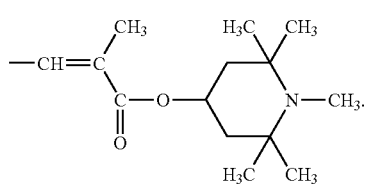

90)

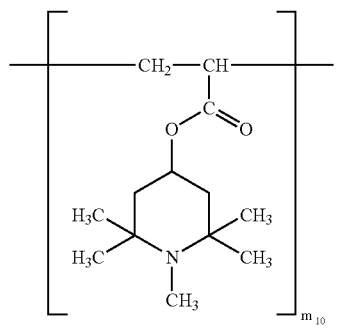

In the compound (90), the end group bonded to the —CH$_2$— can be, for example, hydrogen and the end group bonded to the ester residue can be, for example,

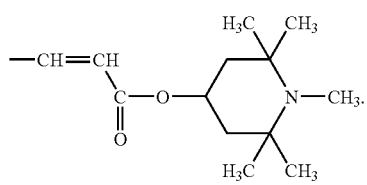

91)

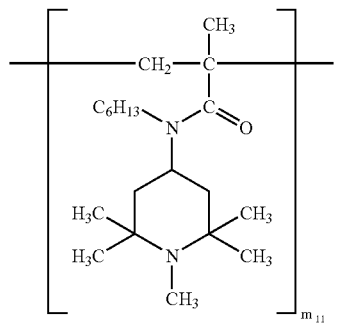

In the compound (91), the end group bonded to the —CH$_2$— can be, for example, hydrogen and the end group bonded to the amide residue can be, for example,

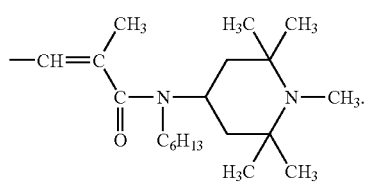

91-1)

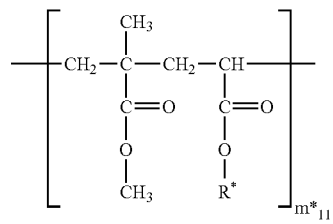

wherein $m_{11}*$ is as defined for $m_{11}$, the radicals R* independently of one another are ethyl or 2,2,6,6-tetramethylpiperidin-4-yl, with the proviso that at least 50% of the radicals R* are 2,2,6,6-tetramethylpiperidin-4-yl and the remaining radicals R* are ethyl. In the compound (91-1), the terminal groups are for example hydrogen.

92-1)

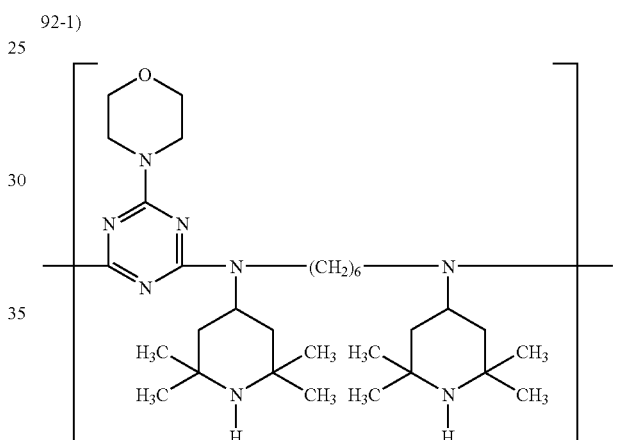

(CA-RN 90751-07-8)

92-2)

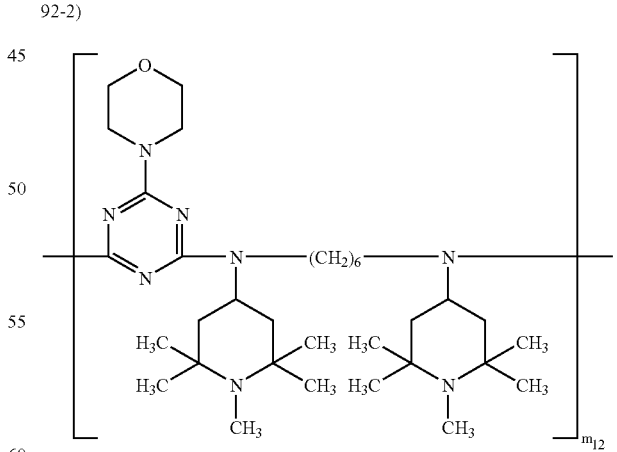

(CA-RN219920-30-6)

In the compounds (92-1) and (92-2), the end group bonded to the triazine residue can be, for example, chlorine or a group

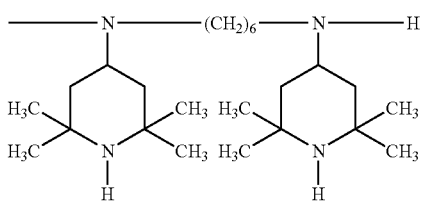

in the compound (92-1), and a group

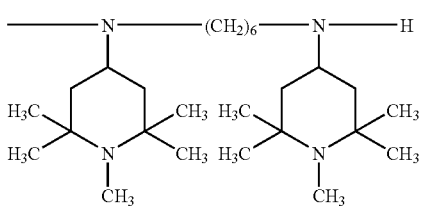

in the compound (92-2), and the end group bonded to the diamino residue can be, for example, hydrogen or a group

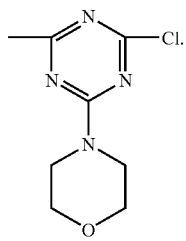

It may be convenient to replace the chlorine attached to the triazine by e.g. —OH or an amino group. Suitable amino groups are typically: pyrrolidin-1-yl, morpholino, —NH$_2$, —N(C$_1$-C$_8$alkyl)$_2$ and —NY'(C$_1$-C$_8$alkyl) wherein Y' is hydrogen or a group of the formula

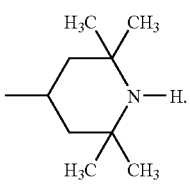

93)

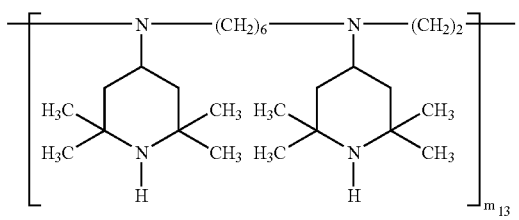

In the compound (93), the end group bonded to the diamino residue can be, for example, hydrogen and the end group bonded to the —CH$_2$CH$_2$— residue can be, for example,

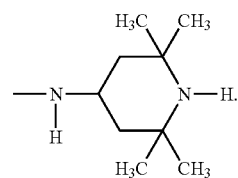

94)

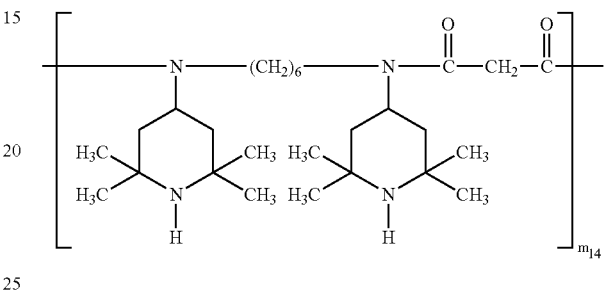

In the compound (94), the end group bonded to the diamino residue can be, for example, hydrogen and the end group bonded to the diacyl residue can be, for example, Cl.

95)

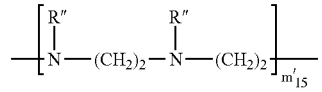

in which R'' is a group of the formula

95-I)

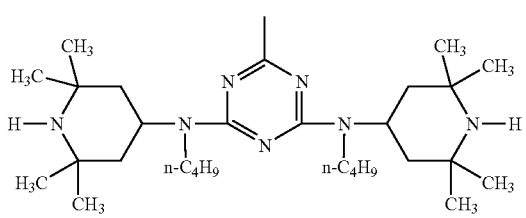

or the chain branching

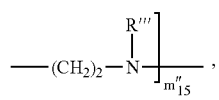

R''' is a group of the formula (95-I), and m'$_{15}$ and m''$_{15}$ are each a number from 0 to 200, preferably 0 to 100, in particular 0 to 50, with the proviso that m'$_{15}$+m''$_{15}$ is a number from 2 to 200, preferably 2 to 100, in particular 2 to 50. In the compound 95, the end group bonded to the diamino residue can be, for example, hydrogen and the end group bonded to the —CH$_2$CH$_2$— group can be, for example, halogen, in particular Cl or Br.

96) the compound of the formula (96-I) or (96-II)

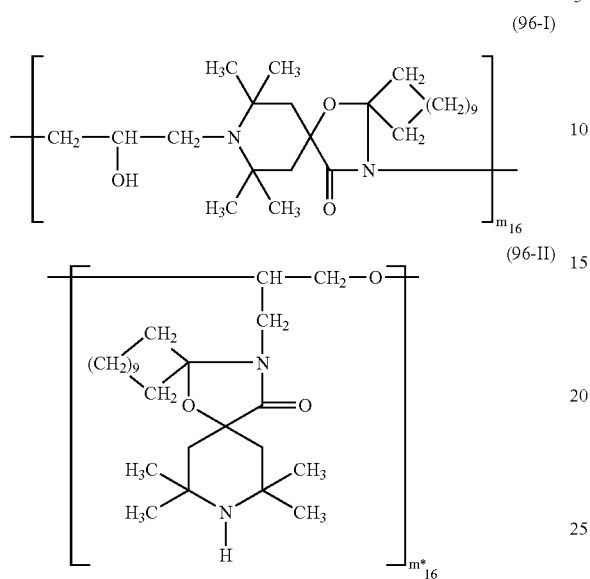

wherein m$_{16}$ and m$_{16}$* are a number from 2 to 50.

During the preparation, the compounds of the formulae (96-I) and (96-II) can be obtained together as a mixture and therefore, can also be employed as such. The (96-I):(96-II) ratio is, for example, from 20:1 to 1:20 or from 1:10 to 10:1.

In the compounds of the formula (96-I), the terminal group bonded to the nitrogen can be, for example, hydrogen and the terminal group bonded to the 2-hydroxypropylene radical can be, for example, a

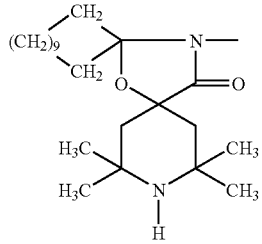

group.

In the compounds of the formula (96-II), the terminal group bonded to the dimethylene radical can be, for example, —OH, and the terminal group bonded to the oxygen can be, for example, hydrogen. The terminal groups can also be polyether radicals.

96-a)

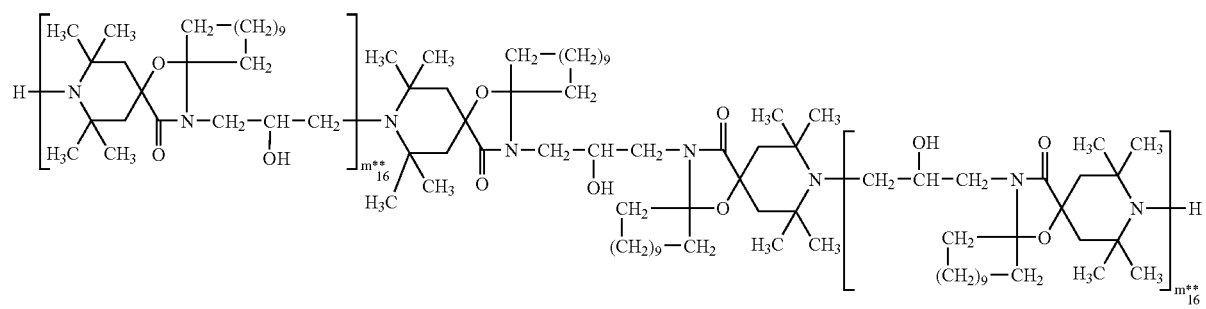

wherein the variables m$_{16}$** are independently of one another as defined for m$_{16}$.

97-1)

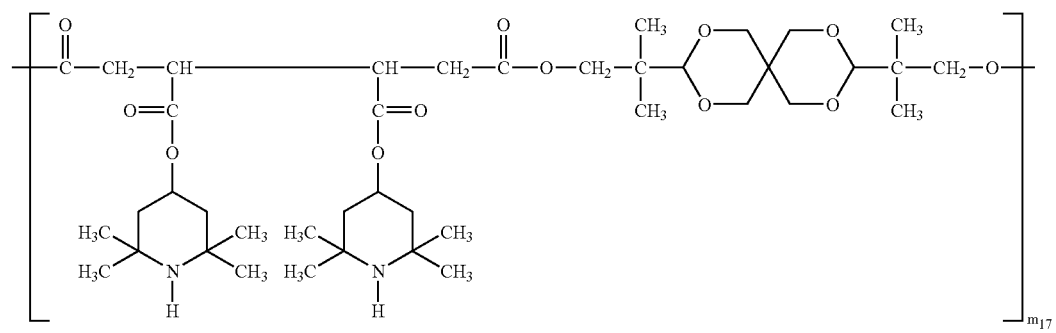

97-2)
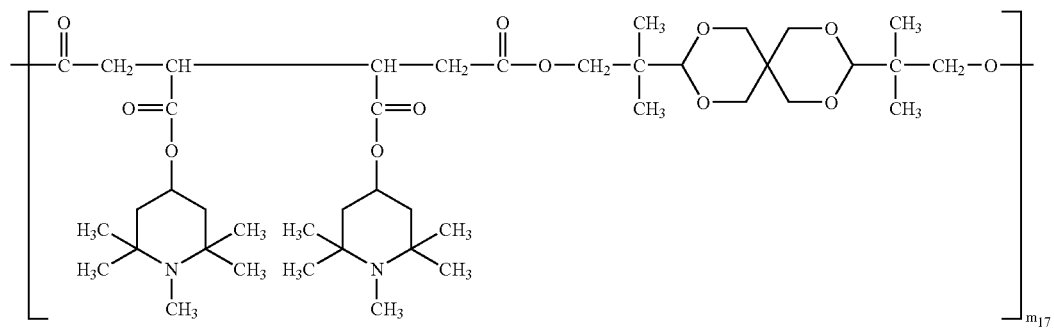
In the compounds (97-1) and (97-2) the mean value of $m_{17}$ is 2.5 and the end group bonded to the >C=O group can be, for example,
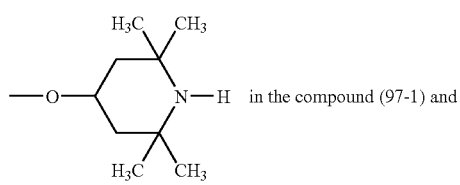 in the compound (97-1) and
-continued
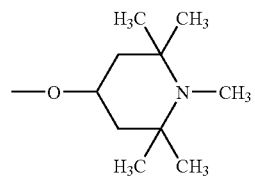 in the compound 97-2); and the end group bonded to the oxygen can be, for example
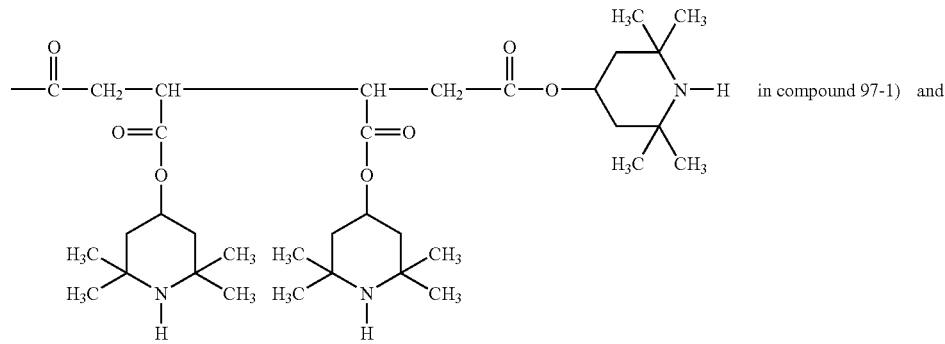 in compound 97-1) and
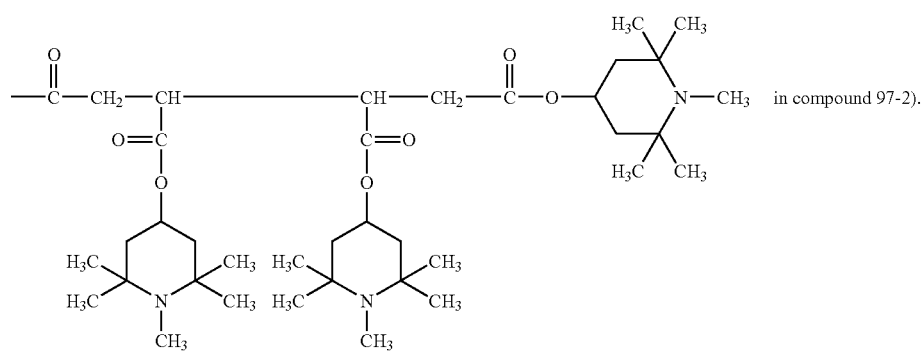 in compound 97-2).

98)

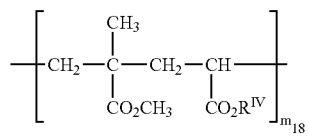

wherein approximately one third of the radicals $R^{IV}$ are —$C_2H_5$ and the others are a group

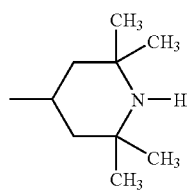

and $m_{18}$ is a number in the range from 2 to 200, preferably 2 to 100, in particular 2 to 50.

In the compound (98), the end group bonded to the —$CH_2$— residue can be, for example, hydrogen and the end group bonded to the —$CH(CO_2R^{IV})$— residue can be, for example,
—CH=CH—COOR$^{IV}$.

99-1)

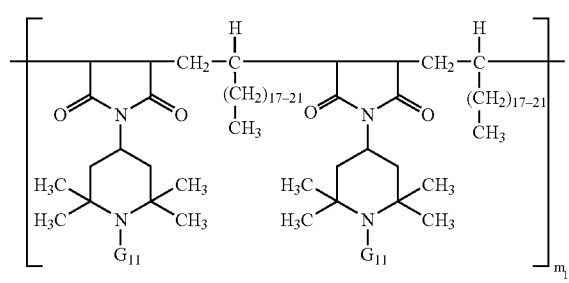

99-2)

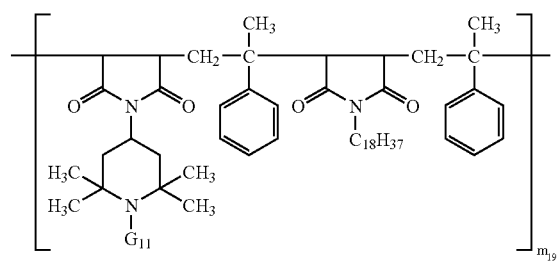

99-3)

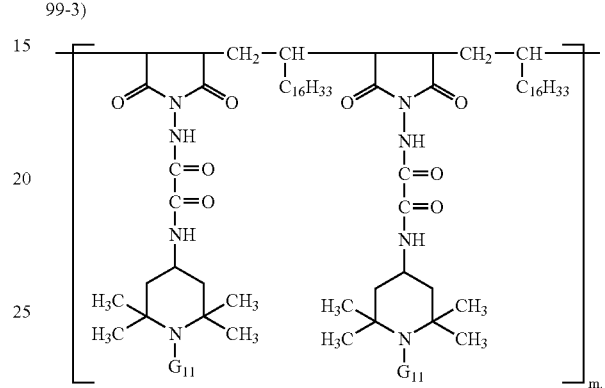

In the compounds (99-1), (99-2) and (99-3), $G_{11}$ is hydrogen or methyl, and $m_{19}$ is a number from 1 to 25.

In the compounds (99-1), (99-2) or (99-3), the end group bonded to the 2,5-dioxopyrrolidine ring can be, for example, hydrogen, and the other end group can be, for example, a group of the formula

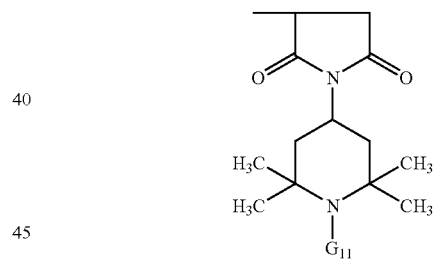

in the compounds (99-1) and (99-2), and
a group of the formula

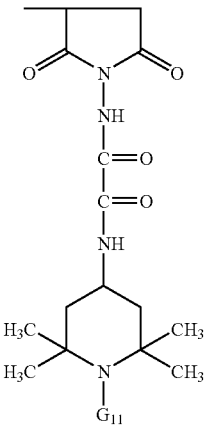

in compound (99-3).

100) A product obtainable by reacting a product, obtained by reaction of a polyamine of the formula (100a) with cyanuric chloride, with a compound of the formula (100b)

(100a)

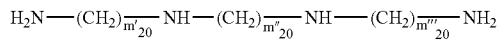

(100b)

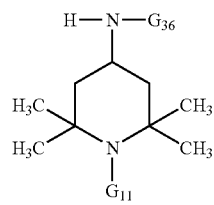

in which $m'_{20}$, $m''_{20}$ and $m'''_{20}$, independently of one another, are a number from 2 to 12, $G_{36}$ is hydrogen, $C_1$-$C_{12}$alkyl, $C_5$-$C_{12}$cycloalkyl, phenyl or $C_7$-$C_9$phenylalkyl, and $G_{11}$ is hydrogen or methyl. The product with $G_{11}$ being hydrogen has the Chemical Abstracts-CAS No. 136 504-96-6.

In general, the above reaction product can be represented for example by a compound of the formula (100-1), (100-2) or (100-3). It can also be in the form of a mixture of these three compounds.

(100-1)

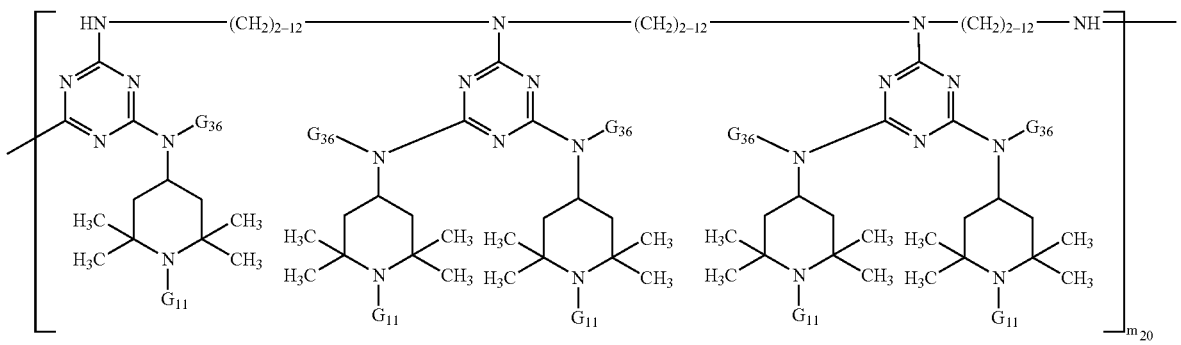

(100-2)

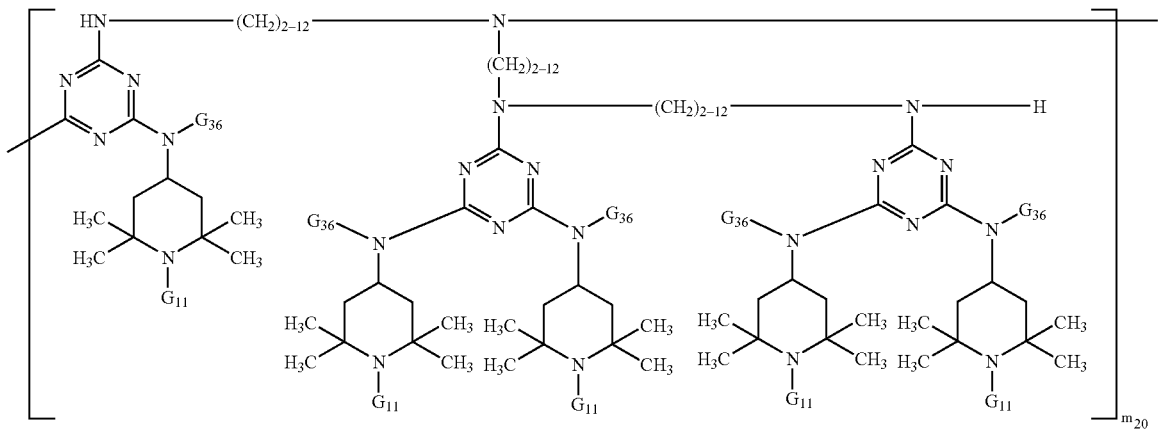

(100-3)
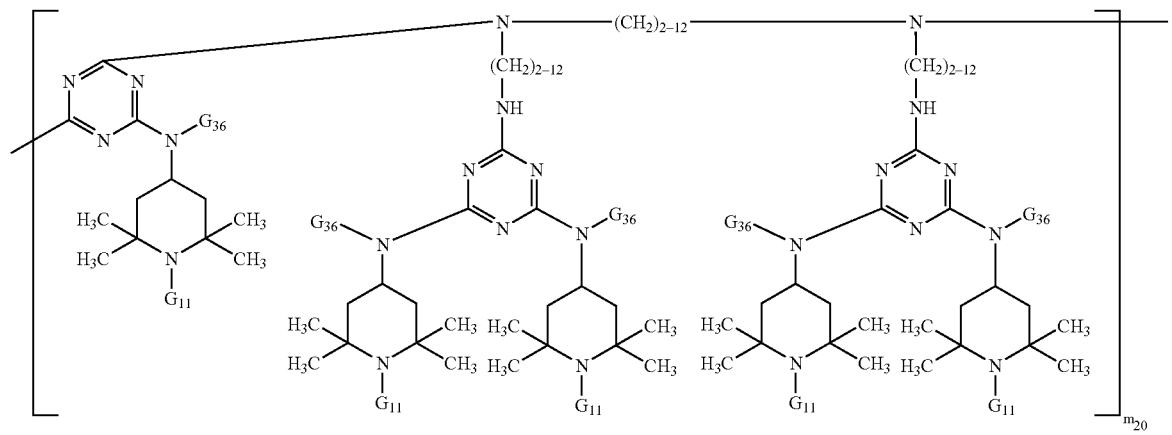
A preferred meaning of the formula (100-1) is
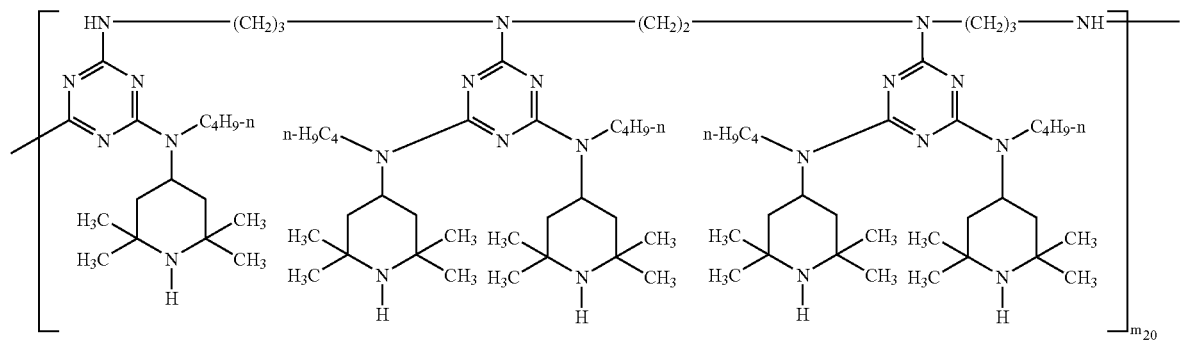
A preferred meaning of the formula (100-2) is
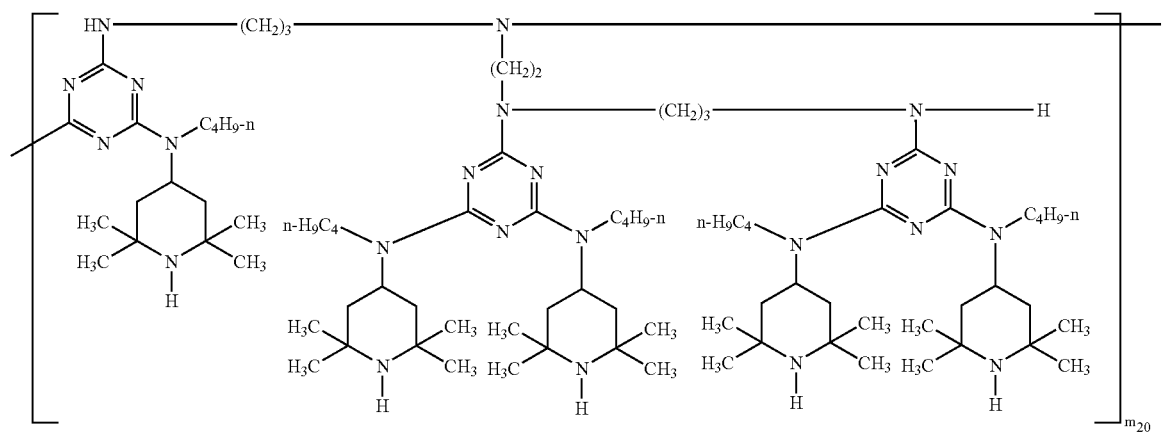

A preferred meaning of the formula (100-3) is

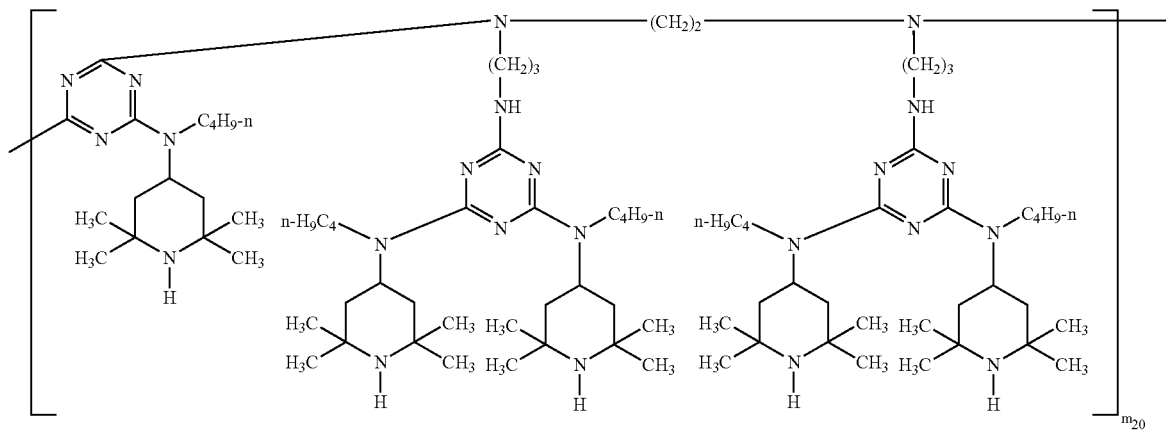

In the above formulae (100-1) to (100-3), $m_{20}$ is e.g. 1 to 20, preferably 2 to 20.

101)

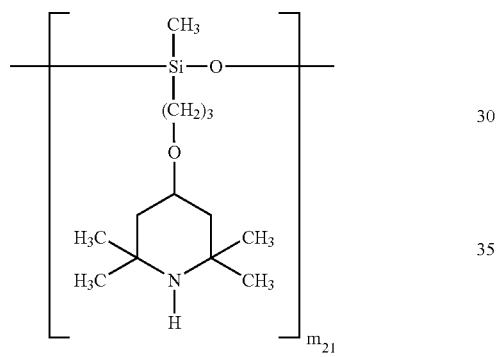

with $m_{21}$ being a number from 1 to 20.

In the compound (101), the terminal group bonded to the silicon atom can be, for example, $(CH_3)_3Si-O-$, and the terminal group bonded to the oxygen can be, for example, $-Si(CH_3)_3$.

The compounds (101) can also be in the form of cyclic compounds if $m_{21}$ is a number from 3 to 10, i.e. the free valences shown in the structural formula then form a direct bond.

102)

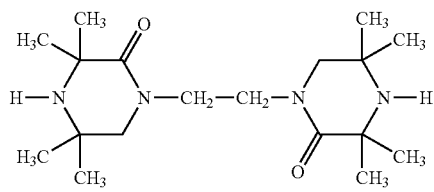

103)

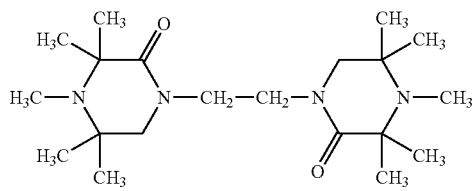

104)
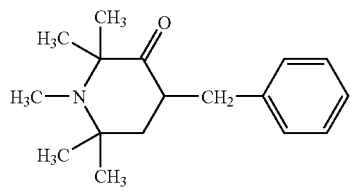
105)
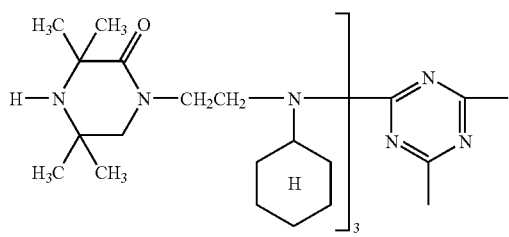
106)
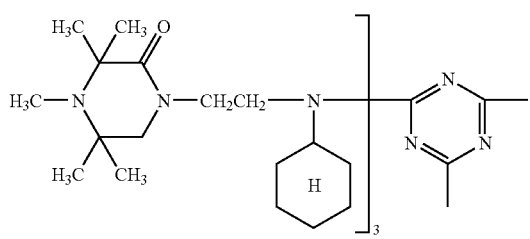
107)
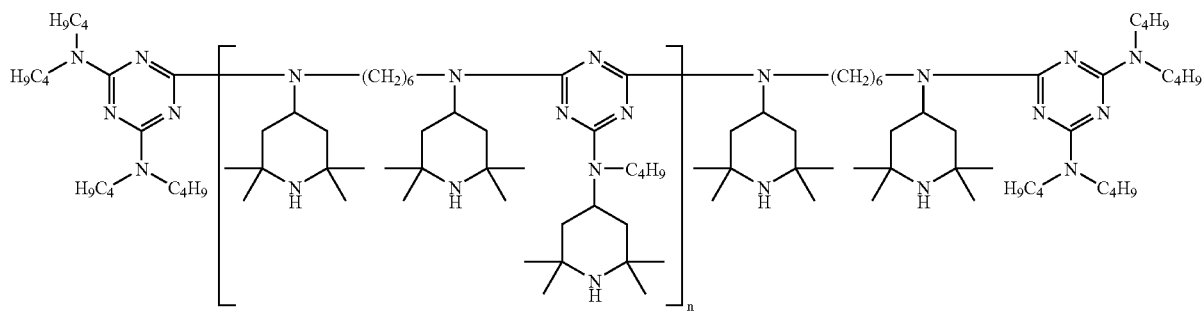
108)
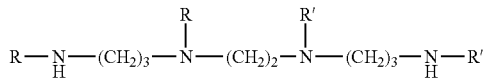
where R is
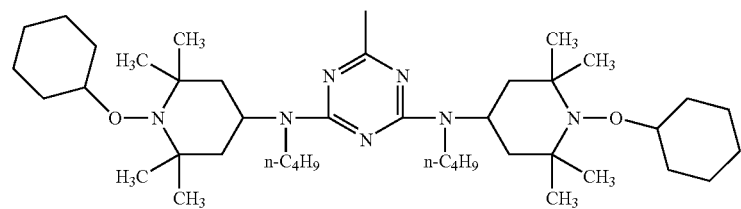

and one of the residues R' is R and the other is H;

109)

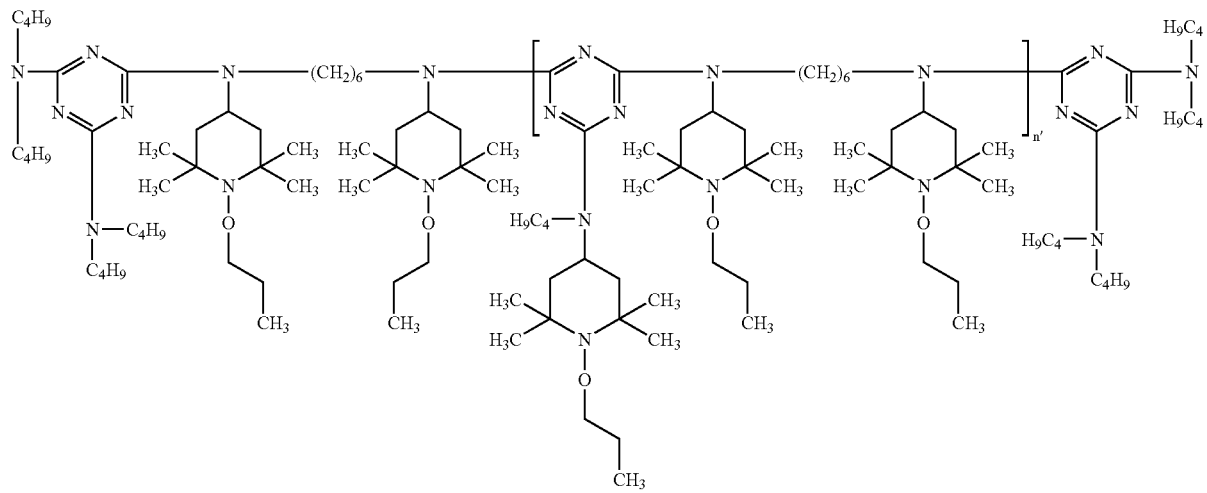

110) 5-(2-ethylhexanoyl)oxymethyl-3,3,5-trimethyl-2-morpholinone as disclosed in example A19 of U.S. Pat. No. 6,140,326;

111)

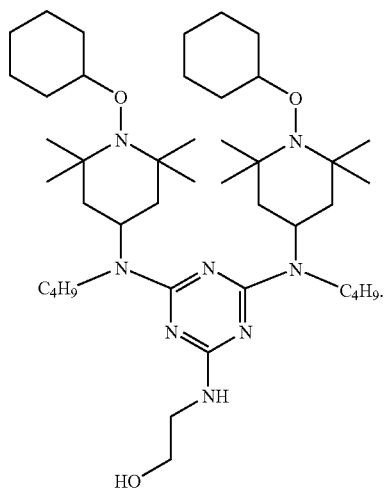

The sterically hindered amine of the above section can also be one of the compounds described in GB-A-2,301,106 as component I-a), I-b), I-c), I-d), I-e), I-f), I-g), I-h), I-i), I-j), I-k) or I-l), in particular the light stabilizer 1-a-1, 1-a-2, 1-b-1, 1-c-1, 1-c-2, 1-d-1, 1-d-2, 1-d-3, 1-e-1, 1-f-1, 1-g-1, 1-g-2 or 1-k-1 listed on pages 68 to 73 of said GB-A-2,301, 106.

The sterically hindered amine of the above section may also be one of the compounds described in EP 782994, for example compounds as described in claims 10 or 38 or in Examples 1-12 or D1 to D-5 therein.

Blends of the present UVA combination with commercially available hindered amines are particularly useful as stabilizers for organic materials, especially polyolefins. For example blends of stabilizer combination comprising a compound of component (A), especially of formula (A2) besides component (B) with each of the following:

| | | |
|---|---|---|
| TINUVIN ® 770 | TINUVIN ® 123 | TINUVIN ® 765 |
| TINUVIN ® 440 | TINUVIN ® 144 | CHIMASSORB ® 966 |
| DASTIB ® 845 | DIACETAM ® 5 | GOODRITE ® UV 3034 |
| GOODRITE ® UV 3150 | GOODRITE ® UV 3159 | CYASORB ® UV 3581 |
| CYASORB ® UV 3604 | HOSTAVIN ® N 20 | HOSTAVIN ® N 24 |
| MARK ® LA 52 | MARK ® LA 57 | MARK ® LA 62 |
| MARK ® LA 67 | SUMISORB ® TM 61 | UVINUL ® 4049 |
| UVINUL ® 4050 H | SANDUVOR ® 3050 | SANDUVOR ® PR-31 |
| UVASIL ® 299 LM | UVASIL ® 2000 LM | TINUVIN ® 622 |
| CHIMASSORB ® 944 | CHIMASSORB ® 119 | CYASORB ® UV 3346 |
| CYASORB ® UV 3529 | DASTIB ® 1082 | FERRO ® AM 806 |

| -continued | | |
|---|---|---|
| LUCHEM ® HA-B18 | HOSTAVIN ® N 30 | MARK ® LA 63 |
| MARK ® LA 68 | UVINUL ® 5050 H | UVASIL ® 299 HM |
| UVASIL ® 2000 HM | UVASORB ® HA 88 | CHIMASSORB ® 2020 |
| LICHTSCHUTZSTOFF ® UV 31 | | |

Particularly preferred are the mixtures with TINUVIN® 770, CYASORB® UV 3581, HOSTAVIN® N 20, MARK® LA 57, UVINUL® 4050 H, SANDUVOR® 3050, UVASIL® 299 LM, UVASIL® 2000 LM, TINUVIN® 622, CHIMASSORB® 944, CYASORB® UV 3346, HOSTAVIN® N 30, UVASIL® 299 HM, UVASIL® 2000 HM, UVASORB® HA 88 and CHIMASSORB® 2020.

Furthermore useful are sterically hindered amines substituted on the N-atom by a hydroxy-substituted alkoxy group, for example compounds such as 1-(2-hydroxy-2-methylpropoxy)-4-octadecanoyloxy-2,2,6,6-tetramethylpiperidine, 1-(2-hydroxy-2-methylpropoxy)-4-hydroxy-2,2,6,6-tetramethylpiperidine, 1-(2-hydroxy-2-methylpropoxy)-4-oxo-2,2,6,6-tetramethylpiperidine, bis(1-(2-hydroxy-2-methylpropoxy)-2,2,6,6-tetramethyl piperidin-4-yl)sebacate, bis(1-(2-hydroxy-2-methylpropoxy)-2,2,6,6-tetramethylpiperidin-4-yl)adipate, bis(1-(2-hydroxy-2-methylpropoxy)-2,2,6,6-tetramethylpiperidin-4-yl)succinate, bis(1-(2-hydroxy-2-methylpropoxy)-2,2,6,6-tetramethylpiperidin-4-yl)glutarate and 2,4-bis{N-[1-(2-hydroxy-2-methylpropoxy)-2,2,6,6-tetramethylpiperidin-4-yl]-N-butylamino}-6-(2-hydroxyethylamino)-s-triazine. Preferred is 112) 1-(2-hydroxy-2-methylpropoxy)-4-octadecanoyloxy-2,2,6,6-tetramethylpiperidine of formula

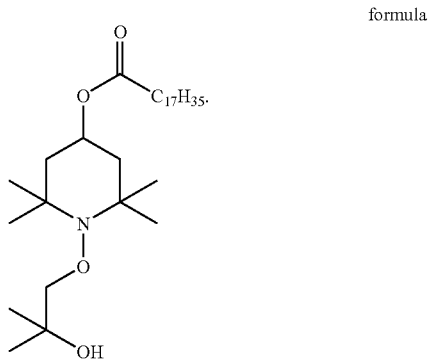

Stabilization of Organic Material

The invention also pertains to (a) an organic material, which comprises (b) as stabilizer against deleterious effects of light, oxygen and/or heat, or as UV filtering agent, the combination of UV absorbing components (A) and (B) described above.

Preferably, the organic material of component (a) is a natural, semi-synthetic or synthetic polymer, especially a thermoplastic polymer, a crosslinkable binder of a coating composition, the crosslinked coating, a dye or printing ink or a color photographic material.

Most preferably, the thermoplastic polymer is a polyolefin, for example, polyethylene, polypropylene, a styrene copolymer, polycarbonate, polymethylmethacrylate, a polyester, a polyamide, an adhesive, a halogenated polymer such as polyvinylchloride, a thermoplastic polyolefin useful in automotive coatings and applications or a urethane based automotive coating.

In a composition of specific interest, present component (a) is selected from thermoplastic polymers, and component (b) is a combination of compound (A2) with a compound (B) selected from the compounds i-x, xii, xiii, xix-xxiii, xxv-xxvii, xxx-xxxvi, and xl-xlv; especially i, ii, iii, v, vi, viii, xii, xiii, xix, xx, xxii, xxiii, xxvi, xxx, xxxi, xxxiv, xxxvi, xl, xli, xlii, xliii, xliv, xlv.

In another composition of specific interest, present component (a) is selected from a crosslinkable binder of a coating composition, a crosslinked coating, a dye or printing ink or a color photographic material, and component (b) is a combination of compound (A1) or (A2), especially compound (A1), with a compound (B) selected from the compounds i-iv, vi-xi, xiii-xviii, xxiii-xxxix; especially ii, iii, iv, vi, vii, viii, xx, xxv, xxxvii; in particular those of the benzotriazole class.

In a specific embodiment, component (a) is a film forming binder of a coating composition on a metal substrate and (B) of component (b) is selected from the compounds ii, iii, iv, vi, vii, viii, xx, xxv, xxxvii.

In another specific embodiment, component (a) is a film forming binder of a coating composition on wood substrate and (B) of component (b) is selected from the compounds i, viii, xiv, xx.

In another specific embodiment, component (a) is a synthetic thermoplastic organic polymer containing heteroatoms in the main chain, especially a polycarbonate, polyester or polyamide, and (B) of component (b) is selected from the compounds iii, v, vi, vii, xii, xix, xxii, xxiii, xxvi, xxvii, xxx, xxxi, xl, xlii, xliii, xliv.

In another specific embodiment, component (a) is a synthetic thermoplastic organic polymer containing only carbon atoms in the main chain, especially a polyolefin, and (B) of component (b) is selected from the compounds i, ii, viii, xii, xiii, xx, xxii, xxiii, xxvi, xxvii, xxx, xxxi, xxxiv, xxxvi, xlv.

In another specific embodiment, component (a) is a reprographic material, especially a colour photographic material or a printing ink, and (B) of component (b) is selected from the compounds i, vii, xi, xii, xiii, xiv, xv, xx, xxv, xxxvii.

In another specific embodiment, component (a) is a film forming binder of a coating composition on a metal substrate, which composition contains as additional stabilizer a sterically hindered amine selected from the compounds 13, 14a, 24, 110 and/or 112.

In another specific embodiment, component (a) is a film forming binder of a coating composition or a stain on wood substrate, which composition contains as additional stabilizer a sterically hindered amine selected from the compounds 13, 14a, 24, 110, 112 and/or 1-oxyl-2,2,6,6-tetramethyl-4-hydroxypiperidin.

In another specific embodiment, component (a) is a synthetic thermoplastic organic polymer containing only carbon atoms in the main chain, especially polyethylene, polypropylene, or blends or copolymers thereof, which composition contains as additional stabilizer a sterically hindered amine selected from the compounds 13, 76, 81, 84-1, 92-1, 92-2, 107, 108, 109 and/or 112.

The present compounds of component (b) exhibit superior hydrolytic stability, handling and storage stability as well as good resistance to extractability when present in a stabilized composition.

In general polymers which can be stabilized include:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerization (normally under high pressure and at elevated temperature).

b) catalytic polymerization using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either p- or s-coordinated. These metal complexes may be in the free form or fixed on substrates, typically on activated magnesium chloride, titanium(III) chloride, alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidenenorbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylenel-carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

5. Polystyrene, poly(p-methylstyrene), poly(alpha-methylstyrene).

6. Copolymers of styrene or alpha-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or alpha-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from alpha,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bis-glycidyl ethers.
13. Polyacetals such as polyoxymethylene and those polyoxymethylenes which contain ethylene oxide as a comonomer; polyacetals modified with thermoplastic polyurethanes, acrylates or MBS.
14. Polyphenylene oxides and sulfides, and mixtures of polyphenylene oxides with styrene polymers or polyamides.
15. Polyurethanes derived from hydroxyl-terminated polyethers, polyesters or polybutadienes on the one hand and aliphatic or aromatic polyisocyanates on the other, as well as precursors thereof.
16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexa-methylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).
17. Polyureas, polyimides, polyamide-imides and polybenzimidazoles.
18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.
19. Polycarbonates and polyester carbonates.
20. Polysulfones, polyether sulfones and polyether ketones.
21. Crosslinked polymers derived from aldehydes on the one hand and phenols, ureas and melamines on the other hand, such as phenolformaldehyde resins, urea/formaldehyde resins and melamine/formaldehyde resins.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, polyisocyanates or epoxy resins.
26. Crosslinked epoxy resins derived from polyepoxides, for example from bis glycidyl ethers or from cycloaliphatic diepoxides.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxy-lated styrene/butadiene copolymers.
31. Polysiloxanes such as the soft, hydrophilic polysiloxanes described, for example, in U.S. Pat. No. 4,259,467; and the hard polyorganosiloxanes described, for example, in U.S. Pat. No. 4,355,147.
32. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
33. Radiation curable compositions containing ethylenically unsaturated monomers or oligomers and a polyunsaturated aliphatic oligomer.
34. Epoxymelamine resins such as light-stable epoxy resins crosslinked by an epoxy functional coetherified high solids melamine resin such as LSE-4103 (Monsanto).

The stabilizers of component (b) and optional further stabilizers may be added to the material to be stabilized of component (a), e.g. the polyolefin, individually or mixed with one another. If desired, the individual components of a stabilizer mixture can be mixed with one another in the melt (melt blending) before incorporation into the material to be stabilized.

The additives of the invention (present component (b)) and optional further components may be added to the polymer material individually or mixed with one another. If desired, the individual components can be mixed with one another before incorporation into the polymer for example by dry blending, compaction or in the melt.

The incorporation of the additives of the invention and optional further components into the polymer is carried out by known methods such as dry blending in the form of a powder, or wet mixing in the form of solutions, dispersions or suspensions for example in an inert solvent, water or oil. The additives of the invention and optional further additives may be incorporated, for example, before or after molding or also by applying the dissolved or dispersed additve or additive mixture to the polymer material, with or without subsequent evaporation of the solvent or the suspension/dispersion agent. They may be added directly into the processing apparatus (e.g. extruders, internal mixers, etc), e.g. as a dry mixture or powder or as solution or dispersion or suspension or melt.

The incorporation can be carried out in any heatable container equipped with a stirrer, e.g. in a closed apparatus such as a kneader, mixer or stirred vessel. The incorporation is preferably carried out in an extruder or in a kneader. It is immaterial whether processing takes place in an inert atmosphere or in the presence of oxygen.

The addition of the additive or additive blend to the polymer can be carried out in all customary mixing machines in which the polymer is melted and mixed with the additives. Suitable machines are known to those skilled in the art. They are predominantly mixers, kneaders and extruders.

The process is preferably carried out in an extruder by introducing the additive during processing.

Particularly preferred processing machines are single-screw extruders, contrarotating and corotating twin-screw extruders, planetary-gear extruders, ring extruders or cokneaders. It is also possible to use processing machines provided with at least one gas removal compartment to which a vacuum can be applied.

Suitable extruders and kneaders are described, for example, in *Handbuch der Kunststoffextrusion*, Vol. 1 Grundlagen, Editors F. Hensen, W. Knappe, H. Potente, 1989, pp. 3-7, ISBN: 3-446-14339-4 (Vol. 2 Extrusionsanlagen 1986, ISBN 3-446-14329-7).

For example, the screw length is 1-60 screw diameters, preferably 35-48 screw diameters. The rotational speed of the screw is preferably 10-600 rotations per minute (rpm), very particularly preferably 25-300 rpm.

The maximum throughput is dependent on the screw diameter, the rotational speed and the driving force. The process of the present invention can also be carried out at a level lower than maximum throughput by varying the parameters mentioned or employing weighing machines delivering dosage amounts.

If a plurality of components are added, these can be premixed or added individually.

The additives of the invention and optional further additives can also be sprayed onto the polymer material. They are able to dilute other additives (for example the conventional additives indicated above) or their melts so that they can be sprayed also together with these additives onto the material. Addition by spraying during the deactivation of the polymerization catalysts is particularly advantageous; in this case, the steam evolved may be used for deactivation of the catalyst. In the case of spherically polymerized polyolefins it may, for example, be advantageous to apply the additives of the invention, optionally together with other additives, by spraying.

The additives of the invention and optional further additives can also be added to the polymer in the form of a masterbatch ("concentrate") which contains the components in a concentration of, for example, about 1% to about 40% and preferably 2% to about 20% by weight incorporated in a polymer. The polymer must not be necessarily of identical structure than the polymer where the additives are added finally. In such operations, the polymer can be used in the form of powder, granules, solutions, suspensions or in the form of latices.

Incorporation can take place prior to or during the shaping operation, or by applying the dissolved or dispersed compound to the polymer, with or without subsequent evaporation of the solvent. In the case of elastomers, these can also be stabilized as latices. A further possibility for incorporating the additives of the invention into polymers is to add them before, during or directly after the polymerization of the corresponding monomers or prior to crosslinking. In this context the additive of the invention can be added as it is or else in encapsulated form (for example in waxes, oils or polymers).

The materials containing the additives of the invention described herein can be used for the production of moldings, rotomolded articles, injection molded articles, blow molded articles, films, tapes, mono-filaments, fibers, nonwovens, profiles, adhesives or putties, surface coatings and the like.

The compositions comprising the UV absorber combination of present invention and optional further additives are useful for many applications including the following:

| | |
|---|---|
| Thermoplastic olefins | Paintable thermoplastic olefins |
| Polypropylene molded articles | Polypropylene fiber |
| Polyethylene film | Polyethylene film for greenhouse |
| Polyethylene agricultural mulch film | Polypropylene fiber with brominated flame retardants |
| Molded polypropylene with brominated flame retardants | Molded thermoplastic olefin with brominated flame retardants |
| Polethylene film with brominated flame retardants | Thermoplastic elastomers with other costabilizers |
| Grease-filled wire and cable insulation | Gamma-irradiated polyolefins |
| Coatings over plastic substrates | Polycarbonate blends, e.g. PC/ABS, PC/PA |
| Polyolefin tanks or containers containing chemicals | Polyethylene gas pipes |
| Polypropylene non-woven fabric for agricultural applications, e.g. shade cloth | Polyolefin films with an antifog agent |
| Polyolefin films with an antistatic agent | Polyolefin films with IR thermal fillers such as hydrotalcites, e.g. DHT4A |
| Polypropylene tape or slit film | Polypropylene non-woven fabrics |
| Polyethylene non-woven fabrics | Flame-resistant molded polypropylene articles |
| Flame-resistant polypropylene fiber | Flame-resistant molded thermoplastic olefins |
| Flame-resistant polethylene film | Two-component polyester urethane coatings |
| Automotive coatings | |
| Two-component acrylic urethane coatings | Water-borne wood varnishes |
| Pigmented Automotive OEM coatings | High solids acid catalyzed thermoset acrylic resin enamels |

| | |
|---|---|
| White polyester/melamine based oil-free alkyd coil coatings | Tung oil phenolic varnishes |
| Aromatic urethane varnishes | Acrylic alkyd refinish enamels |
| Medium oil alkyd enamels | Electrocoat compositions |
| Abrasion resistant coating compositions | Coatings over polycarbonate |
| Chromogenic photographic layers | Glycidyl methacrylate-based powder clearcoats |
| Oil modified urethane alkyds for wood applications | Pre-formed films for lamination to plastic substrates |
| Polyolefin articles in contact with chlorinated water, e.g. polyethylene or polypropylene pressure pipes, optionally containing acid scavengers and/or benzofuranones | |

The materials containing the stabilizer mixtures described herein can be used for the production of moldings, roto-molded articles, injection molded articles, blow molded articles, films, tapes, mono-filaments, fibers, surface coatings and the like.

Likewise of particular interest is the use of the present compounds as stabilizers for coatings, for example for paints. The invention therefore also relates to those compositions whose component (a) is a film-forming binder for coatings and component (b) is the stabilizer of present invention.

The use of the novel stabilizer in coatings is accompanied by the additional advantage that it prevents delamination, i.e. the flaking-off of the coating from the substrate. This advantage is particularly important in the case of metallic substrates, including multilayer systems on metallic substrates. Substrates to be coated include wood, ceramic materials, metals, plastics, or articles coated or stained with organic materials.

The binder (component (a)) can in principle be any binder which is customary in industry, for example those described in Ullmann's Encyclopedia of Industrial Chemistry, 5th Edition, Vol. A18, pp. 368-426, VCH, Weinheim 1991. In general, it is a film-forming binder based on a thermoplastic or thermosetting resin, predominantly on a thermosetting resin. Examples thereof are alkyd, acrylic, polyester, phenolic, melamine, epoxy and polyurethane resins and mixtures thereof.

Component (a) can be a cold-curable or hot-curable binder; the addition of a curing catalyst may be advantageous. Suitable catalysts which accelerate curing of the binder are described, for example, in Ullmann's Encyclopedia of Industrial Chemistry, Vol. A18, p. 469, VCH Verlagsgesellschaft, Weinheim 1991.

Preference is given to coating compositions in which component (a) is a binder comprising a functional acrylate resin and a crosslinking agent.

Examples of coating compositions containing specific binders are:

1. paints based on cold- or hot-crosslinkable alkyd, acrylate, polyester, epoxy or melamine resins or mixtures of such resins, if desired with addition of a curing catalyst;
2. two-component polyurethane paints based on hydroxyl-containing acrylate, polyester or polyether resins and aliphatic or aromatic isocyanates, isocyanurates or polyisocyanates;
3. two-component polyurethane paints based on thiol-containing acrylate, polyester or polyether resins and aliphatic or aromatic isocyanates, isocyanurates or polyisocyanates;
4. one-component polyurethane paints based on blocked isocyanates, isocyanurates or polyisocyanates which are deblocked during baking, if desired with addition of a melamine resin;
5. one-component polyurethane paints based on aliphatic or aromatic urethanes or polyurethanes and hydroxyl-containing acrylate, polyester or polyether resins;
6. one-component polyurethane paints based on aliphatic or aromatic urethaneacrylates or polyurethaneacrylates having free amino groups within the urethane structure and melamine resins or polyether resins, if necessary with curing catalyst;
7. two-component paints based on (poly)ketimines and aliphatic or aromatic isocyanates, isocyanurates or polyisocyanates;
8. two-component paints based on (poly)ketimines and an unsaturated acrylate resin or a polyacetoacetate resin or a methacrylamidoglycolate methyl ester;
9. two-component paints based on carboxyl- or amino-containing polyacrylates and polyepoxides;
10. two-component paints based on acrylate resins containing anhydride groups and on a polyhydroxy or polyamino component;
11. two-component paints based on acrylate-containing anhydrides and polyepoxides;
12. two-component paints based on (poly)oxazolines and acrylate resins containing anhydride groups, or unsaturated acrylate resins, or aliphatic or aromatic isocyanates, isocyanurates or polyisocyanates;
13. two-component paints based on unsaturated polyacrylates and polymalonates;
14. thermoplastic polyacrylate paints based on thermoplastic acrylate resins or externally crosslinking acrylate resins in combination with etherified melamine resins;
15. paint systems based on siloxane-modified or fluorine-modified acrylate resins;
16. paint systems, especially for clearcoats, based on malonate-blocked isocyanates with melamine resins (e.g. hexamethoxymethylmelamine) as crosslinker (acid catalyzed);
17. UV-curable systems based on oligomeric urethane acrylates and/or acrylatacrylaten, if desired in combination with other oligomers or monomers;
18. dual cure systems, which are cured first by heat and subsequently by UV or electron irradiation, or vice versa, and whose components contain ethylenic double bonds capable to react on irradiation with UV light in presence of a photoinitiator or with an electron beam.

Coating systems based on siloxanes are also possible, e.g. systems described in WO 98/56852, WO 98/56853, DE-A-2914427, or DE-A-4338361.

In addition to components (a) and (b), the coating composition according to the invention preferably comprises as component (C) a light stabilizer of the sterically hindered amine type, for example as mentioned in the above list. Further examples for light stabilizers of the 2-(2-hydroxyphenyl)-1,3,5-triazine type advantageously to be added can be found e.g. in the publications U.S. Pat. No. 4,619,956, EP-A-434608, U.S. Pat. No. 5,198,498, U.S. Pat. No. 5,322,868, U.S. Pat. No. 5,369,140, U.S. Pat. No. 5,298,067, WO-94/18278, EP-A-704437, GB-A-2297091, WO-96/28431.

To achieve maximum light stability, it is of particular interest to add sterically hindered amines as set out in the abovementioned list. The invention therefore also relates to a coating composition which in addition to components (a) and (b) comprises as component (c) a light stabilizer of the sterically hindered amine type.

This stabilizer is preferably a 2,2,6,6-tetraalkylpiperidine derivative or a 3,3,5,5-tetraalkyl-morpholin-2-one derivative containing at least one group of the formula

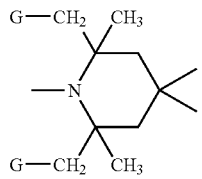 and/or 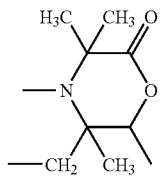

in which G is hydrogen or methyl, especially hydrogen.

Component (C) is preferably used in an amount of 0.05-5 parts by weight per 100 parts by weight of the solid binder.

Examples of tetraalkylpiperidine derivatives which can be used as component (C) are given in EP-A-356 677, pages 3-17, sections a) to f). These sections of this EP-A are regarded as part of the present description. It is particular expedient to employ the following tetraalkylpiperidine derivatives:

bis(2,2,6,6-tetramethylpiperid-4-yl)succinate, bis(2,2,6,6-tetramethylpiperid-4-yl)sebacate, bis(1,2,2,6,6-pentamethylpiperid-4-yl)sebacate, di(1,2,2,6,6-pentamethylpiperid-4-yl)butyl-(3,5-di-tert-butyl-4-hydroxybenzyl)malonate, bis(1-octyloxy-2,2,6,6-tetramethylpiperid-4-yl)sebacate, tetra(2,2,6,6-tetramethylpiperid-4-yl)butane-1,2,3,4-tetracarboxylate, tetra(1,2,2,6,6-pentamethylpiperid-4-yl)butane-1,2,3,4-tetracarboxylate, 2,2,4,4-tetramethyl-7-oxa-3,20-diaza-21-oxo-dispiro[5.1.11.2]heneicosane, 8-acetyl-3-dodecyl-1,3,8-triaza-7,7,9,9-tetramethylspiro[4.5]decane-2,4-dione, 1,1-bis-(1,2,2,6,6-pentamethylpiperidine-4-yl-oxycarbonyl)-2-(4-methoxyphenyl)-ethene, or a compound of the formulae

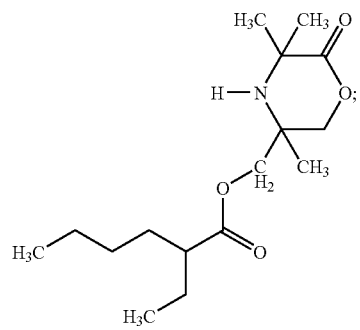

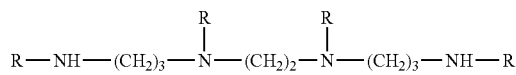

where R =

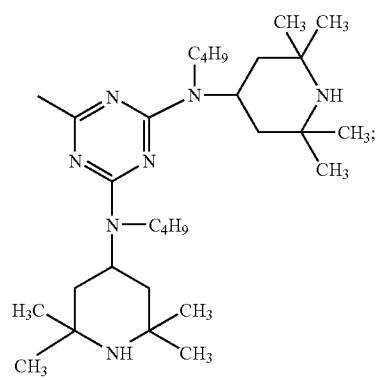

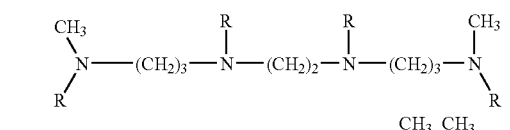

where R =

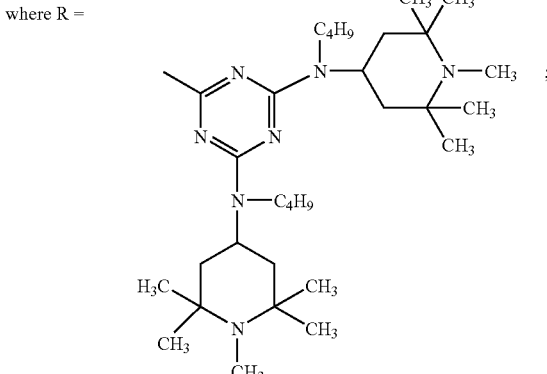

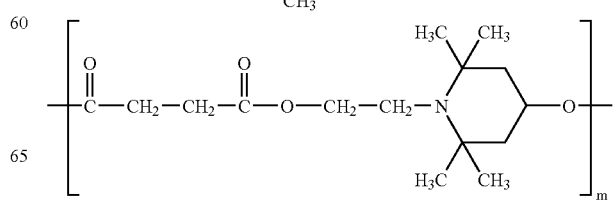

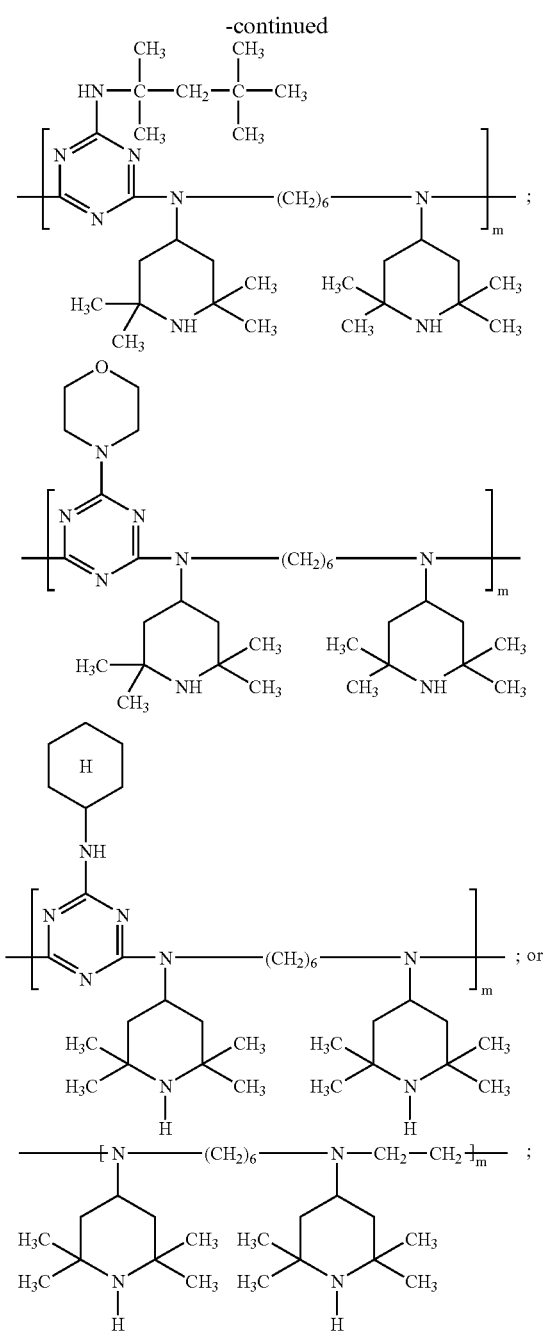

in which m is 5-50.

Apart from components (a), (b) and, if used, (C), the coating composition can also comprise further components, examples being solvents, pigments, dyes, plasticizers, stabilizers, rheologic or thixotropic agents, drying catalysts and/or levelling agents. Examples of possible components are described in Ullmann's Encyclopedia of Industrial Chemistry, 5th Edition, Vol. A18, pp. 429-471, VCH, Weinheim 1991.

Possible drying catalysts or curing catalysts are, for example, free (organic) acids or bases, or (organic) blocked acids or bases which may be deblocked by thermal treatment or irradiation, organometallic compounds, amines, amino-containing resins and/or phosphines. Examples of organo-metallic compounds are metal carboxylates, especially those of the metals Pb, Mn, Co, Zn, Zr or Cu, or metal chelates, especially those of the metals Al, Ti, Zr or Hf, or organo-metallic compounds such as organotin compounds.

Examples of metal carboxylates are the stearates of Pb, Mn or Zn, the octoates of Co, Zn or Cu, the naphthenates of Mn and Co or the corresponding linoleates, resinates or tallates.

Examples of metal chelates are the aluminium, titanium or zirconium chelates of acetylacetone, ethyl acetylacetate, salicylaldehyde, salicylaldoxime, o-hydroxyacetophenone or ethyl trifluoroacetylacetate, and the alkoxides of these metals.

Examples of organotin compounds are dibutyltin oxide, dibutyltin dilaurate or dibutyltin dioctoate.

Examples of amines are, in particular, tertiary amines, for example tributylamine, triethanolamine, N-methyldiethanolamine, N-dimethylethanolamine, N-ethylmorpholine, N-methylmorpholine or diazabicyclooctane(triethylenediamine), diazabicycloundecene, DBN (=1,5-diazabicyclo [4.3.0]non-5-ene), and salts thereof. Further examples are quaternary ammonium salts, for example trimethylbenzylammonium chloride.

Amino-containing resins are simultaneously binder and curing catalyst. Examples thereof are amino-containing acrylate copolymers.

The curing catalyst used can also be a phosphine, for example triphenylphosphine.

The novel coating compositions can also be radiation-curable coating compositions. In this case, the binder essentially comprises monomeric or oligomeric compounds containing ethylenically unsaturated bonds (prepolymers), which after application are cured by actinic radiation, i.e. converted into a crosslinked, high molecular weight form. Where the system is UV-curing, it generally contains at least one photoinitiator as well. Corresponding systems are described in the abovementioned publication Ullmann's Encyclopedia of Industrial Chemistry, 5th Edition, Vol. A18, pages 451-453. In radiation-curable coating compositions, the novel stabilizers can also be employed without the addition of sterically hindered amines.

The coating compositions according to the invention can be applied to any desired substrates, for example to metal, wood, plastic or ceramic materials. They are preferably used as topcoat in the finishing of automobiles. If the topcoat comprises two layers, of which the lower layer is pigmented and the upper layer is not pigmented, the novel coating composition can be used for either the upper or the lower layer or for both layers, but preferably for the upper layer.

The novel coating compositions can be applied to the substrates by the customary methods, for example by brushing, spraying, pouring, dipping or electrophoresis; see also Ullmann's Encyclopedia of Industrial Chemistry, 5th Edition, Vol. A18, pp. 491-500.

Depending on the binder system, the coatings can be cured at room temperature or by heating. The coatings are preferably cured at 50-150° C., and in the case of powder coatings or coil coatings even at higher temperatures.

The coatings obtained in accordance with the invention have excellent resistance to the damaging effects of light, oxygen and heat; particular mention should be made of the good light stability and weathering resistance of the coatings thus obtained, for example paints.

The coating compositions can comprise an organic solvent or solvent mixture in which the binder is soluble. The coating composition can otherwise be an aqueous solution or dispersion. The vehicle can also be a mixture of organic solvent and water. The coating composition may be a high-solids paint or can be solvent-free (e.g. a powder coating material). Powder coatings are, for example, those described in Ullmann's Encyclopedia of Industrial Chemistry, 5th Ed., A18, pages 438-444. The powder coating material may also have the form of a powder-slurry (dispersion of the powder preferably in water).

The pigments can be inorganic, organic or metallic pigments. The novel coating compositions preferably contain no pigments and are used as a clearcoat.

Likewise preferred is the use of the coating composition as a topcoat for applications in the automobile industry, especially as a pigmented or unpigmented topcoat of the paint finish. Its use for underlying coats, however, is also possible.

Addition of the present stabilizer to a pigmented coating may also protect the pigment from damaging effects of UV radiation, especially in the case of liquid crystal pigments.

For the preparation of thin UV absorbing layers, the present stabilizers may also be applied on the substrate using plasma deposition. Methods of obtaining a plasma under vacuum conditions has been widely described in the literature, with inductive or capacitive coupling of electrical energy. Direct (DC) or alternating current (AC) may be used with frequencies ranging from the low kHz to the MHz and even microwave (GHz) range.

Preferres substrates are selected from metals, semiconductors, glass, quartz or thermoplastic, crosslinked or structurally crosslinked plastics.

Preferred semiconductor is silicon, e.g. in the form of wavers.

Metals are preferably aluminum, chromium, steel, vanadium, as used for manufacturing of high precision reflectors such as telescope mirrors or beam reflectors. Especially preferred is aluminum.

Primary plasma gas can be, for example, He, Ar, Xe, $N_2$, $O_2$ or air, preferred are inert gases such as He, argon or xenon. When vaporized, the stabilizers mix with the plasma gas and are likewise ionized.

In general, the deposition process is not sensitive in respect of gas added or type of energy coupling.

Relatively low pressure is important. Preferably, the pressure ranges from $10^{-6}$ mbar to $10^{-2}$ mbar, especially from $10^{-3}$ to $10^{-4}$ mbar.

The material may be deposited on a plasma electrode and evaporated right away. Preferably, the material to be evaporated is located on a plate or in a crucible which may be heated separately, outside the range of the plasma discharge. Cricible or plate may be on positive or negative electric potential related to the plasma.

Some embodiments of plasma generation and deposition have been described, for example, by A. T. Bell, "Fundamentals of Plasma Chemistry" in "Technology and Application of Plasma Chemistry", ed. by J. R. Holahan and A. T. Bell, Wiley, New York (1974); or by H. Suhr, Plasma Chem. Plasma Process 3(1), 1, (1983).

The temperature for evaporating the stabilizers is preferably 20° C. to 350° C., especially 100° C. to 250° C.

This process is especially suitable for the deposition of thin layers. Preferably, the layer thickness obtained by plasma deposition is from 10 nm to 1000 nm, more preferably from 50 nm to 500 nm, and especially preferred from 100 nm to 300 nm.

The present UV absorber combination may also be used in reprographic materials or recording materials, such as films, papers, paper coatings or printing inks. Application in reprographic paper or printing substrates is, for example, as described in EP-A-1308308, especially sections [0010], [0017] and examples therein, or U.S. Pat. No. 5,073,448, see especially column 6, line 53, until column 10, line 54, or the examples, using the present UV absorber combination instead of the UVA of formula I.

Applications in photographic material and other recording materials, as well as further components to be used therein together with the present UV absorber combination, are, for example, as described in GSA-2343007 from page 22, last paragraph, until page 134, last paragraph. The novel UV absorber combination may also be used with advantage in optical recording layers and materials, wherein a laser beam effects a change of optical properties, e.g. by short wavelength irradiation by means of a blue laser diode (wavelength e.g. 405 nm), allowing storage of digital information which may be retrieved again from the storage layer or storage medium. Examples for such uses and materials can be found, inter alia, in JP-A-2001-277720; JP-A-2002-160452.

The novel UV absorber combination may be used for protecting its substrate (e.g. thermoplastic polymer or coating) as well as other light sensitive components such as pigments or dyes.

The UV absorber combination according to the invention can also be used advantageously in protective coatings, films and foils in liquid crystal displays for protection against UV radiation and to protect polymer material and other components in the liquid crystal displays against damage by UV light. Examples of such fields of application and materials are to be found inter alia in:

JP-A-10-152568 (9 Jun. 1998); JP-A-2000-227509 (8 Feb. 1999); JP-A-2000-227508 (2 Aug. 1999); JP-A-11-258425 (30 Nov. 1998); JP-A-11-258421 (13 Mar. 1998); JP-A-11-242119 (30 Nov. 1998); JP-A-11-119003 (13 Oct. 1997); JP-A-09-288213 (19 Apr. 1996); JP-A-09-288212 (19 Apr. 1996); JP-A-08-216316 (14 Feb. 1995); JP-A-08-216324 (14 Feb. 1995); and Chem. Abstr. 131: 45869. A preferred type of polymer film in this type of application is based on cycloolefins, for instance of cyclopentene or norbornene, as listed further above under point 1, line 3, in the list of polymers which can be stabilized.

The UV absorber combination of present invention is further effective in cosmetic formulations for the protection of human (or animal) skin or hair against UV radiation.

Dosage and Ratios

The stabilizers of the instant component (b) and optional further stabilizers are preferably present in the material to be stabilized in an amount of 0.01 to 10% by weight, relative to the material to be stabilized. An amount of 0.01 to 5% by weight or 0.05 to 2% by weight, in particular 0.05 to 0.5% by weight is especially preferred.

The stabilizer(s) of component (b) and optional further additives can also be added to the material to be stabilized in the form of a masterbatch which contains these components in a concentration of, for example, about 2.5% to about 25% by weight; in such operations, the polymer can be used in the form of powder, granules, solutions, suspensions or in the form of latices.

The novel coating composition preferably comprises 0.01-10 parts by weight of (b), in particular 0.05-10 parts by weight of (b), especially 0.1-5 parts by weight of (b), per 100 parts by weight of solid binder (a).

Generally, the present UV absorber combination may advantageously be used in multilayer systems, where the concentration of the novel stabilizer (component (b)) in the outer layer can be relatively high, for example from 1 to 15 parts by weight of (b), in particular 3-10 parts by weight of (b), per 100 parts by weight of the polymeric substrate (a).

In a similar manner, UV filter layers may be obtained using the present UV absorber combination in the top layer or one of the top layers of a coextruded article, e.g. a coextruded polycarbonate sheet, a polyester packaging film, a polyolefin covering film, or the top layer of a coating. Depending on the specific application, the amount of UV absorber combination of the invention incorporated in these layers may vary from relatively high loadings (e.g. 3-15 parts per 100 parts of polycarbonate, thickness of layer ca. 10-100 μm), to relatively low loadings (e.g. 0.1-0.8 parts per 100 parts of polyolefin, especially polyethylene, in an agricultural film).

The present UV absorber combination preferably contains components (A):(B) in a weight ratio from 1:20 to 10:1, more preferably from 1:10 to 2:1, especially from 1:9 to 1:1.

Where sterically hindered amines (HALS) are present, these are preferably used in a ratio of HALS:UVA ranging from 1:10 to 20:1, especially from 1:3 to 10:1.

The stabilized compositions disclosed herein are further illustrated by the following examples. Percentages given are by weight unless otherwise indicated.

EXAMPLE 1

Stabilization of Thermoplastic Olefins

Molded test specimens are prepared by injection molding thermoplastic olefin (TPO) pellets containing pigments, a phosphite, a phenolic antioxidant or hydroxylamine, a metal stearate, ultraviolet light absorbers or a hindered amine stabilizer or a mixture of UV absorber and hindered amine stabilizer.

Pigmented TPO pellets are prepared from pure pigment or pigment concentrate, coadditives and commercially available TPO by mixing the components in a Superior/MPM 1" single screw extruder with a general all-purpose screw (24:1 UD) at 400° F. (200° C.), cooled in a water bath and pelletized. The resulting pellets are molded into 60 mil (0.006 inch), 2"×2" plaques at about 375° F. (190° C.) on a BOY 30M Injection Molding Machine.

Pigmented TPO formulation composed of polypropylene blended with a rubber modifier where the rubber modifier is an in-situ reacted copolymer or blended product containing copolymers of propylene and ethylene with or without a ternary component such as ethylidene norbornene are stabilized with a base stabilization system consisting of an N,N-dialkylhydroxylamine or a hindered phenolic antioxidant with or without an organophosphorus compound.

All additive and pigment concentrations in the final formulation are expressed as weight percent based on the resin.

Formulations contain thermoplastic olefin pellets and one or more of the following components:
  0.0 to 2.0% pigment,
  0.0 to 50.0% talc,
  0.0 to 0.1% phosphite,
  0.0 to 1.25% phenolic antioxidant,
  0.0 to 0.1% hydroxylamine,
  0.05 to 0.10 calcium stearate,
  0.1 to 1.25%, especially 0.1 to 0.3% UV absorber,
  0.0 to 1.25% hindered amine stabilizer.

The components are dry-blended in a tumble dryer prior to extrusion and molding.

Test plaques are mounted in metal frames and exposed in an Atlas Ci65 Xenon Arc Weather-Ometer at 70° C. black panel temperature, 0.55 W/m² at 340 nanometers and 50% relative humidity with intermittent light/dark cycles and water spray (Society of Automotive Engineers—SAE J 1960 Test Procedure). Specimens are tested at approximately 625 kilojoule intervals by performing color measurements on an Applied Color Systems spectrophotometer by reflectance mode according to ASTM D 2244-79. Data collected include delta E, L*, a* and b* values. Gloss measurements are conducted on a BYK-Gardner Haze/Gloss Meter at 60° according to ASTM D 523.

UV Exposure Testing

Test specimens exposed to UV radiation exhibit exceptional resistance to photodegradation when stabilized with light stabilizer systems comprising a combination of 2-(2-hydroxy-3,5-di-tert-amylphenyl)-2H-benzotriazole (TINUVIN®328, Ciba) and compound (A2) and optionally an additional hindered amine such as N,N',N",N"'-tetrakis[4,6-bis(butyl (1,2,2,6,6-pentamethylpiperidin-4-yl)amino)-s-triazin-2-yl]-1,10-diamino-4,7-diazadecane (CHIMASSORB® 119, Ciba) or bis(2,2,6,6-tetramethylpiperidyl)sebacate (Tinuvin® 770). The control sample consists of a stabilizer formulation commonly used in the industry to impart UV stability. All of the samples contain a pigment, Pigment Red 177, and talc.

The test plaques described earlier contain the following (all concentrations are weight percent based on resin):

Polymer substrate is commercially available polyolefin blend POLYTROPE® TPP 518-01 supplied by A. Schulman Inc. Akron, Ohio)

Color package is 0.025% Red 3B-Pigment Red 177, C.I. #65300.

Each plaque contains:
  0.2% TINUVIN® 328 (ii of present component B);
  0.1% calcium stearate;
  15% talc;
  0.1% IRGANOX® B225 (50:50 blend of IRGANOX® 1010, Ciba (neopentanetetrayl tetrakis(4-hydroxy-3,5-di-tert-butylhydrocinnamate)) and IRGAFOS® 168, Ciba [tris-(2,4-di-tert-butylphenyl)phosphite]);
  0.2% TINUVIN® 770, Ciba [bis(2,2,6,6-tetramethylpiperidin-4-yl)sebacate];
  0.2% CHIMASSORB® 944, Ciba [polycondensation product of 4,4'-hexamethylene-bis(amino-2,2,6,6-tetramethylpiperidine) and 2,4-dichloro-6-tert-octylamino-s-triazine].

The five test plaques each contain 0.1% of compound (A2).

Sample 1 additionally contains
  0.2% of TINUVIN® 123, Ciba, [bis(1-octyloxy-2,2,6,6-tetramethylpiperidin-4-yl)sebacate] (HALS 24).
Sample 2 additionally contains
  0.2% of the compound HALS (109) and
  0.2% of the compound (ii).
Sample 3 additionally contains
  0.2% of CHIMASSORB® 119; and
  0.2% of the compound of HALS (108); and
  0.2% of the compound (vi).
Sample 4 additionally contains
  0.4% of the compound of HALS (36-d); and
  0.2% of the compound (xlv).
Sample 5 additionally contains
  0.4% of the compound of HALS (108); and
  0.2% of the compound (xli).

The test plaques 2-5, containing the present UVA combination together with hindered amines, show improved gloss retention compared to the plaques with the less effective control system containing the sole UVA (ii). Resistance to color change upon UV exposure is also enhanced.

Polymer blends containing an unsaturated ternary component, such as EPDM blends, are especially benefited with the more efficient instant light stabilizer systems described above.

In all cases, the light stabilized formulations show much greater resistance to photodegradation than unstabilized specimens which fail quickly under the UV exposure conditions outlined above.

EXAMPLE 2

Paintable TPO

Molded test specimens are prepared by injection molding thermoplastic olefin (TPO) pellets containing the instant compounds, pigments and other coadditives as described in Example 1.

The light stable formulations are painted with one-pack paint systems and tested for TPO/paint interactions. Before painting, the test specimens are first washed in accordance with GM998-4801 and dried for 15 minutes at 200° F. (94° C.). Adhesion promoter is applied to the dry film thickness of 0.2-0.4 mils. The samples are dried for five minutes before a 1K basecoat is applied to a film thickness of 1.2-1.4 mils. The painted panels are dried for three minutes, a clearcoat is then applied to a dry film thickness of 1.2-1.5 mils followed by ten minutes flash drying and a 30 minute oven bake at 250° F. (121° C.).

Paint adhesion is measured by Aggressive Adhesion Testing (proprietary test procedure conducted at Technical Finishing, Inc.) and Taber Scuff. Painted panels which retain greater than 80% of the paint finish are considered acceptable. After Aggressive Adhesion Testing, samples with less than 5% paint loss are deemed acceptable.

The control formulation contains 0.2% of bis(2,2,6,6-tetramethylpiperidin-4-yl)sebacate (TINUVIN® 770), 0.2% CHIMASSORB® 944, 0.2% TINUVIN® 328, 500 ppm calcium stearate and 750 ppm N,N-dialkylhydroxylamine in reactor-grade TPO.

Formulations A and B each contain 0.2% CHIMASSORB® 119, 0.2% TINUVIN® 328 (ii), 500 ppm calcium stearate and 750 ppm N,N-dialkylhydroxylamine in reactor-grade TPO.

Formulations A and B also contain 0.2% of one of the compounds (A1) or (A2) respectively.

Formulations C and D each contain 0.2% TINUVIN® 328 (ii), 500 ppm calcium stearate and 750 ppm N,N-dialkylhydroxylamine in reactor-grade TPO.

Formulations C and D also contain 0.4% of one of the compounds (A1) or (A2) respectively.

Formulations A-D are superior to the control formulation as measured by the Taber Scuff and Aggressive Adhesion Tests.

EXAMPLE 3

Stabilizer Mixtures for Coating Applications

3A: Preparation of Compound Mixtures

Mixtures in accordance with the following table 3A are prepared by dissolving the compounds indicated in xylene or Solvesso® 100 (aromatic hydrocarbon mixture, boiling range 161-178° C.; manufacturer: Exxon):

TABLE 3A

Mixtures of components (A) and (B); amounts in parts by weight (pbw)

| Component A | Component B | No. |
|---|---|---|
| 1 pbw A1 | 1 pbw ii | B1 |
| 1 pbw A1 | 1 pbw iii | B2 |
| 1 pbw A1 | 1 pbw iv | B3 |
| 1 pbw A1 | 1 pbw vi | B4 |
| 1 pbw A1 | 1 pbw vii | B5 |
| 1 pbw A1 | 1 pbw. viii | B6 |
| 1 pbw A1 | 1 pbw xvi | B7 |
| 1 pbw A1 | 1 pbw xx | B8 |
| 1 pbw A1 | 1 pbw xxv | B9 |
| 1 pbw A1 | 1 pbw xxxvii | B10 |
| 1 pbw A1 | 2 pbw ii | B11 |
| 1 pbw A1 | 2 pbw iii | B12 |
| 1 pbw A1 | 2 pbw iv | B13 |
| 1 pbw A1 | 2 pbw vi | B14 |
| 1 pbw A1 | 2 pbw vii | B15 |
| 1 pbw A1 | 2 pbw viii | B16 |
| 1 pbw A1 | 2 pbw xvi | B17 |
| 1 pbw A1 | 2 pbw xx | B18 |
| 1 pbw A1 | 2 pbw xxv | B19 |
| 1 pbw A1 | 2 pbw xxxvii | B20 |
| 1 pbw A1 | 3 pbw ii | B21 |
| 1 pbw A1 | 3 pbw iii | B22 |
| 1 pbw A1 | 3 pbw iv | B23 |
| 1 pbw A1 | 3 pbw vi | B24 |
| 1 pbw A1 | 3 pbw vii | B25 |
| 1 pbw A1 | 3 pbw viii | B26 |
| 1 pbw A1 | 3 pbw xvi | B27 |
| 1 pbw A1 | 3 pbw xx | B28 |
| 1 pbw A1 | 3 pbw xxv | B29 |
| 1 pbw A1 | 3 pbw xxvii | B30 |
| 1 pbw A1 | 3 pbw 1:1 mixture of xvi and viii | B31 |
| 1 pbw A1 | 3 pbw 1:1 mixture of ii and viii | B32 |
| 3 pbw A1 | 1 pbw ii | B33 |
| 2 pbw A1 | 1 pbw xi | B34 |
| 2 pbw A1 | 1 pbw xvi | B35 |
| 1 pbw A2 | 2 pbw ii | B36 |
| 1 pbw A2 | 2 pbw iii | B37 |
| 1 pbw A2 | 2 pbw iv | B38 |
| 1 pbw A2 | 2 pbw vi | B39 |
| 1 pbw A2 | 2 pbw xxvii | B40 |
| 1 pbw A2 | 2 pbw xxv | B41 |
| 1 pbw 1:1 mixture of A1 and A2 | 3 pbw xx | B42 |
| 1 pbw 1:1 mixture of A1 and A2 | 3 pbw viii | B43 |
| 1 pbw 1:1 mixture of A1 and A2 | 3 pbw vii | B44 |
| 1 pbw 1:1 mixture of A1 and A2 | 1 pbw xvi | B45 |
| 1 pbw 1:1 mixture of A1 and A2 | 2 pbw xi | B46 |
| 1 pbw 1:1 mixture of A1 and A2 | 2 pbw xvii | B47 |
| 1 pbw A1 | 5 pbw ii | B48 |
| 1 pbw A1 | 4 pbw iii | B49 |
| 1 pbw A1 | 5 pbw iv | B50 |
| 1 pbw A1 | 4 pbw vi | B51 |
| 1 pbw A1 | 4 pbw vii | B52 |
| 1 pbw A1 | 4 pbw viii | B53 |
| 1 pbw A1 | 5 pbw xvi | B54 |
| 1 pbw A1 | 5 pbw xx | B55 |
| 1 pbw A1 | 5 pbw xxv | B56 |
| 1 pbw A1 | 5 pbw xxvii | B57 |
| 2 pbw A1 | 1 pbw ii | B58 |
| 2 pbw A1 | 1 pbw iii | B59 |
| 2 pbw A1 | 1 pbw iv | B60 |
| 2 pbw A1 | 1 pbw vi | B61 |
| 2 pbw A1 | 1 pbw vii | B62 |
| 2 pbw A1 | 1 pbw viii | B63 |
| 2 pbw A1 | 1 pbw xx | B64 |
| 2 pbw A1 | 1 pbw xxv | B65 |
| 2 pbw A1 | 1 pbw xxxvii | B66 |

3B) Stabilization of a 2 Component Polyurethane Coating

The novel stabilizer mixtures are tested in a clearcoat having the following composition:

| I. Polyol component | |
|---|---|
| Macrynal SM 510 n (65%)[a] | 75.0 g |
| Butylglycol acetate | 15.0 g |
| Solvesso 100[b] | 6.0 g |
| Methyl isobutyl ketone | 3.6 g |
| Zn - octoate (8% metal) | 0.1 g |
| BYK 300[c] | 0.2 g |
| Subtotal | 100.0 g |
| II. Isocyanate component | |
| Desmodur N 75[d] (75%) | 40.0 g |
| Total | 140.0 g |
| Resin solids (total): | 56.2% |

[a]OH-functional poly(meth)acrylat (formerly Vianova Resins GmbH, Germany).
[b]aromatic hydrocarbon mixture, boiling range 182-203° C. (Solvesso 150) or 161-178° C. (Solvesso 100); manufacturer: ESSO.
[c]levelling agent based on dimethylpolysiloxane (Byk Chemie, Wesel, Germany).
[d]isocyanate hardener (75% by weight in methoxypropylacetate/xylene 1:1; Bayer AG).

1.5% of the mixture to be tested is added in a solution in about 5-10 g of Solvesso® 100 to the clearcoat, based on the solids content of the paint. The coating formulations are additionally admixed with 1.0% by weight, based on the solids content of the paint, of a costabilizer (compound C) with main component of the formula

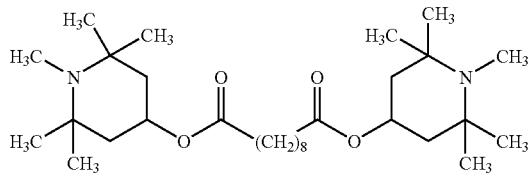

(HALS 14a; Ciba Specialty Chemicals).

The comparison used is a clearcoat containing no light stabilizer and a clearcoat stabilized using 1.5% of compound A or B instead of the present UVA combination; the corresponding results are marked in the tables below with an asterisk (**).

The clearcoat is diluted to spray viscosity with Solvesso®100 and applied to a prepared aluminium panel (coil coat, filler, silver metallic base-coat) and the painted panel is baked at 130° C. for 30 minutes. This gives a clearcoat dry-film thickness of 40-50 μm.

Subsequently, the yellowing is detected compared to the same coating containing no UV absorber mixture of the invention (color measurements on an Applied Color Systems spectrophotometer by reflectance mode according to ASTM D 2244-79; data collected include delta E, L*, a* and b* values).

The samples are then subjected to weathering in an UVCON® weathering device from Atlas Corp. (UVB-313 lamps) with a cycle of 8 h of UV irradiation at 70° C. and 4 h of condensation at 50° C. Further samples are subjected to natural weathering (Florida, 5° south, SAE J-1976).

The surface gloss (20° gloss in accordance with DIN 67530) and the colour change (ASTM D 2244-79) of the samples are measured at regular intervals. The results are compiled in Table 3B below. All amounts are based on the solids content of the clearcoat.

TABLE 3B

Lowering of initial yellowing (b* vs. unstabilized clearcoat) and 20° gloss retention after weathering

| UVA | b* | 20° gloss 1200 h | after 2400 h | 3600 h | 4800 h | 5200 h |
|---|---|---|---|---|---|---|
| None | — | 32 | | | | |
| 1.5% xvii** | 0.2 | 93 | 93 | 91 | 68 | 19 |
| 1.5% vii** | 0.22 | 93 | 90 | 91 | 70 | 14 |
| 1.5% A1** | 0.44 | 93 | 92 | 90 | 81 | 77 |
| 1.0% A1/0.5% vii (= B62) | 0.28 | 91 | 92 | 90 | 89 | 81 |
| 0.5% A1/1% vii (= B15) | 0.15 | 91 | 93 | 91 | 88 | 82 |
| 0.3% A1/1.2% vii (= B53) | 0.12 | 91 | 93 | 90 | 88 | 81 |

**comparative test

Good results are also obtained replacing compount C (HALS 14a) with the same amount of HALS 24, 49-a-3, 110, 111 or 112.

EXAMPLE 3C

Stabilizing a 2-Coat Metallic Paint

The novel stabilizer mixtures are tested in a clearcoat having the following composition:

| | |
|---|---|
| Synthacryl ® SC 303[1] | 27.51 |
| Synthacryl ® SC 370[2] | 23.34 |
| Maprenal ® 650[3] | 27.29 |
| butyl acetate/butanol (37/8) | 4.33 |
| isobutanol | 4.87 |
| Solvesso ® 150[4] | 2.72 |
| Kristallol K-30[5] | 8.74 |
| levelling assistant Baysilon ® MA[6] | 1.20 |
| | 100.00 g |

[1]acrylate resin from Hoechst AG; 65% solution in xylene/butanol 26:9
[2]acrylate resin from Hoechst AG; 75% solution in Solvesso 100[4]
[3]melamine resin from Hoechst AG; 55% solution in isobutanol
[4]aromatic hydrocarbon mixture, boiling range 182-203° C. (Solvesso 150) or 161-178° C. (Solvesso 100); manufacturer: ESSO
[5]aliphatic hydrocarbon mixture, boiling range 145-200° C.; manufacturer: Shell
[6]1% in Solvesso 150[4]; manufacturer: Bayer AG 1.5% of the mixture to be tested is added in a solution in about 5-10 g of Solvesso® 100 to the clearcoat, based on the solids content of the paint. The coating formulations are additionally admixed with 0.7% by weight, based on the solids content of the paint, of a costabilizer (compound C=HALS 24) of the formula (Compound C)

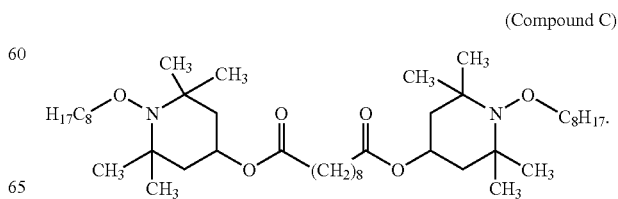

The comparison used is a clearcoat containing no light stabilizer and a clearcoat stabilized using the individual components; the corresponding results are marked in the tables below with an asterisk (*).

The clearcoat is diluted to spray viscosity with Solvesso®100 and applied to a prepared aluminium panel (coil coat, filler, silver metallic or blue metallic base-coat) and the painted panel is baked at 130° C. for 30 minutes. This gives a clearcoat dry-film thickness of 40-50 μm.

The samples are then subjected to weathering in an UVCON® weathering device from Atlas Corp. (UVB-313 lamps) with a cycle of 8 h of UV irradiation at 70° C. and 4 h of condensation at 50° C. Further samples are subjected to natural weathering (Florida, 5° south, SAE J-1976).

The surface gloss (20° gloss in accordance with DIN 67530) and the colour change (ΔE in accordance with DIN 6174) of the samples are measured at regular intervals.

The results are compiled in Tables C1 and C2 below. All amounts are based on the solids content of the clearcoat.

The smaller the colour change value, the better the stabilization.

The samples stabilized in accordance with the invention exhibit better weathering stability (gloss and colour retention) than comparison samples.

EXAMPLE 4

Coatings over Plastic Substrates

A major application for hindered amines is in the protection of automotive topcoats applied over plastic substrates. However, many low molecular weight, non-reactable light stabilizers migrate into the plastic substrate during drying and cure. As a consequence, a significant portion of the light stabilizer may be lost from the topcoat into the substrate and hence be ineffective in protecting said topcoat.

The extent of migration of hindered amine stabilizers during application and cure of the coating is determined by comparing the concentration of hindered amine in the cured clearcoat applied over a plastic substrate versus the same clearcoat applied over a non-permeable substrate such as glass or steel.

UVA combinations under test are incorporated into a flexible thermoset acrylic/melamine clear coating appropriate for use on automotive plastic substrates. The UVA combination is incorporated at a level of 1.5% by weight based on total resins solids. In all combinations, the component (A) used is compound A1 at a level of 0.5% by weight based on total resins solids. Where 2 compounds are used as component (B), each compound is added in an amount of 0.5% by weight based on total resins solids.

Some formulations additionally contain a sterically hindered amine at a level of 1.5% by weight based on total resins solids. The stabilizers added can be seen in the following table:

| Sample No. | UVA component (B) | HALS |
|---|---|---|
| 1 | ii | 14-a |
| 2 | iii | 24 |
| 3 | iv | 111 |
| 4 | vi | 112 |
| 5 | vii | 49-a-3 |
| 6 | viii | 110 |
| 7 | xx | 14-a |
| 8 | xvi | 49-a-3 |

-continued

| Sample No. | UVA component (B) | HALS |
|---|---|---|
| 9 | xxv | 24 |
| 10 | xxxvii | 111 |
| 11 | ii + xii | none |
| 13 | iii + xvi | none |
| 14 | iv + xvii | none |
| 15 | vi + xviii | none |
| 16 | vii + xii | none |
| 17 | viii + xvii | none |

Each coating formulation is applied by an automatic spray apparatus onto automotive grade RIM (Reacting Injection Molded) substrate and TPO (thermoplastic polyolefin). Both substrates are in the form of 4"×12" plaques. Each coating is applied to achieve a dry film thickness of approximately 2.0 mils (50 microns). The coatings are cured by baking at 250° F. (121° C.) for 20 minutes.

Triplicate samples of each cured coating formulation are removed from each substrate and cryo-ground to a fine powder. A known amount of each sample is extracted in refluxing toluene overnight. The UVA present is analyzed quantitatively by dilution to a known volume and spectrophotometry.

With the present UVA combination, a high percent recovery of the UV absorbers from the clearcoat over a plastic substrate is found indicating that much less of the present UVA migrate into the plastic substrate; thereby allowing for better stabilization of the clear topcoat over such plastic substrates.

EXAMPLE 5

Stabilization of Polypropylene Molded Articles

Molded test specimens are prepared by injection molding polypropylene pellets containing pigments, a phosphite, a phenolic antioxidant or hydroxylamine, a metal stearate, ultraviolet light absorbers or a mixture of UV absorbers and hindered amine stabilizers.

Pigmented polypropylene pellets are prepared from pure pigment or pigment concentrates, stabilizers, co-additives and commercially available polypropylene by mixing the components in a Superior/MPM 1" single screw extruder with a general all-purpose screw (24:1 L/D) at 475° F. (250° C.), cooled in a water bath and pelletized. The resulting pellets are molded into 60 mil (0.06 inch thick) 2"×2" plaques at about 475° F. (250° C.) on a BOY 30M Injection Molding Machine.

Pigmented polypropylene formulations composed of polypropylene homopolymer or polypropylene copolymer are stabilized with a base stabilization system consisting of an N,N-dialkylhydroxylamine or a hindered phenolic antioxidant with or without an organophosphorus compound.

All additive and pigment concentrations in the final formulations are expressed as weight percent based on the resin.

Formulations contain polypropylene pellets and one or more of the following components;
0.0%-2.0% pigment,
0.0%-50.0% talc,
0.0%-50.0% calcium carbonate,
0.0%-0.1% phosphite,
0.0%-1.25% phenolic antioxidant,
0.0%-0.1% hydroxylamine, 0.05%-0.10% calcium stearate,
0.05%-0.25% UV absorber,
0.0%-1.25% hindered amine stabilizer.

The components are dry blended in a tumble dryer prior to extrusion and molding.

Test plaques are mounted in metal frames and exposed in an Atlas Ci65 Xenon Arc Weather-Ometer at 70° C. black panel temperature, 0.55 W/m² at 340 nanometers and 50% relative humidity with intermittent light/dark cycles and water spray (Society of Automotive Engineers—SAE J 1960 Test Procedure). Specimens are tested at approximately 625 kilojoule intervals by performing color measurements on an Applied Color Systems spectrophotometer by reflectance mode according to ASTM D 2244-79. Data collected included delta E, L*, a* and b* values. Gloss measurements are conducted on a BYK-GARDNER Haze/Gloss Meter at 60° according to ASTM D523.

UV Exposure Testing

Test specimens exposed to UV radiation exhibit exceptional resistance to photodegradation when stabilized with light stabilizer systems comprised of a combination of compound B (see below), and 0.1% of compound (A2). Test specimens also exhibit exceptional resistance to photodegradation. The control sample consists of a stabilizer formulation commonly used in the industry to impart UV stability, a mixture of 0.2% Tinuvin® 328 and a hindered amine stabilizer. All amounts given are based on the weight of the resin. All of the samples contain Pigment Red 177.

Each test sample contains a compound (A) and (B), and optionally a hindered amine stabilizer in an amount of 1.5% b.w., e.g. 1-(2-Hydroxy-2-methylpropoxy)-4-octadecanoyloxy-2,2,6,6-tetramethylpiperidine, bis-(1-octyloxy-2,2,6,6-tetramethylpiperidin-4-yl)sebacate (Tinuvin® 123) or bis-(1-cyclohexyloxy-2,2,6,6-tetramethylpiperidin-4-yl) succinate.

All formulations are base stabilized with 0.05% dialklyhydroxylamine in the final resin formulation.

Polymer substrate is a commercially available polypropylene homopolymer—Profax 6501 (commercial supplier Montell Polyolefins).

Color package is 0.25% Red 3B—Pigment Red 177, C.I. # 65300 in the final resin formulation. Each formulation contains 0.1% calcium stearate. Samples are 60 mil thick 2"×2" injection molded plaques. UV exposures conducted under SAE J 1960—Exterior Automotive conditions. All additive and pigment concentrations in the final formulations are expressed as weight percent on the resin.

Tested formulations contain 0.05% of tris[2,4-di-tert-butylphenyl]phosphite, 0.05% of pentaerythritol tetrakis[3-(3,5-di-tert-butyl-4-hydroxy-phenyl)propionate], 0.05% of calcium stearate, and the following components:
0.1% compound A2;
0.3% of compound B selected from i, v, x, xi, xii, xiii, xvii;
1.5% of a HALS selected from Nos. 13 (Tinuvin 770), 84-1 (Chimassorb 944), 76 (Chimassorb 119), 81 (Tinuvin 622), 92-1, and 109;
all amounts given are by weight of the polymer used.

The formulations containing the present combination od components (A) and (B) exhibit improved gloss retention and resistance to color change when compared to the control formulation.

In all cases, the light stabilized formulations show much greater resistance to photodegradation than unstabilized specimens which fail quickly under the UV exposure conditions outlined above.

EXAMPLE 6

Polypropylene Fiber

Fiber samples are prepared by extruding fiber-grade polypropylene with a present combination of components (A) and (B), coadditives and pigments. Typical formulations contain the hindered amines at levels from 0.05 to 2.0%, a metal stearate such as calcium stearate at 0.05 to 0.5%, pigments from 0 to 5%, UV absorbers at levels of 0.05 to 2.0%, phosphites at 0 to 0.1%, phenolic antioxidants at 0 to 1.25%, N,N-dialkylhydroxylamines at 0 to 0.1% and optionally other hindered amines at levels of 0 to 2.0%. All additive and pigment concentrations in the final formulations are given as weight percent based on the resin.

Novel stabilizer combinations employed are
(6a) 1 part by weight (pbw) of compound A2 and 2 pbw of compound vii;
(6b) 1 part by weight (pbw) of compound A2 and 2 pbw of compound viii;
(6c) 1 part by weight (pbw) of compound A2 and 2 pbw of compound xix;
(6d) 1 part by weight (pbw) of compound A2 and 1 pbw of compound xii.

2.5 g of one of the above novel stabilizer combinations are mixed together with 1 g of tris(2,4-di-tert-butylphenyl) phosphite, 1 g of calcium monoethyl 3,5-di-tert-butyl-4-hydroxybenzylphosphonate, 1 g of calcium stearate and 2.5 g of $TiO_2$ (Kronos RN 57) in a turbine agitator with 1000 g of polypropylene powder (melt index 12 g/10 min, measured at 230° C./2.16 kg). The mixtures are extruded at 200-230° C. to granules; these granules are subsequently processed to fibres using a pilot plant (Leonard; Sumirago/VA, Italy) under the following conditions:

| | |
|---|---|
| Extruder temperature: | 190-230° C. |
| Head temperature: | 255-260° C. |
| Draw ratio: | 1:3.5 |
| Drawing temperature: | 100° C. |
| Fibres: | 10 den |

The fibres prepared in this way are exposed against a white background in a Weather-O-Meter® Type 65 WR (Atlas Corp.) with a black standard temperature of 63° C. in accordance with ASTM D 2565-85. After different exposure times the residual tensile strength of the samples is measured. From the measurements the exposure time $T_{50}$ after which the tensile strength of the samples has fallen to half its original level is calculated.

For comparison purposes, fibres without novel stabilizer are produced and tested under otherwise identical conditions.

The fibres stabilized in accordance with the stabilizer combination of the invention exhibit outstanding strength retention.

EXAMPLE 7

Stabilization of a Gray Pigmented Polycarbonate/ABS Blend

Commercial PC/ABS-blend (Cycoloy™ MC 8002; 50/50 wt/wt blend of PC and ABS pigmented with 1% by weight of Gray 9779 is stabilized by addition of 0.5% by weight of HALS (102), 0.3% by weight of 2-(2'-hydroxy-3',5'-bis(1, 1-dimethylbenzyl)phenyl)-benztriazole (iii) and 0.1% by weight of the compound indicated in the following table. A sample containing 0.3% by weight of the benztriazole stabilizer (B) or present component (A) instead of present combination and an unstabilized sample serve as comparison. Izod bars (2.5"L×0.5"W×0.125"W) are prepared by injection molding on a BOY 30 machine, barrel temperature 475-515° F., die temperature 515° F. Accelerated weathering is performed using an Atlas Ci65A Weathermeter (XAW), operated in either "Dry XAW" mode (ASTM G26-90 method C). After regular intervals, the color change ΔE according to DIN 6174 is determined. Results are compiled in table 7.

TABLE 7

Color change (ΔE) of gray pigmented PC after the indicated irradiance time

| UV absorber | Irradiance time: | | | |
|---|---|---|---|---|
| | 100 h ΔE | 500 h ΔE | 1000 h ΔE | 1250 h ΔE |
| none | | | | |
| 0.3% iii | | | | |
| 0.1% A1 | | | | |
| 0.3% iii + 0.1% A1 | | | | |
| 0.3% iii + 0.1% A2 | | | | |

EXAMPLE 8

Polyethylene Film

Film grade polyethylene is dry blended with approximately 10% by weight of a test additive combination (A) and (B), and then melt compounded at 200° C. into "Masterbatch" pellets. The fully formulated "Masterbatch" pellets are dry blended with polyethylene resin to get the desired final stabilizer concentrations. Typical formulations contain a present compound (A) and (B) together at levels from 0.05% to 2.0%, a metal stearate such as calcium stearate at 0.05% to 0.5%, a phosphite at 0% to 0.1%, a phenolic antioxidant at 0% to 1.25%, an N,N-dialkylhydroxylamine at 0% to 0.1% and optionally a sterically hindered amine at 0.1% to 2.0%.

The additives reported in the table below are mixed via masterbatch with LDPE pellets (Riblene™ FF 29; d=0.921 g/cm; MFI (190° C./2.16 kg)=0.60 g/10 min.) in a turbo mixer. The mixtures are extruded at 200° C. to obtain granules that are converted into films of thickness 150 μm by compression molding (170° C./3 min.).

The blown films are exposed in an Atlas Xenon-Arc Weather-Ometer according to ASTM G26 at 63° C. bpt, 0.35 W/m² at 340 nm with no spray cycle. Films are tested periodically for any change in elongation using an Instron 112 tensile tester. Failure in this test is determined by observation of the loss of % elongation in the film. The longer it takes for this loss to occur, the more effective is the stabilizer system.

The films containing a mixture of present compounds (A) and (B) exhibit good light stabilizing efficacy as shown in the following table.

| Compound | Time to 50% Residual Elongation |
|---|---|
| 0.1% A2 + 0.4% v | |
| 0.1% A2 + 0.4% xiii | |
| 0.5% xvii | |

Good results are also achieved using additionally 1.5% of the following HALS:

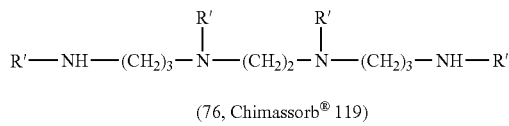

(76, Chimassorb® 119)

where R' is

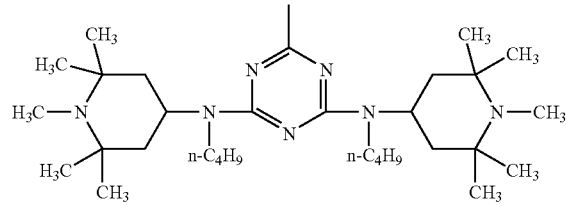

EXAMPLE 9

Polyethylene Film for Greenhouse

Films prepared in accordance with example 8 are exposed on a greenhouse on galvanized iron backing. Treatment includes applications of pesticides on a regular basis (i.e. sodium N-methyldithiocarbamate, VAPAN® every six months and SESMETRIN® every month). Performance is measured by monitoring the percent residual elongation. Failure is defined as the time to a 50% loss of original elongation.

The films containing a combination of present compounds (A) and (B) show good resistance to pesticides.

The films may further contain commercially available antifog agents such as Atmer® 103, a sorbitan ester, or Atmer® 502, an ethoxylated ether. Such films exhibit good UV light stability and good antifog resistance.

The films may further contain antistatic agents such as glycerol monostearate (GMS) or ethoxylated fatty amines. Such films exhibit good UV light stability and good antistatic properties.

Good results are also obtained with films additionally containing 1.5% of HALS (109), HALS (109) in combination with 2% of a hydrotalcite (DHT4A), or the following HALS:

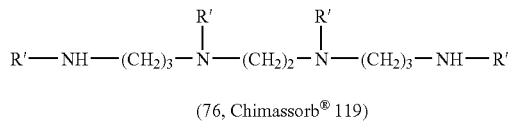

(76, Chimassorb® 119)

-continued where R' is

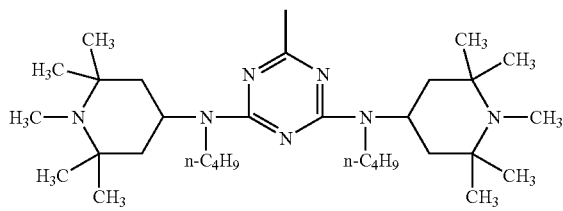

or HALS Nos. 92-1 or 92-2, each in combination with 2% of ZnO and 1% of hydrotalcite (DHT4A).

EXAMPLE 10

Polyethylene Film for Greenhouse

In order to prepare thin LDPE films and to evaluate the spectral features imparted by the additive and its persistency, compounds (A2) and (iv) or (A2) and (xii), each in a weight ratio A:B=1:1, are mixed with LDPE pellets (Riblene FF 29, supplied by Polimeri Europa, Milano, Italy), characterized by a density of 0.921 g/cm$^3$ and a melt flow index (190° C./2.16 Kg) of 0.6) in a turbo mixer in order to give a formulation containing 0.25% by weight of the additive combination. The mixture is extruded at a maximum temperature of 200° C. in a OMC twin-screw extruder. The granules so obtained are blown in a lab scale Formac blow-extruder at a maximum temperature of 210° C. to give a film 150 µm thick. UV-Vis spectra are recorded in the range 200-800 nm by means of a Perkin-Elmer Lambda 20 spectrophotometer, equipped with a RSA-PE-20 Labsphere integrating sphere.

Results: The film displays a strong absorption band in the range 280-360 nm. In order to test the photostability of the additive combination upon exposure to light, a portion of the film is exposed in an Atlas Weather-o-Meter (WOM), model Ci65A (as per ASTM G26-96, irradiance 0.35 W/m$^2$, black panel temperature 63±3° C.). After exposure, the film still displays a sufficient absorption in the range below 360 nm.

EXAMPLE 11

Polyethylene Mulch Film

Master batch pellets prepared as described in Example 9 are dry blended into polyethylene resin to get the final stabilizer concentration. The fully formulated resin is then blown at 200° C. into a 25 micron thick film using a DOLCI film line.

The resulting films are exposed on a soil to simulate agricultural mulch film conditions. Treatment includes exposure to methyl bromide fumigant for three days at 60 g/m$^3$. Performance is measured by monitoring the time to physical embrittlement.

The films containing 0.2% of present compounds (A1) or (A2) and 0.4% of (B) as listed above show good resistance to fumigants.

EXAMPLE 12

Polyethylene Film for Greenhouse

Greenhouse film samples are prepared as described in Example 10, and in addition to a present compounds (A) and (B), also contain a metal stearate and a metal oxide and a sterically hindered amine. Typical formulations contain from 0.05 to 2% by weight of the present stabilizer combination, from 0.05 to 2% by weight of a high molecular weight sterically hindered amine, 0.05 to 0.5% of a metal stearate such as calcium stearate, and 0.05 to 0.5% of a metal oxide such as zinc oxide, magnesium oxide or calcium oxide.

Effectiveness is monitored as described in Example 10. The films contain present combination (A2) and (B):

| ratio A:B | B | HALS |
|---|---|---|
| 1:2 | xxxv | 109 |
| 1:2 | xxxvi | 76 |
| 1:3 | xii | 92-1 |
| 1:3 | xii | 92-2 |
| 1:4 | xiii | 109 | together with 0.1% of calcium stearate, 0.5% of ZnO and 1.0% of the HALS compound. The films exhibit good light stability and pesticide resistance.

EXAMPLE 13

Thermoplastic Elastomers

Resin materials of the general class known as thermoplastic elastomers, examples of which include, copolymers of styrene with butadiene or isoprene and/or ethylene-cobutylene such as SBS, SEBS and SIS, are dry blended with a present compound of formula (A) or (B) and melt compounded into pellets. Typical formulations contain the instant compounds at levels from 0.05% to 2.0%, a metal stearate such as calcium stearate at 0.05% to 0.5%, and pigments from 0% to 5%, phosphites at 0.0%-0.1%, phenolic antioxidants at 0.0%-1.25%, N,N-dialkylhydroxylamine at 0.0%-0.1%, and hindered amine stabilizers at levels of 0.05% to 2.0%.

The pelletized fully formulated resin is then processed into a useful article such as blown or cast extrusion into film; injection molded into a molded article; thermoformed into molded articles; extruded into wire and cable housing; or rotational molded into hollow articles.

The following additives are used for combining with 0.5% of compound A2 (amounts b.w., based on the polymer):

| Sample No. | UVA component (B) | HALS |
|---|---|---|
| 1 | 1% i | 13 |
| 2 | 1% ii | 13 |
| 3 | 1% iii | 13 |
| 4 | 1% iv | 14-a |
| 5 | 1% v | 49-a-3 |
| 6 | 0.5% xvii | 76 |
| 7 | 1% vii | 76 |
| 8 | 0.5% viii | 36-d |
| 9 | 0.5% ix | 84-1 |

-continued

| Sample No. | UVA component (B) | HALS |
|---|---|---|
| 10 | 0.5% x | 112 |
| 11 | 0.5% xi | 111 |
| 13 | 0.5% xii | 92-2 |
| 14 | 0.5% xiii | 109 |
| 15 | 0.5% xvi | 13 |

The materials containing a present compounds (A) and (B) exhibit stability against deleterious effects of UV light and thermal exposure.

EXAMPLE 14

Polycarbonate 10 g of polycarbonate powder (Lexan 115) are dissolved with stirring in 50 g of methylene chloride at room temperature, a process which takes several hours. Also added is a total amount of 0.35 g of the UV absorber of formula (A2), (v) and/or (xix) as indicated in the below table, corresponding to a 3.5% concentration of additive mixture. These solutions are used to cast films with a thickness of 20 μm, according to the method given in EP-A-500496.

The films are exposed in an Atlas Weatherometer CI 65 at a black panel temperature of 63° C. (0.35 W/m$^2$ at 340 nm; dry, no dark phase). The discolouration of the samples is checked at regular intervals by measuring the Yellowness Index (YI, method DIN 6167). Results are reported in Tab. 14.

TABLE 14

| | YI after exposure | | | |
|---|---|---|---|---|
| UV absorber | 0 h | 4000 h | 8000 h | 10000 h |
| 3.5% of the UVA compound A2 | −0.1 | 5.1 | 7.3 | destroyed |
| 2.333% A2 and 1.167% xix | −0.4 | 3.6 | 4.5 | 5.2 |
| 1.167% A2 and 2.333% xix | 0.0 | 4.0 | 6.3 | 4.6 |
| 2.333% A2 and 1.167% v | | | | |

The compositions containing the present stabilizer mixture show distinctly improved colour and stability properties.

In case that polycarbonate is processed at elevated temperature, a process stabilizer selected from phosphites, phosphonotes and phenolic antioxidants is used concomitantly. Good results are achieved using 0.05 or 0.1%, based on the polycarbonate weight, of tris(2,4-di-tert.butylphenyl) phosphite; single layer sheets or multilayer sheets containing this phosphite and the above UVA mixture show reduced blooming, good transparency and excellent weathering results.

Coextruded polycarbonate sheets are prepared as described in examples 1 and 6 of EP-A-825226, sample A, using present UVA combination instead of pure Tinuvin 1577, and with a total of 5% of present UVA combination present in the cap layer of thickness 40 micrometer and 0.1% of present UVA combination present in the bulk layer of thickness 7 mm. UVA combination used is compounds (A2) and (v) in a ratio 1:3 or (A2) and (xix) in a ratio 1:2. The produced sheets show essentially no fuming.

EXAMPLE 15

Cosmetic Use

Suspension of the Mixture of Compound (A2) and Compound (xiv)

| | |
|---|---|
| UV-absorber (A2) | 1 g |
| UV-absorber (xiv) | 2 g |
| $C_8$–$C_{12}$-fatty alcohol polyglucoside | 2.4 g |
| sodium chloride | 1 g |
| Xanthan gum | 0.5 g |
| Bronopol | 0.1 g |
| deionised water | 93 g |

Preparation of the Formulation 40 g of the UV absorber suspension, 20 g of the fatty alcohol polyglucoside and 40 g water are mixed together and milled with a ball mill (Drais), so that the diameter of the milled particles becomes smaller than 1 μm. Starting form this paste the other components of the above dispensing are admixed accordingly.

The measured sun protection factors (SPF; Diffey und Robson) and photo stabilities detected show that the effective substances have a high photo stability and that a high sun protection factor can be obtained with a low concentration of present UVA combination.

EXAMPLE 16

Wood Varnish a) Impregnation: Relative to the weight of the total formulation 0.5% of the additives indicated in Table 16 below is added to a commercially available impregnant (Xylamon Incolore™; Manufacturer: Sepam).

The impregnant is applied by brush to spruce boards (one application) and dried at room temperature for 24 hours.

b) Topcoat: A topcoat is prepared from:

| | |
|---|---|
| 53.48 | parts by weight of alkyd resin (Jägalyd Antihydro ™, E. Jäger KG, 60% solution in white spirit); |
| 10.69 | parts by weight of a thixotropic auxiliary (Jägalyd Antihydro-Thix ™, E. Jäger KG, 50% solution); |
| 1.92 | parts by weight of accelerator (Jäger Antihydro-Trockner ™); |
| 33.44 | parts by weight of solvent (Terlitol ™ 30); |
| 0.32 | part by weight of anti-skinning agent (Ascinin ™ P, BAYER); |
| 0.15 | part by weight of anti-skinning agent (Luactin ™ M, BASF). |

The topcoat is stabilized by adding 1.0% of novel UV absorber combination and 1.0% of the compound of formula

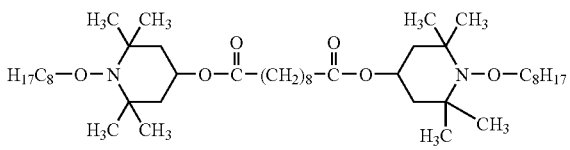

(hindered amine light stabilizer, see above No. 24, Ciba Specialty Chemicals), the amounts being based in each case on the solids content of the binder. A comparative specimen is prepared without the addition of these stabilizers.

The topcoat is applied by brush (3 applications) to the impregnated spruce boards, which are dried at room temperature for 24 hours after each application.

The specimens are subsequently subjected to accelerated weathering: UV-A lamps with maximum light intensity at 340 nm; weathering cycle: 5 h of light at 58° C., 1 h of spraying at 22° C.

After the stated period of weathering the colour change ΔE is determined in accordance with DIN 6174; the comparison used is an unweathered specimen with unstabilized impregnant and unstabilized topcoat. The results are collated in Table 16, ratios are indicated in parts by weight (pbw).

TABLE 16

Colour change ΔE in accordance with DIN 6174 on spruce, 1000 h of weathering

| Stabilizer combination | Colour change ΔE |
|---|---|
| None | |
| 1 pbw (A2) + 2 pbw (xvi) | |
| 1 pbw (A2) + 2 pbw (viii) | |

The instant stabilizers provide good color stabilization.

EXAMPLE 17

Incorporation into a Photographic Material

A gelatin layer having the following composition (per m²) is applied conventionally to a polyester base:

| Component: | Amount: |
|---|---|
| Gelatin | 1200 mg |
| Tricresyl phosphate | 510 mg |
| Curing agent | 40 mg |
| Wetting agent | 100 mg |
| Components (A) and (B) | 225 mg |

The curing agent is the potassium salt of 2-hydroxy-4,6-dichloro-1,3,5-triazine. The wetting agent is sodium 4,8-diisobutylnaphthalene-2-sulfonate. As component (A), 75 mg of compound (A1), and as component (B), 75 mg of each of compounds (xiv) and (xv), or 150 mg of compound (viii) is used.

The gelatin layers are dried for 7 days at 20° C.

With the novel UVA combination, clear transparent layers are obtained which are suitable for a photographic recording material, for example as a UV filter layer.

EXAMPLE 18

Polyolefin Articles in Contact with Pool Chemicals (Chlorine)

Film grade polyethylene is dry blended with 10% loading of a test additive of formula (A) or (B), as described in Example 8, and then melt compounded at 200° C. into fully formulated master batch pellets. The master batch pellets are dry blended with the polyethylene resin to get the final stabilizer concentration. The fully formulated resin is then blown at 200° C. into a 150 micron thick film using a DOLCI film line.

The resulting films are exposed for 4 hours to 20 liters of a aqueous solution containing 22.5 ppm Chlorine. The chlorine is made available via Leslies Fast Dissolving Super Shock—Super Chlorinator (Shock and Algae control) from OLIN Pool Products, Norwalk Conn. This Super Shock is 78% Calcium Hypochlorite was used accordingly to make the 22.5 ppm Cl available. After the 4 hours of the chlorine exposure the samples were rinsed in Distilled water 3 times, and air dried to prepare them for accelerated weathering. A duplicate sample was exposed to distilled water without the Chlorine. All the dipped samples are exposed for 250 hour intervals in a Weather-O-meter 65 WR (ASTM D 2565-85-dry) with a black panel temperature of 63° C. After each 250 hour interval of accelerated weathering, the samples were again exposed to the aqueous exposure as above. Failure is defined as the time to a 50% loss of original elongation. This test is designed to simulate exposure to pool chemicals as would be experienced by pool covers.

The films containing a present compound of formula (A2, 0.5%) and 0.5% of (i) or (viii) or (xiv) show good resistance to pool chemicals containing chlorine.

Other polyolefin articles, such as pool hoses, exposed to pool chemicals containing a present compounds (A) and (B) show good resistance to pool chemicals containing chlorine.

EXAMPLE 19

Stabilization of Polyolefins in Grease Filled Cable Construction 100 parts high density polyethylene are dry blended with 0.4 parts of Irganox® MD 1024 (1,2-bis(3,5-di-tert-butyl-4-hydroxyhydrocinnamoyl)hydrazine) and the stabilizers listed in Table 15 below. The mixtures are left compounded into pellets at 230° C. in a Superior/MPM extruder using a 24:1 L/D screw with Maddock mixing head at 60 rpm.

The pelletized polyethylene containing the stabilizer mixtures are compression molded at 400° F. into 10 mil (0.01 inch) thick films with Mylar backing. "Initial oxidation induction time" (OIT) is measured on these test films.

The sample films are then submersed in Witcogel®, available from Witco, a typical hydrocarbon cable filler grease used in telecom cables. The Witco filling compound contains 0.6% Irganox® 1035, thiodiethylene bis[3-(3,5-di-tert-butyl-4-hydroxyphenyl)propionate]. The sample films submersed in the filling compound are exposed in an air oven at 70° C. for 14 days. The samples are then wiped clean of the cable filler grease. "Aged oxidation induction time" is measured on these samples.

OIT testing is accomplished using a differential scanning calorimeter as per ASTM standard test method D3895. The test conditions are: Uncrimped aluminum pan; no screen; heat up to 200° C. under nitrogen, followed by a switch to a 100 milliliter/minute flow of oxygen. Oxidation induction time (OIT) is the time interval between the start of oxygen flow and the exothermic decomposition of the test specimen. OIT is reported in minutes; under the conditions of this test the longer the OIT the more effective the stabilizer mixture is at delaying the onset of oxidative degradation. Relative performance of stabilizer mixtures in grease filled cable applications can be predicted by comparing the initial OIT values, the aged OIT values and the differences between the initial OIT and aged OIT values.

TABLE 19

| Hindered Amine | UVA |
| --- | --- |
| 0.2% HALS 81 | 0.1% A2 + 0.2% i |
| 0.2% HALS 107 | 0.1% A2 + 0.2% xxvi |

EXAMPLE 20

Retention of Physical Properties and Color Control of Gamma Irradiated Polypropylene Unipol®, Union Carbide Corporation, gas phase polypropylene random copolymer with an initial melt flow rate of ca. 2 dg/min is via addition of a dialkylperoxide, controlled rheology modified to have a target melt flow rate of ca. 25 dg/min, an appropriate melt flow rate for injection molding. A clarifier is added at ca. 2200 ppm to enhance the transparency of the molded articles.

The formulations contain either a binary stabilizer system of a hindered hydrocarbyloxyamine of formula (A) or (B) and an organophosphorus compound, a binary system of a hindered hydrocarbyloxyamine of formula (A) or (B) and one or more compounds selected from the group of hydroxylamine stabilizers, benzofuranone stabilizers and amine oxide stabilizers, or a ternary system of a hindered hydrocarbyloxyamine of formula (A) or (B), one or more compounds selected from the group of hydroxylamine stabilizers, benzofuranone stabilizers and amine oxide stabilizers and an organophosphorus compound.

The hindered hydrocarbyloxyamines of formula (A) and (B) are typically present from about 0.1% to about 1% by weight, the hydroxylamines, benzofuranones and/or amine oxides are typically present from about 0.01% to about 0.5% by weight, and the organic phosphorus compounds are typically present from 0.05% to about 0.5% by weight, based on the overall formulation.

The formulations are prepared by dry blending the appropriate additives with the polymer in a Turbula® blender for twenty minutes followed by melt compounding on a single screw extruder at 500° F. (260° C.) using a polyolefin screw fitted with a Maddock mixing section. Each formulation also contains 750 ppm calcium stearate, 250 ppm of the dialkylperoxide 2,5-bis(tert-butylperoxyl)-2,5-dimethylhexane (90% tech. grade) and 2200 ppm of the Clarifier-1 (Millad® 3988). Each 2 kg batch is split into 1 kg lots, where 1 kg is multiple pass extruded and the other is injection molded into Type IV tensile bars. The Type IV tensile bars, and a set of 125 mil plaques are split into three sets and treated with gamma irradiation from a $^{60}$Co radiation source at 0, 30 and 60 Kilograys (or 0, 3 and 6 megarads) of exposure. The tensile bars are evaluated for retention of tensile strength and % elongation (at yield, at break) as a function of irradiation dose. The plaques are evaluated for changes in transparency or discoloration as a function of irradiation dose. The irradiated tensile bars, as well as the 125 mil plaques are then oven aged at 60° C. Color and haze development are measured weekly up to 4 weeks on the 125 mil plaques.

A typical organophosphorus stabilizer employed is Irgafos® 168, tris(2,4-di-tert-butylphenyl)phosphite, Ultranox® 626, bis(2,4-di-tert-butylphenyl)pentaerythritol diphosphite, Irgafos® P-EPQ, tetrakis(2,4-di-tert-butylphenyl)4,4'-biphenylene-diphosphonite or Ultranox® 641, 2,4,6-tri-t-butylphenyl-(2-ethyl-2-propylpropylidene)phosphite.

The amine oxide may be Genox™ EP, a di($C_{16}$-$C_{18}$)alkyl methyl amine oxide, CAS# 204933-93-7. The hydroxylamine stabilizer is for example Irgastab® FS-042, an N,N-di(alkyl)hydroxylamine produced by the direct oxidation of N,N-di(hydrogenated tallow)amine. The benzofuranone stabilizer may be Irganox® HP-136, 3-(3,4-dimethylphenyl)-5,7-di-tert-butyl-benzofuran-2-one. Irgafos®, Irgastab® and Irganox® are trademarks of Ciba Specialty Chemicals Corp. Genox™ and Ultranox® are trademarks of GE Chemicals.

The formulations including a present components (A2) and (i), (xii) or (xvi) (1:1) show superior physical property and color retention.

EXAMPLE 21

Retention of Physical Properties and Color Control of Gamma Irradiated HDPE

Solution phase Ziegler/Natta high density polyethylene copolymer (d=0.945 g/cm$^3$) with a nominal melt flow rate of ca. 17 dg/min (2.16 kg @ 190° C.) samples are prepared with the additives by adding a 5% additive concentrate to the "additive free" pelleted base resin in a Turbula® blender for twenty minutes followed by melt compounding on a single screw extruder at 450° F. (232° C.) using a polyolefin screw fitted with a Maddock mixing section. The formulations contain the same additives at the levels described in Example 16. Each formulation contains 500 ppm of calcium stearate as an acid scavenger. Each 2 kg batch is split into 1 kg lots and 1 kg is multiple pass extruded and the other is injection molded into Type IV tensile bars or compression molded into 125 mil plaques.

The Type IV tensile bars, 125 mil plaques and 1$^{st}$ pass extrusion pellets are split into three sets and treated with gamma irradiation from a $^{60}$Co radiation source at 0, 30 and 60 Kilograys (or 0, 3 and 6 megarads) of exposure. The tensile bars are evaluated for retention of tensile strength and % elongation (at yield, at break), the plaques are evaluated for discoloration, and the pellets are tested for retention of melt flow rate, all as a function of irradiation dose. The irradiated tensile bars, as well as the 125 mil plaques, are oven aged at 60° C. Color development, tensile strength and % elongation are measured during oven aging at 60° C.

The formulations containing a present UVA combination as described in example 20 and additionally 1% of a hindered amine (109, 107 or 108) show superior physical property and color retention.

EXAMPLE 22

Retention of Physical Properties and Color Control of Gamma Irradiated Polypropylene Homopolymer for Fiber Polypropylene homopolymer, Ti/Al catalyst, bulk phase process, with a nominal melt flow index of ca. 15 dg/min at 2.16 kg/230° C. is extruded into fibers at 525° F. and a draw ratio of 3.5:1 and 15 Denier per filament. The fibers are knitted into socks. Samples are also compression molded into plaques. The individual formulations each contain a 1:1 blend of calcium stearate/dihydrotalcite at a total level of 500 ppm as an acid scavenger. Formulations are otherwise prepared as per Example 20 with additional use of HALS No. 107 or 76.

The fibers, socks and plaques are treated with gamma irradiation from a $^{60}$Co radiation source at 0, 30, and 60 Kilograys (or 0, 3 and 6 megarads) of exposure.

The formulations containing a present stabilizer combination show superior color and/or physical property retention.

EXAMPLE 23

Retention of Physical Properties and Color Control of Gamma Irradiated Linear Low Density Polyethylene for Film Unipol®, Union Carbide Corporation, gas phase E/H LLDPE copolymer; Ti/Al catalyst; melt index ca. 1 dg/min. at 2.16 kg/190° C. is extruded into blown films at 450° F. to produce 1.5 mil films. The individual formulations each contain zinc stearate at a total level of 500 ppm as an acid scavenger. Formulations are otherwise prepared as per Example 20.

The films are treated with gamma irradiation from a $^{60}$Co radiation source at 0, 30 and 60 Kilograys (or 0, 3 and 6 megarads) of exposure.

The films containing the formulations of the present invention show superior physical property and color retention.

EXAMPLE 24

Non-Woven Polypropylene Fiber Agricultural Film

Forming spunbonded fabrics is a conventional process well know in the art. Fiber grade polypropylene is dry blended with 10% loading of the test additive and then melt compounded at 220° C. into masterbatch pellets. The master batch pellets are dry blended with polypropylene resin (MFR=35-50) at a ratio to yield 1.0% additive. Spunbonded fibers are prepared by extrusion of molten polypropylene resin (die temperature=230° C.) as filaments from a plurality of fine circular capillaries of a spinneret. Cooling air is fed into a quenching chamber (2,400 rpm) wherein the filaments are cooled. The cooling air is then sucked through a nozzle, which accelerates the flow of air creating a force which draws the filaments. The drawn filaments are then passed through a diffusor and deposited on a conveyor belt (33 m/min) to form a non woven fabric.

Forming meltblown fabrics is a conventional process well know in the art. Polypropylene is dry blended with 10% loading of a test additive combination (A2) and (B) and then melt compounded at 220° C. into masterbatch pellets. The master batch pellets are dry blended with polypropylene resin (MFR 1200) at a ratio to yield 1.0% additive. Meltblown fibers are prepared by extrusion of molten polypropylene resin as filaments from a plurality of fine circular capillaries of a spinneret. A high-velocity heated air stream attenuates the filaments of molten polypropylene to reduce their diameter. There after the meltblown fibers are carried by the high-velocity heated air stream and are deposited on a collection surface to form a web of randomly dispersed meltblown fibers. Thermal bonding of the web to retain integrity and strength occurs as a separate downstream operation.

The nonwoven fabrics containing a present compound of formula A2 and (i) or (iv) or (xii) show good UV stability in agricultural applications such as direct covers, small tunnel covers, and shade cloths and also show good stability after exposure to agricultural chemicals such as pesticides and herbicides.

What is claimed is:

1. A composition comprising
(A) a compound of the formula I

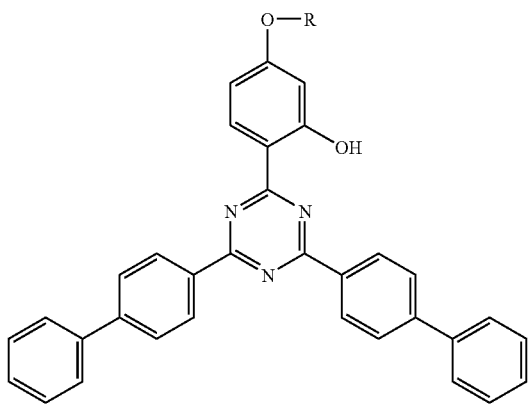

wherein R is $(CH_2-CH_2-O-)_n-R_2$; $-CH_2-CH(OH)-CH_2-O-R_2$; or $-CH(R_3)-CO-O-R_4$; n is 0 or 1; $R_2$ is $C_1-C_{13}$alkyl or $C_2-C_{20}$alkenyl or $C_6-C_{12}$aryl or $CO-C_1-C_{18}$alkyl; $R_3$ is H or $C_1-C_8$alkyl; $R_4$ is $C_1-C_{12}$alkyl or $C_2-C_{12}$alkenyl or $C_5-C_8$cycloalkyl; and (B) a compound selected from benzotriazoles of the formula (IIa), 2-hydroxybenzophenones of the formula (IIb), oxalanilides of the formula (IIc), 2-hydroxyphenyltriazines of formula (IId), cinnamates of formula (IIe), and benzoates of formula (IIf)

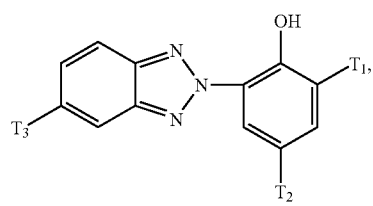

wherein $T_1$ is hydrogen, $C_1-C_{18}$alkyl, or $C_1-C_{18}$alkyl which is substituted by phenyl,
or $T_1$ is a group of the formula

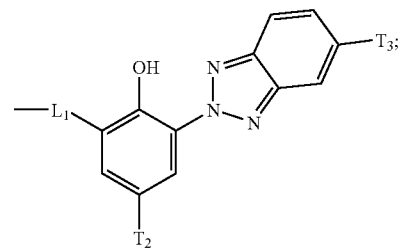

$L_1$ is a divalent group, for example $-(CH_2)_n-$, where n is from the range 1-8;

$T_2$ is hydrogen, $C_1-C_{18}$alkyl, or is $C_1-C_{18}$alkyl which is substituted by $COOT_5$, $C_1-C_{18}$alkoxy, hydroxyl, phenyl or $C_2-C_{18}$acyloxy;

$T_3$ is hydrogen, halogen, $C_1$-$C_{18}$alkyl, $C_1$-$C_{18}$alkoxy, $C_2$-$C_{18}$acyloxy, phenyl, or is perfluoroalkyl of 1 to 12 carbon atoms;

$T_5$ is $C_1$-$C_{18}$alkyl or $C_4$-$C_{50}$alkyl interrupted by one or more O and/or substituted by OH or by a group

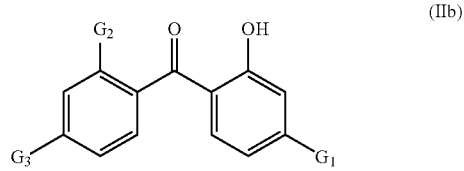
(IIb)

wherein
$G_1$, $G_2$ and $G_3$ independently are hydrogen, hydroxy or $C_1$-$C_{18}$alkoxy;

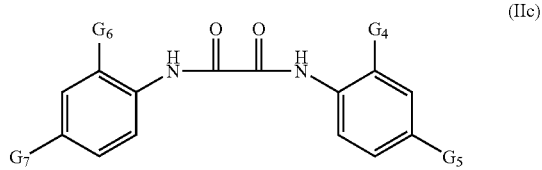
(IIc)

wherein
$G_4$, $G_5$, $G_6$ and $G_7$ independently are hydrogen, $C_1$-$C_{12}$alkyl or $C_1$-$C_{12}$alkoxy;

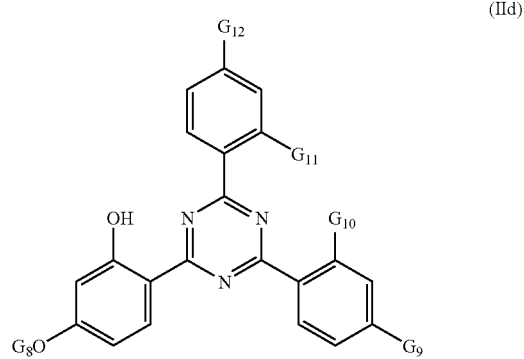
(IId)

wherein
$G_8$ is $C_1$-$C_{16}$alkyl, or is $C_4$-$C_{18}$alkyl which is interrupted by COO or OCO or O, or is interrupted by O and substituted by OH;
$G_9$, $G_{10}$, $G_{11}$ and $G_{12}$ independently are hydrogen, methyl, hydroxy or $OG_8$;

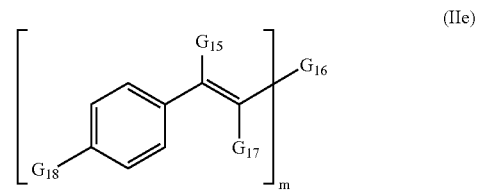
(IIe)

wherein
m is an integer from 1 to 4;
$G_{15}$ is hydrogen or phenyl;
if n is 1, $G_{16}$ is COO-$G_{19}$;
if n is 2, $G_{16}$ is $C_2$-$C_{12}$alkane-dioxycarbonyl;
if n is 3, $G_{16}$ is $C_3$-$C_{12}$alkane-trioxycarbonyl;
if n is 4, $G_{16}$ is $C_4$-$C_{12}$alkane-tetraoxycarbonyl;
$G_{17}$ is hydrogen, CN, or is COO-$G_{19}$;
$G_{18}$ is hydrogen or methoxy;
$G_{19}$ is $C_1$-$C_{18}$alkyl;

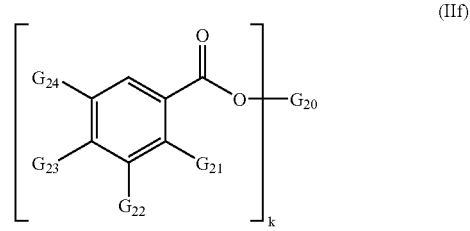
(IIf)

wherein
k is 1 or 2;
when k is 1, $G_{20}$ is $C_1$-$C_{18}$alkyl, phenyl or phenyl substituted by $C_1$-$C_{12}$alkyl, and $G_{21}$ is hydrogen;
when k is 2, $G_{20}$ and $G_{21}$ together are the tetravalent group $G_{22}$ and $G_{24}$ independently are hydrogen or $C_1$-$C_8$alkyl;
$G_{23}$ is hydrogen or hydroxy,
provided that R in formula (I) is $(CH_2-CH_2-O-)_n-R_2$ if component (B) contains a 2-hydroxyphenyltriazine of formula (IId) wherein $G_9$, $G_{10}$, $G_{11}$ or $G_{12}$ are methyl.

2. A composition according to claim 1 wherein component (B) is selected from the compounds (i) to (xlv):
i. 2-(3',5'-di-tert-butyl-2'-hydroxyphenyl)-5-chlorobenzotriazole,
ii. 2-(3',5'-di-tert-amyl-2'-hydroxyphenyl)benzotriazole,
iii. 2-(3',5'-bis(α,α-dimethylbenzyl)-2'-hydroxyphenyl)benzotriazole,
iv. 2-(3'-tert-butyl-2'-hydroxy-5'-(2-octyloxycarbonylethyl)phenyl)benzotriazole,
v. 2,2'-methylene-bis[4-(1,1,3,3-tetramethylbutyl)-6-benzotriazole-2-ylphenol],
vi. the transesterification product of 2-[3'-tert-butyl-5'-(2-methoxycarbonylethyl)-2'-hydroxyphenyl]-2H-benzotriazole with polyethylene glycol 300,
vii. 2-[2'-hydroxy-3'-(α,α-dimethylbenzyl)-5'-(1,1,3,3-tetramethylbutyl)phenyl]benzotriazole,
viii. 5-trifluoromethyl-2-(2-hydroxy-3-α-cumyl-5-tert-octylphenyl)-2H-benzotriazole,
ix. 2-(2'-hydroxy-5'-(2-hydroxyethyl)phenyl)benzotriazole,
x. 2-(2'-hydroxy-5'-(2-methacryloyloxyethyl)phenyl)benzotriazole,
xi. 2,4-bis(2,4-dimethylphenyl)-6-(2-hydroxy-4-alkyloxyphenyl)-1,3,5-triazine, where alkyl is a mixture of $C_8$-alkyl groups, xii. 2,4-bis(2,4-dimethylphenyl)-6-(2-hydroxy-4-octyloxyphenyl)-1,3,5-triazine,
xiii. 2,4-diphenyl-6-(2-hydroxy-4-[α-ethylhexanoyloxyethyl]phenyl)-1,3,5-triazine,
xiv. 2,4-bis(2-hydroxy-4-butyloxyphenyl)-6-(2,4-bis-butyloxyphenyl)-1,3,5-triazine,
xv. 2,4,6-tris(2-hydroxy-4-[1-ethoxycarbonylethoxy]phenyl)-1,3,5-triazine,
xvi. the reaction product of tris(2,4-dihydroxyphenyl)-1,3,5-triazine with the mixture of α-chloropropionic esters (made from isomer mixture of $C_7$-$C_9$ alcohols),
xvii. 2-[4-(dodecyloxy/tridecyloxy-2-hydroxypropoxy)-2-hydroxyphenyl]-4,6-bis(2,4-dimethylphenyl)1,3,5-triazine,
xviii. 2-{2-hydroxy-4-[3-(2-ethylhexyl-1-oxy)-2-hydroxypropyloxy]phenyl}-4,6-bis(2,4-dimethylphenyl)-1,3,5-triazine,
xix. 2-(2-hydroxy-4-hexyloxyphenyl)-4-6-diphenyl-1,3,5-triazine,
xx. 2-(3'-tert.butyl-5'-methyl-2'-hydroxyphenyl)-5-chloro-benzotriazole,
xxi. 2-(3'-sec.butyl-5'-tert.butyl-2'-hydroxyphenyl)-benzotriazole,
xxii. 2-(3',5'-di-tert-butyl-2'-hydroxyphenyl)-benzotriazole,
xxiii. 2-(5'-tert.octyl-2'-hydroxyphenyl)-benzotriazole,
xxiv. 2-(3'-dodecyl-5'-methyl-2'-hydroxyphenyl)-benzotriazole,
xxv. 2-(3'-tert.butyl-5'-(2-octyloxycarbonylethyl)-2'-hydroxyphenyl)-5-chloro-benzotriazole,
xxvi. 2-(5'-methyl-2'-hydroxyphenyl)-benzotriazole,
xxvii. 2-(5'-tert.butyl-2'-hydroxyphenyl)-benzotriazole,
xxx. the compound of formula

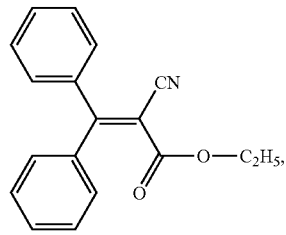

xxxi. the compound of formula

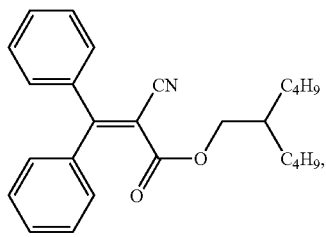

xxxii. 2-ethylhexyl-p-methoxycinnamate,
xxxiii. 2,4-dihydroxybenzophenone,
xxxiv. 2-hydroxy-4-methoxybenzophenone,
xxxv. 2-hydroxy-4-dodecyloxybenzophenone,
xxxvi. 2-hydroxy-4-octyloxybenzophenone,
xxxvii. 2,2'-dihydroxy-4-methoxybenzophenone,
xxxviii. the compound of formula

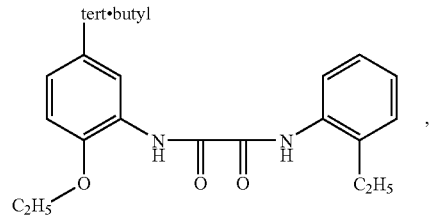

xxxix. the compound of formula

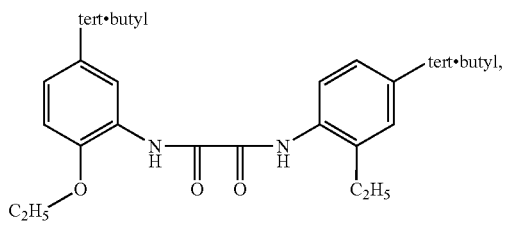

xl. the compound of formula

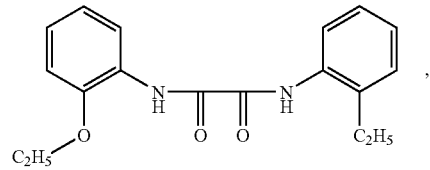

xli. the compound of formula

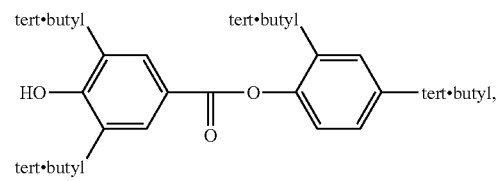

xlii. the compound of formula I

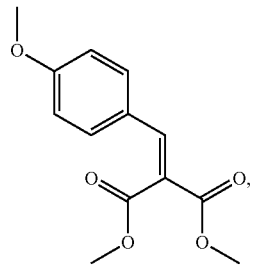

xliii. the compound of formula

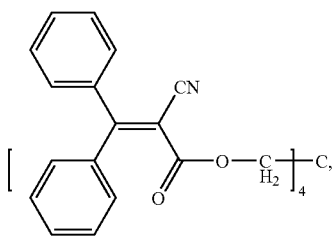

xliv. the compound of formula

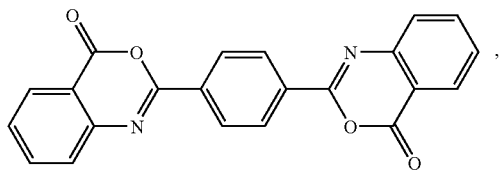

xlv. the compound of formula

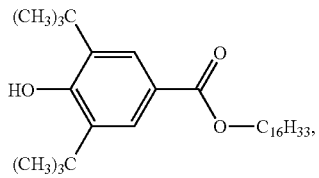

provided that R in formula (I) is $(CH_2—CH_2—O—)_n—R_2$ if component (B) contains compound xi, xii, xvii or xviii.

3. A composition according to claim 1 wherein component (A) is selected from compounds of the formula (I) wherein R contains an uninterrupted, branched or unbranched $C_7$-$C_{13}$alkyl chain, and wherein component (B) is selected from benzotriazoles the formula (IIa) and 2-hydroxybenzophenones of the formula (IIb).

4. A composition according to claim 2 wherein component (A) is selected from the compounds
 (A1) 2-(2-hydroxy-4-[1-octyloxycarbonylethoxy]phenyl)-4,6-bis(4-phenylphenyl)-1,3,5-triazine and/or
 (A2) 2-(2-hydroxy-4-(2-ethylhexyl)oxy)phenyl-4,6-bis(4-phenyl)phenyl-1,3,5-triazine.

5. A composition according to claim 4 wherein component (A) is the compound (A1) and component (B) is selected from the compounds i-iv, vi-xi, xiii-xviii, xx, xxiii-xxxix.

6. A composition according to claim 4 wherein component (A) is the compound (A2) and component (B) is selected from the compounds i-viii, xii, xiii, xix-xxiii, xxv-xxvii, xxx-xxxvi, xl-xlv.

7. A composition according to claim 1 comprising a further additive selected from plasticizers, lubricants, emulsifiers, pigments, rheology additives, catalysts, flow-control agents, optical brighteners, further light stabilizers, antioxidants, clarifiers, flameproofing agents, anti-static agents, benzoxazinone UV absorbers, blowing agents and thiosynergists.

8. A composition according to claim 7 comprising a further additive selected from sterically hindered amine stabilizers.

9. A composition according to claim 1 comprising the components (A) and (B) in a weight ratio ranging from 1 part (A): 20 parts (B) to 10 parts (A): 1 part (B).

10. A composition comprising
 (a) an organic material and
 (b) as stabilizer or protecting agent against the effects of light, oxygen and/or heat or ultraviolet filtering agent, a composition comprising a compound (A) and a compound (B) according to claim 1.

11. Composition according to claim 10 wherein the organic material is a thermoplastic polymer, a crosslinkable binder of a coating composition, the crosslinked coating, a dye or printing ink or a color photographic material.

12. Composition according to claim 10 wherein the organic material of component (a) is selected from thermoplastic polymers, and component (b) is a combination of compound (A2) with a compound (B) selected from the compounds i-x, xii, xiii, xix-xxiii, xxv-xxvii, xxx-xxxvi, and xl-xlv.

13. Composition according to claim 10 wherein the organic material of component (a) is selected from a crosslinkable binder of a coating composition, a crosslinked coating, a dye or printing ink or a color photographic material, and component (b) is a combination of compound (A1) with a compound (B) selected from the compounds i iv, vi-xi, xiii xviii, xx, xxiii xxvii, xxx-xxxix.

14. Composition according to claim 10 wherein component (b) and optional further stabilizers are present in an amount of 0.01 to 10% by weight, relative to component (a).

15. Composition according to claim 10 which is a molding, rotomolded article, injection molded article, blow molded article, film, tape, mono-filament, fiber, nonwoven, profile, adhesive or putty, surface coating.

16. A process for stabilizing an organic material against damage by light, oxygen and/or heat, which comprises adding to or applying to said material a composition according to claim 1.

* * * * *